US009089610B2

(12) United States Patent
McManus et al.

(10) Patent No.: US 9,089,610 B2
(45) Date of Patent: Jul. 28, 2015

(54) COMPLEXES OF SMALL-INTERFERING NUCLEIC ACIDS

(75) Inventors: Samuel P. McManus, Huntsville, AL (US); Timothy A. Riley, Huntsville, AL (US); Sean M. Culbertson, Gurley, AL (US); Antoni Kozlowski, Huntsville, AL (US); Dennis G. Fry, Huntsville, AL (US); Patrick D. Youso, Huntsville, AL (US)

(73) Assignee: Nektar Therapeutics, San Francisco, CA (US)

( * ) Notice: Subject to any disclaimer, the term of this patent is extended or adjusted under 35 U.S.C. 154(b) by 18 days.

(21) Appl. No.: 13/059,624

(22) PCT Filed: Aug. 19, 2009

(86) PCT No.: PCT/US2009/004744
§ 371 (c)(1),
(2), (4) Date: Apr. 26, 2011

(87) PCT Pub. No.: WO2010/021718
PCT Pub. Date: Feb. 25, 2010

(65) Prior Publication Data
US 2011/0213013 A1    Sep. 1, 2011

Related U.S. Application Data

(60) Provisional application No. 61/189,528, filed on Aug. 19, 2008, provisional application No. 61/198,935, filed on Nov. 12, 2008, provisional application No. 61/153,636, filed on Feb. 18, 2009.

(51) Int. Cl.
*A61K 47/48* (2006.01)

(52) U.S. Cl.
CPC ..... *A61K 47/48092* (2013.01); *A61K 47/48215* (2013.01)

(58) Field of Classification Search
USPC .................. 435/6, 91.1, 91.31, 455, 458, 6.1; 514/1, 2, 44, 23, 53, 54; 536/23.1, 536/24.5; 424/486, 489, 423; 977/773
See application file for complete search history.

(56) References Cited

U.S. PATENT DOCUMENTS

| | | | |
|---|---|---|---|
| 4,810,646 A | 3/1989 | Jamas et al. | |
| 4,992,540 A | 2/1991 | Jamas et al. | |
| 5,028,703 A | 7/1991 | Jamas et al. | |
| 5,607,677 A | 3/1997 | Jamas et al. | |
| 5,741,495 A | 4/1998 | Jamas et al. | |
| 5,898,031 A | 4/1999 | Crooke | |
| 5,932,462 A | 8/1999 | Harris et al. | |
| 6,107,094 A | 8/2000 | Crooke | |
| 6,309,623 B1 | 10/2001 | Weers et al. | |
| 6,433,040 B1 | 8/2002 | Dellamary et al. | |
| 6,565,885 B1 | 5/2003 | Tarara et al. | |
| 6,602,977 B1 | 8/2003 | Ljungqvist et al. | |
| 6,673,901 B2 | 1/2004 | Koide | |
| 6,703,199 B1 | 3/2004 | Koide | |
| 6,740,734 B1 | 5/2004 | Nilsson et al. | |
| 6,946,117 B1 | 9/2005 | Schutt et al. | |
| 7,056,704 B2 | 6/2006 | Tuschl et al. | |
| 7,078,196 B2 | 7/2006 | Tuschl et al. | |
| 7,078,490 B2 | 7/2006 | Koide | |
| 7,119,171 B2 | 10/2006 | Koide | |
| 7,223,803 B2 | 5/2007 | Harris et al. | |
| 7,452,987 B2 | 11/2008 | Giese et al. | |
| 8,916,693 B2 | 12/2014 | Mcmanus et al. | |
| 2002/0086356 A1 | 7/2002 | Tuschl et al. | |
| 2002/0193331 A1* | 12/2002 | Boussif et al. .................. 514/44 |
| 2003/0108923 A1 | 6/2003 | Tuschl et al. | |
| 2003/0166783 A1 | 9/2003 | Davis et al. | |
| 2003/0190654 A1 | 10/2003 | Heidenreich et al. | |
| 2003/0206887 A1 | 11/2003 | Morrissey et al. | |
| 2004/0001811 A1 | 1/2004 | Kreutzer et al. | |
| 2004/0038921 A1 | 2/2004 | Kreutzer et al. | |
| 2004/0053875 A1 | 3/2004 | Kreutzer et al. | |
| 2004/0072779 A1 | 4/2004 | Kreutzer et al. | |
| 2004/0091457 A1 | 5/2004 | John et al. | |
| 2004/0102408 A1 | 5/2004 | Kreutzer et al. | |
| 2004/0121348 A1 | 6/2004 | Kreutzer et al. | |
| 2004/0126791 A1 | 7/2004 | Wajant et al. | |
| 2004/0175703 A1 | 9/2004 | Kreutzer et al. | |
| 2004/0180351 A1 | 9/2004 | Giese et al. | |
| 2004/0249178 A1 | 12/2004 | Vargeese et al. | |
| 2004/0259247 A1 | 12/2004 | Tuschl et al. | |
| 2004/0259248 A1 | 12/2004 | Tuschl et al. | |
| 2005/0014903 A1 | 1/2005 | Kozlowski et al. | |

(Continued)

FOREIGN PATENT DOCUMENTS

DE     200 23 125     6/2003
EP     1 144 623      8/2002
(Continued)

OTHER PUBLICATIONS

Amiji et al., Surface Mofication of Polymeric Biomaterials with Poly(ethylene oxide) in Polymers of Biological and Biomedical Significance; Shalaby, S., et al., ACS Symposium Series; ACS, Washington, DC (1993).*
Mao et al., J. Controlled Release, vol. 70, pp. 399-421 (2001).*
European Examination Report corresponding to European Patent Application No. 09 789 176.6 dated Oct. 27, 2011.
Amarzguioui, et al., "Rational design and in vitro and in vivo delivery of Dicer substrate siRNA," Nature Protocols, vol. 1, No. 2, pp. 508-517, (2006).
Amstutz, et al., "Intracellular Kinase Inhibitors Selected from Combinatorial Libraries of Designed Ankyrin Repeat Proteins," The J. of Biol. Chem., vol. 280, No. 26, pp. 24715-24722, (2005).
Binz, et al., "Engineering novel binding proteins from nonimmunoglobulin domains," Nature Biotechnol., vol. 23, No. 10, pp. 1257-1268, (Oct. 2005).
Binz, et al., "High-affinity binders selected from designed ankyrin repeat protein libraries," Nature Biotechnol., vol. 22, No. 5, pp. 575-582, (May 2004).

(Continued)

*Primary Examiner* — Jane Zara
(74) *Attorney, Agent, or Firm* — Mark A. Wilson

(57) ABSTRACT

The present invention relates to complexes of small-interfering nucleic acids (siNA). Compositions of siNA suited for administration to a patient are described. Methods for delivering the compositions are also described.

22 Claims, 21 Drawing Sheets

(56) References Cited

U.S. PATENT DOCUMENTS

| | | |
|---|---|---|
| 2005/0026278 A1 | 2/2005 | Tuschl et al. |
| 2005/0043263 A1 | 2/2005 | Giese et al. |
| 2005/0059005 A1 | 3/2005 | Tuschl et al. |
| 2005/0074757 A1 | 4/2005 | Kreutzer et al. |
| 2005/0100907 A1 | 5/2005 | Kreutzer et al. |
| 2005/0112187 A1* | 5/2005 | Meyer ............................ 424/450 |
| 2005/0119470 A1 | 6/2005 | Manoharan et al. |
| 2005/0176667 A1 | 8/2005 | Vornlocher |
| 2005/0182005 A1 | 8/2005 | Tuschl et al. |
| 2005/0186591 A1 | 8/2005 | Bumcrot et al. |
| 2005/0202077 A1 | 9/2005 | Watson et al. |
| 2005/0227934 A1 | 10/2005 | Stoffel et al. |
| 2005/0234006 A1 | 10/2005 | Tuschl et al. |
| 2005/0234007 A1 | 10/2005 | Tuschl et al. |
| 2005/0244858 A1 | 11/2005 | Rossi et al. |
| 2005/0277610 A1 | 12/2005 | Rossi et al. |
| 2005/0281781 A1 | 12/2005 | Ostroff |
| 2005/0288244 A1 | 12/2005 | Manoharan et al. |
| 2006/0008822 A1 | 1/2006 | Manoharan et al. |
| 2006/0014289 A1 | 1/2006 | Ahmadian et al. |
| 2006/0035254 A1 | 2/2006 | Manoharan et al. |
| 2006/0035815 A1 | 2/2006 | Chen et al. |
| 2006/0122137 A1 | 6/2006 | Quay et al. |
| 2006/0142230 A1 | 6/2006 | Quay |
| 2006/0160123 A1 | 7/2006 | Quay |
| 2006/0166910 A1 | 7/2006 | Tuschl et al. |
| 2006/0188472 A1 | 8/2006 | Sommermeyer et al. |
| 2006/0212950 A1 | 9/2006 | Tuschl et al. |
| 2006/0287260 A1 | 12/2006 | Manoharan et al. |
| 2007/0003960 A1 | 1/2007 | Tuschl et al. |
| 2007/0003961 A1 | 1/2007 | Tuschl et al. |
| 2007/0003962 A1 | 1/2007 | Tuschl et al. |
| 2007/0003963 A1 | 1/2007 | Tuschl et al. |
| 2007/0020308 A1* | 1/2007 | Richard et al. ................. 424/423 |
| 2007/0031371 A1 | 2/2007 | McManus et al. |
| 2007/0054279 A1 | 3/2007 | Manoharan et al. |
| 2007/0093445 A1 | 4/2007 | Tuschl et al. |
| 2007/0135372 A1 | 6/2007 | MacLachlan et al. |
| 2007/0155658 A1 | 7/2007 | Quay et al. |
| 2007/0160980 A1 | 7/2007 | Haeberli et al. |
| 2007/0161595 A1 | 7/2007 | Bumcrot et al. |
| 2007/0172430 A1 | 7/2007 | Brito et al. |
| 2007/0185050 A1 | 8/2007 | Heidenreich et al. |
| 2007/0197460 A1 | 8/2007 | De Fougerolles et al. |
| 2007/0213257 A1 | 9/2007 | Sweedler |
| 2007/0213292 A1 | 9/2007 | Stoffel et al. |
| 2007/0213293 A1 | 9/2007 | McSwiggen et al. |
| 2007/0229266 A1 | 10/2007 | Gibson |
| 2007/0254362 A1 | 11/2007 | Quay et al. |
| 2007/0265220 A1 | 11/2007 | Rossi et al. |
| 2007/0269892 A1 | 11/2007 | Adami et al. |
| 2007/0275465 A1 | 11/2007 | Woppmann et al. |
| 2007/0275923 A1 | 11/2007 | Chen et al. |
| 2007/0276134 A1 | 11/2007 | Sweedler et al. |
| 2007/0281900 A1 | 12/2007 | Cui et al. |
| 2007/0287179 A1 | 12/2007 | Tuschl et al. |
| 2007/0293449 A1 | 12/2007 | Cui et al. |
| 2007/0293657 A1 | 12/2007 | Adami et al. |
| 2007/0299043 A1* | 12/2007 | Hunter et al. .................. 514/171 |
| 2008/0039414 A1 | 2/2008 | McSwiggen et al. |
| 2008/0044438 A1 | 2/2008 | Ostroff et al. |
| 2008/0064863 A1 | 3/2008 | Nagasaki et al. |
| 2008/0070856 A1 | 3/2008 | Kreutzer et al. |
| 2008/0076701 A1 | 3/2008 | Quay et al. |
| 2008/0097087 A1 | 4/2008 | Nagasaki et al. |
| 2008/0131371 A1 | 6/2008 | Artursson et al. |
| 2008/0166800 A1 | 7/2008 | Kreutzer et al. |
| 2008/0194512 A1 | 8/2008 | John et al. |
| 2008/0233651 A1 | 9/2008 | Kreutzer et al. |
| 2008/0249049 A1 | 10/2008 | Kataoka et al. |
| 2008/0261303 A1 | 10/2008 | Kreutzer et al. |
| 2009/0082274 A1 | 3/2009 | Stumpp et al. |
| 2010/0092572 A1* | 4/2010 | Kaeuper et al. ................ 424/499 |
| 2010/0129460 A1* | 5/2010 | Adami et al. ................... 424/499 |
| 2010/0291205 A1* | 11/2010 | Downie et al. ................. 424/457 |
| 2010/0311654 A1* | 12/2010 | Roy et al. ........................ 514/9.7 |
| 2011/0269916 A1* | 11/2011 | Chenault et al. ................ 525/450 |
| 2012/0100096 A1 | 4/2012 | Mcmanus et al. |
| 2012/0189704 A1* | 7/2012 | Ben-Shalom et al. ......... 424/493 |
| 2013/0266650 A1* | 10/2013 | JACKSON et al. ............ 424/472 |

FOREIGN PATENT DOCUMENTS

| | | |
|---|---|---|
| EP | 1 214 945 | 6/2005 |
| EP | 1 352 061 | 5/2006 |
| EP | 1 527 176 | 1/2007 |
| EP | 1 797 901 | 6/2007 |
| EP | 1 801 210 | 6/2007 |
| EP | 1 857 547 | 11/2007 |
| EP | 1 536 827 | 1/2009 |
| EP | 1 551 868 | 1/2009 |
| WO | WO 99/16873 | 4/1999 |
| WO | WO 00/63243 | 10/2000 |
| WO | WO 01/64942 | 9/2001 |
| WO | WO 02/20565 | 3/2002 |
| WO | WO 02/088171 | 11/2002 |
| WO | WO 2004/035615 | 4/2004 |
| WO | WO 2004/044011 | 5/2004 |
| WO | WO 2005/000320 | 1/2005 |
| WO | WO 2005/019254 | 3/2005 |
| WO | WO 2005/105152 | 11/2005 |
| WO | WO 2006/023544 | 3/2006 |
| WO | WO 2006/069782 | 7/2006 |
| WO | WO 2006/083275 | 8/2006 |
| WO | WO 2007/021142 | 2/2007 |
| WO | WO 2007/084684 | 7/2007 |
| WO | WO 2007/121947 | 11/2007 |
| WO | WO 2007/121956 | 11/2007 |
| WO | WO 2008/031899 | 3/2008 |
| WO | WO 2008/082282 | 7/2008 |
| WO | WO 2008/109105 | 9/2008 |
| WO | WO 2009/040338 | 4/2009 |
| WO | WO 2010/021720 | 2/2010 |
| WO | WO 2010/021720 | 4/2010 |

OTHER PUBLICATIONS

De Fougerolles, et al., "Interfering with disease: a progress report on siRNA-based therapeutics," Nature Rev., vol. 6, pp. 443-453, (Jun. 2007).

Duan, et al., "Cationic nano-copolymers mediated IKKβ targeting siRNA inhibit the proliferation of human Tenon's capsule fibroblasts in vitro," Mol. Vision, vol. 14, pp. 2616-2628, (2008).

Hosseinkhani, et al., "Liver targeting of plasmid DNA by pullulan conjugation based on metal coordination," J. of Contrl. Rel., vol. 83, pp. 287-302, (2002).

Howard, et al., "RNA Interference in Vitro and in Vivo Using a Chitosan/siRNA Nanoparticle System," Mol. Therapy, vol. 14, No. 4, pp. 476-484, (Oct. 2006).

Jiang, et al., "Chitosan-graft-polyethylenimine as a gene carrier," J. of Contrl. Rel., vol. 117, pp. 273-280, (2007).

Kataoka, et al., "Block copolymer micelles as vehicles for drug delivery," J. of Contrl. Rel., vol. 24, pp. 119-132, (1993).

Katas, et al., "Development and characterisation of chitosan nanoparticles for siRNA delivery," J. of Contrl. Rel., vol. 115, pp. 216-225, (2006).

Kim, et al., "Synthetic dsRNA Dicer substrates enhance RNAi potency and efficacy," Nature Biotechnol., vol. 23, No. 2, pp. 222-226, (Feb. 2005).

Krutzfeldt, et al., "Silencing of microRNAs in vivo with antagomirs," Nature, vol. 438, pp. 685-689, (Dec. 2005).

Ouchi, et al., "Design of Antitumor Agent-Terminated Poly(Ethylene Glycol) Conjugate as Macromolecular Prodrug," Polymer Preprints, vol. 38, No. 1, pp. 582-583, (1997).

Rojanarata, et al., "Chitosan-Thiamine Pyrophosphate as a Novel Carrier for siRNA Delivery," Pharmaceu. Res., vol. 25, No. 12, pp. 2807-2814, (Dec. 2008).

Rose, et al., "Functional polarity is introduced by Dicer processing of short substrate RNAs," Nucl. Acids Res., vol. 33, No. 13, pp. 4140-4156, (2005).

Stumpp, et al., "DARPins: A true alternative to antibodies," Curr. Opin. in Drug Discov. & Dev., vol. 10, No. 2, pp. 153-159, (2007).

(56) References Cited

OTHER PUBLICATIONS

Zahnd, et al., "A Designed Ankyrin Repeat Protein Evolved to Picomolar Affinity to Her2," J. Mol. Biol., vol. 369, pp. 1015-1028, (2007).
Zalipsky, "Chemistry of polyethylene glycol conjugates with biologically active molecules," Adv. Drug Del. Rev., vol. 16, pp. 157-182, (1995).
PCT International Search Report corresponding to PCT Application No. PCT/US2009/004744 date of mailing Feb. 9, 2010.
PCT International Preliminary Report on Patentability corresponding to PCT Application No. PCT/US2009/004744 date of mailing Mar. 3, 2011.
Enzon Pharmaceuticals, Macromolecular Engineering Technologies, 16 pages, (2004).
NEKTAR™—Transforming Therapeutics, Nektar Molecule Engineering: Polyethylene Glycol and Derivatives for Advanced PEGylation, 24 pages, Catalog—2003, (Jul. 2003).
NEKTAR™—Transforming Therapeutics, Nektar Advanced PEGylation: Polyethylene Glycol and Derivatives for Advanced PEGylation, 27 pages, Catalog—2004, (Jul. 2004).
NEKTAR™—Transforming Therapeutics, Nektar Advanced PEGylation: Polyethylene Glycol and Derivatives for Advanced PEGylation, 33 pages, (Catalog 2005-2006).
NOF Corporation, PEG Derivatives, Phospholipid and Drug Delivery Materials for Pharmaceuticals, pp. 1-46, Catalogue 2003-1st, (Jan. 2003).
NOF Corporation, PEG Derivatives, Phospholipid and Drug Delivery Materials for Pharmaceuticals, pp. 1-50, Catalogue 2003-2nd, (Mar. 2004).
NOF Corporation, PEG Derivatives, Phospholipids and Drug Delivery Materials for Pharmaceutical Products and Formulations, 60 pages, Catalogue Ver. 8, (Apr. 2006).
Polypure Products, PEG amines; PEG acids and amino acids; PEG thiols and disulfides; BIOTINS, 5 pages, (Apr. 2004).
Polypure Products, PEG amines; PEG acids and amino acids; PEG thiols and disulfides; BIOTINS, 5 pages, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™(dPEG™) derivatives, (Product Catalog), pp. 1-51, (Updated: Jul. 18, 2005).
Quanta Biodesign, Ltd., Leading innovator, producer and provider of monodisperse discrete PEG™ (dPEG™) derivatives, (Product Catalog), pp. 1-51, (Updated: Nov. 17, 2005).
Shearwater Polymers, Inc., Polyethylene Glycol and Derivatives, 50 pages, (Catalog—Mar. 1995).
Shearwater Polymers, Inc., Polyethylene Glycol and Derivatives, 55 pages, (Catalog—Jul. 1997).
Shearwater Polymers, Inc., Polyethylene Glycol and Derivatives: Functionalized Biocompatible Polymers for Research and Pharmaceuticals, pp. 1-50, (Catalog—Jan. 2000).
Shearwater Corporation, Polyethylene Glycol and Derivatives for Biomedical Applications, 20 pages, (Catalog—Jul. 2001).
Bonora, et al., "Synthesis by High-Efficiency Liquid-Phase (HELP) Method of Oligonucleotides Conjugated with High-Molecular Weight Polyethylene Glycols (PEGs)", Biological Procedures Online, vol. 1, No. 1, pp. 59-69, (May 14, 1998).
Fukushima, et al., "PEGylated Polyplex Micelles from Triblock Catiomers with Spatially Ordered Layering of Condensed pDNA and Buffering Units for Enhanced Intracellular Gene Delivery", J. Am. Chem. Soc., vol. 127, pp. 2810-2811, (2005).
Husseini, et al., "Ultrasonic release of doxorubicin from Pluronic P105 micelles stabilized with an interpenetrating network of N,N-diethylacrylamide," J. of Control Rel., vol. 83, pp. 303-305, (2002).
Kim, et al., "PEG conjugated VEGF siRNA for anti-angiogenic gene therapy", Journal of Controlled Release, vol. 116, pp. 123-129, (2006).
Kim, et al., "LHRH Receptor-Mediate Delivery of siRNA Using Polyelectrolyte Complex Micelles Self-Assembled from siRNA-PEG-LHRH Conjugate and PEI", Bioconjugate Chem., vol. 19, pp. 2156-2162, (2008).
Oishi, et al., "Lactosylated Poly(ethylene glycol)-siRNA Conjugate through Acid-Labile β-Thiopropionate Linkage to Construct pH-Sensitive Polyion Complex . . . ", J. Am. Chem. Soc., vol. 127, pp. 1624-1625, (2005).
Petrie, et al., "An Improved CPG Support for the Synthesis of 3'-Amine-Tailed Oligonucleotides", Bioconjugate Chem., vol. 3, pp. 85-87, (1992).
Sims, et al., "A Method for the Estimation of Polyethylene Glycol in Plasma Protein Fractions", Analytical Biochemistry, vol. 107, pp. 60-63, (1980).
PCT International Search Report and Written Opinion corresponding to PCT Application No. PCT/US2009/004747 date of mailing Feb. 8, 2010.
PCT International Preliminary Report on Patentability corresponding to PCT Application No. PCT/US2009/004747 date of mailing Mar. 3, 2011.
Calvo, et al., Novel Hydrophilic Chitosan-Polyethylene Oxide Nanoparticles as Protein Carriers, Journal of Applied Polymer Science, vol. 63, pp. 125-132, (1997).
Communication corresponding to European Application No. 09 789 178.2-1216 dated Nov. 17, 2011.

* cited by examiner

COMPLEXES OF SMALL-INTERFERING NUCLEIC ACIDS

CROSS-REFERENCED TO RELATED APPLICATIONS

This application is a 35 U.S.C. §371 application of International Application No. PCT/US2009/004744, filed Aug. 19, 2009, designating the United States, which claims the benefit of priority under 35 U.S.C. §119(e) to: Provisional Patent Application No. 61/189,528, filed Aug. 19, 2008; Provisional Patent Application No. 61/198,935, filed Nov. 12, 2008; and Provisional Application No. 61/153,636, filed Feb. 18, 2009; all of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Mar. 31, 2011, is named SHE0267.txt and is 91,754 bytes in size.

FIELD OF THE INVENTION

Among other things, one or more embodiments of the present invention relate generally to complexes comprising a small interfering nucleic acid (siNA) and a polymer. In addition, the invention relates to (among other things) compositions comprising complexes, methods for synthesizing complexes, and methods of administering a composition.

BACKGROUND OF THE INVENTION

RNA interference is currently recognized as a highly specific mechanism of sequence-specific gene silencing. See deFougerolles et al. (2007) *Nature Reviews* 6:443-453. The mechanism allows for the specific and profound reduction of proteins and mRNA.

Briefly, double-stranded RNA (dsRNA) is synthesized with a sequence complementary to a gene of interest and introduced into a cell or organism, where the dsRNA is recognized as exogenous genetic material and activates the RNAi pathway. If the exogenous dsRNA is relatively long, it will be cleaved into small interfering RNAs (siRNAs). Alternatively, if the exogenous dsRNA is relatively short (about 30 base pairs or less), cleavage does not occur, the exogenous dsRNA itself acts as the siRNA substrate, and complications arising from activation of innate immunity defenses are avoided. In both cases, the siRNA becomes incorporated into an RNA-induced silencing complex (RISC) followed by unwinding of the double stranded siRNA into two strands. One of these strands, the "sense" strand (also known as the "passenger" strand), is discarded. The other strand, the "guide" strand (also known as the "antisense" strand) recognizes target sites to direct mRNA cleavage, thereby silencing its message. A similar RNAi mechanism involves microRNAs (miRNAs) deriving from imperfectly paired non-coding hairpin RNA structures.

Through the specific targeting of genes, RNAi-based therapies have the ability to substantially block the production of undesired proteins. Thus, in diseases and conditions attributable to the undesired or over expression of certain proteins, RNAi-based therapies represent a potentially powerful and important approach.

Despite the great promise of RNAi-based therapies, there remains a problem of the relative short half life of these therapeutics in vivo. There remains a need for better and improved versions of siNA in order to bring the RNAi-based therapies to fruition.

SUMMARY OF THE INVENTION

Accordingly, in one or more embodiments of the invention, a complex is provided, the complex comprising a siNA complexed with a chitosan, wherein the chitosan is optionally attached, either directly or through one or more atoms, to a water-soluble polymer.

In one or more embodiments of the invention, a complex is provided, the complex comprising a siNA complexed with a chitosan, wherein (i) optionally, the chitosan is attached, either directly or through one or more atoms, to a water-soluble polymer, which following administration, is optionally released, and (ii) optionally, the siNA is in the form of a siNA attached, either directly or through one or more atoms, to a water-soluble polymer.

In one or more embodiments of the invention, a complex is provided, the complex comprising a siNA complexed with a chitosan, wherein (i) optionally, the chitosan is attached, either directly or through one or more atoms, to a water-soluble polymer, which following administration, is optionally released, and (ii) optionally, the chitosan is attached, either directly or through one or more atoms, to a targeting moiety (also referred to as a "targeting group," and (iii) optionally, the siNA is in the form of a siNA attached, either directly or through one or more atoms, to a water-soluble polymer (i.e., a conjugate of a siNA and a water-soluble polymer).

In one or more embodiments of the invention, a composition is provided, the composition comprising a complex of a siNA complexed with a chitosan, wherein the chitosan is optionally attached, either directly or through one or more atoms, to a water-soluble polymer.

In one or more embodiments of the invention, a complex is provided, the complex comprising a siNA complexed with a chitosan, wherein (i) optionally, the chitosan is attached, either directly or through one or more atoms, to a water-soluble polymer, which following administration, is optionally released, and (ii) optionally, the chitosan is attached, either directly or through one or more atoms, to a targeting moiety (also referred to as a "targeting group") and (iii) optionally, the siNA is in the form of a siNA attached, either directly or through one or more atoms, to a water-soluble polymer (i.e., a conjugate of a siNA and a water-soluble polymer).

In one or more embodiments of the invention, a composition is provided, the composition comprising (a) a complex of a siNA complexed with a chitosan, wherein (i) optionally, the chitosan is attached, either directly or through one or more atoms, to a water-soluble polymer, which following administration is optionally released, (ii) optionally, the chitosan is attached, either directly or through one or more atoms, to a targeting moiety (also referred to as a "targeting group") and (b) optionally, a transfection agent (e.g., a lipid, including, without limitation, lipids sold under the LIPOFECTAMINE™ 2000 brand (Life Technologies, Carlsbad Calif.]. In one or more embodiments, the transfection agent can simply be part of the composition without being covalently attached to any part of the complex. In one or more embodiments, the transfection agent can be covalently attached, either directly or through one or more atoms, to a component of the complex (such as the chitosan component of the complex, and/or, when present, the water-soluble polymer component of the complex).

In one or more embodiments of the invention, when one component is "attached through one or more atoms" the "one or more atoms" can be a divalent water-soluble polymer, such as a poly(ethylene oxide) having a molecular weight of about 20,000 Daltons.

In one or more embodiments of the invention, a method for delivering a complex is provided, the method comprising the step of subcutaneously administering to the patient a composition comprised of a complex comprising a siNA complexed with a chitosan, wherein the chitosan is optionally attached, either directly or through one or more atoms, to a water-soluble polymer.

```
Oligo3 (SEQ ID NO: 186):
5'(C6-S-SC6)-
AmCAmACmAGmACmUUmUAmAUmGUmAA-3' (bar3), Oligo5 (SEQ ID NO: 187):
5'(C6-NH2)AmCAmACmAGmACmUUmUAmAUmGUmAA-3'(C6-NH2)
(bar4), Oligo28 (SEQ ID NO: 188):
5'mUUmACmAUmUAmAAmGUmCUmGUmUGmU-3' (C6-NH)
(Cy5.5) (bar5), Oligo31 (SEQ ID NO: 189):
5'mUUmACmAUmUAmAAmGUmCUmGUmUGmU-3' (C6-NH2)
(bar6), Oligo34 (SEQ ID NO: 190):
5'mUUmACmAUmUAmAAmGUmCUmGUmUGmU-3' C3-S-S-C3
(bar7).
```

Figure 33:
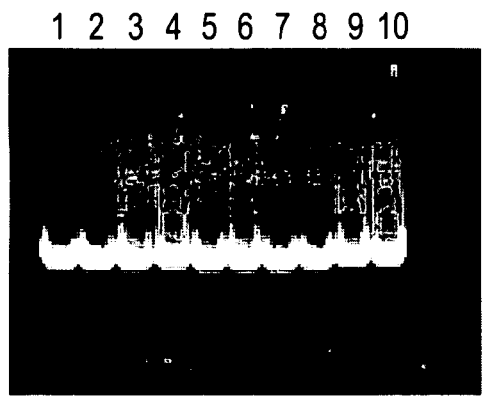
Figure 34:
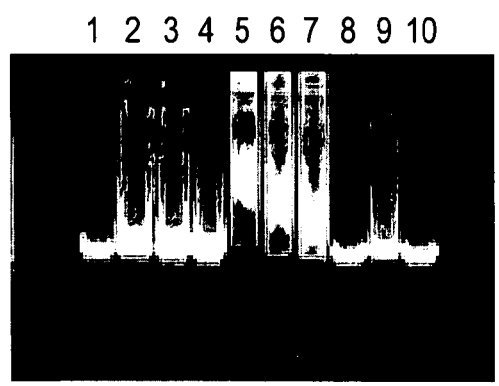

FIG. 33 and FIG. 34 are representations of gels as further described in Example 35.

DETAILED DESCRIPTION OF THE INVENTION

As used herein, the singular forms "a," "an," and "the" include the plural reference unless the context clearly dictates otherwise. Thus, for example, reference to "siNA" includes a single siNA as well as two or more of the same or different siNAs, reference to an excipient refers to a single excipient as well as two or more of the same or different excipients, and the like.

Before further discussion, a definition of the following terms will aid in the understanding of the present invention.

In describing and claiming one or more embodiments of the present invention, the following terminology will be used in accordance with the definitions described below.

"PEG," "polyethylene glycol" and "poly(ethylene glycol)" as used herein, are interchangeable and encompass any non-peptidic water-soluble poly(ethylene oxide). Typically, PEGs for use in accordance with the invention comprise the following structure "—(OCH$_2$CH$_2$)$_n$—" where (n) is 2 to 4000. As used herein, PEG also includes "—CH$_2$CH$_2$—O (CH$_2$CH$_2$O)$_n$—CH$_2$CH$_2$-" and "—(OCH$_2$CH$_2$)$_n$O—," depending upon whether or not the terminal oxygens have been displaced. Throughout the specification and claims, it should be remembered that the term "PEG" includes structures having various terminal or "end capping" groups and so forth. The term "PEG" also means a polymer that contains a majority, that is to say, greater than 50%, of —OCH$_2$CH$_2$— repeating subunits. With respect to specific forms, the PEG can take any number of a variety of molecular weights, as well as structures or geometries such as "branched," "linear," "forked," "multifunctional," and the like, to be described in greater detail below.

The terms "end-capped" and "terminally capped" are interchangeably used herein to refer to a terminal or endpoint of a polymer having an end-capping moiety. Typically, although not necessarily, the end-capping moiety comprises a hydroxy or C$_{1-20}$ alkoxy group, more preferably a C$_{1-10}$ alkoxy group, and still more preferably a C$_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in CH$_3$—O—(CH$_2$CH$_2$O)$_n$— and CH$_3$(OCH$_2$CH$_2$)$_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

The term "targeting moiety" is used herein to refer to a molecular structure that increases localization of the complex described herein to a targeted area, e.g., enter, permeate, or penetrate a cell, or bind a receptor. Preferably, the targeting moiety comprises of vitamin, cofactor, antibody, antigen, receptor, DNA, RNA, sialyl Lewis X antigen, hyaluronic acid, sugars, cell specific lectins, steroid or steroid derivative, RGD peptide, cell penetrating or cell targeting moiety, ligand for a cell surface receptor, serum component, or combinatorial molecule directed against various intra- or extracellular receptors. The targeting moiety may also comprise a lipid or a phospholipid. Exemplary phospholipids include, without limitation, phosphatidylcholines, phospatidylserine, phospatidylinositol, phospatidylglycerol, and phospatidylethanolamine. These lipids may be in the form of micelles or liposomes and the like. The targeting moiety may further comprise a detectable label or alternately a detectable label may serve as a targeting moiety. When the complex has a targeting group comprising a detectable label, the amount and/or distribution/location of the polymer and/or the moiety (e.g., active agent) to which the polymer is coupled can be determined by using a suitable detector. Such labels include, without limitation, fluorescers, chemiluminescers, moieties used in enzyme labeling, colorimetric (e.g., dyes), metal ions, radioactive moieties, gold particles, quantum dots, and the like.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight in the context of a water-soluble polymer, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-point depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "spacer moiety," "linkage" and "linker" are used herein to refer to an atom or a collection of atoms optionally used to link interconnecting moieties such as a terminus of a polymer segment and a siNA or an electrophile or nucleophile of a siNA. The spacer moiety may be hydrolytically stable or may include a physiologically releasable linkage (e.g., a hydrolyzable or enzymatically releasable linkage). Unless the context clearly dictates otherwise, a spacer moiety optionally exists between any two elements of a compound (e.g., the chitosan and a water-soluble polymer or the residue of a siNA and a water-soluble polymer can each be attached directly or indirectly through a spacer moiety).

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 3-methylpentyl, and the like. As used herein, "alkyl" includes cycloalkyl as well as cycloalkylene-containing alkyl.

Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

An "organic radical" as used herein shall include alkyl, substituted alkyl, aryl, substituted aryl, "Electrophile" and "electrophilic group" refer to an ion or atom or collection of atoms, that may be ionic, having an electrophilic center, i.e., a center that is electron seeking, capable of reacting with a nucleophile.

"Nucleophile" and "nucleophilic group" refers to an ion or atom or collection of atoms that may be ionic having a nucleophilic center, i.e., a center that is seeking an electrophilic center or with an electrophile.

A "physiologically cleavable" or "releasable" bond is a bond within a single molecular species that cleaves to result in two distinct molecular species. An exemplary releasable bond is a hydrolysable bond, which reacts with water (i.e., is hydrolyzed) under physiological conditions. The tendency of a bond to hydrolyze in water will depend not only on the general type of linkage connecting two central atoms but also on the substituents attached to these central atoms.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of a chitosan-siNA complex that is needed to provide a desired level of the complex (or siNA) in the bloodstream or in the target tissue. The precise amount will depend upon numerous factors, e.g., the particular siNA, the components and physical characteristics of the therapeutic composition, intended patient population, individual patient considerations, and the like, and can readily be determined by one skilled in the art, based upon the information provided herein.

"Multi-functional" means a polymer having three or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

The term "siNA," as used herein, refers to a moiety having human siNA activity. The siNA will also have at least one electrophilic group or nucleophilic group suitable for reaction with a polymeric reagent. In addition, the term "siNA" encompasses both the siNA prior to conjugation as well as the siNA residue following conjugation. As will be explained in further detail below, one of ordinary skill in the art can determine whether any given moiety has siNA activity. Further, the term "siNA" includes any nucleic acid molecule capable of mediating RNA interference ("RNAi") or gene silencing. The siNA includes, without limitation, a "short interfering nucleic acid" and includes short interfering RNA (siRNA), double-stranded RNA (dsRNA), micro-RNA (miRNA), short hairpin RNA (shRNA), short interfering oligonucleotide, short interfering nucleic acid, short interfering modified oligonucleotide, chemically-modified siRNA, and post-transcriptional gene silencing RNA (ptgsRNA). For example, the siRNA can be a double-stranded oligonucleotide molecule comprising a sense oligonucleotide and an antisense oligonucleotide, wherein the antisense region comprises complementarity to a target nucleic acid molecule. The siRNA can be a single-stranded hairpin oligonucleotide having self-complementary sense and antisense regions, wherein the antisense region comprises complementarity to a target nucleic acid molecule.

As used herein, siRNA molecules need not be limited to those molecules containing only RNA, but further encompasses chemically-modified nucleotides and non-nucleotides. In certain embodiments, the short interfering nucleic acid molecules of the invention lack 2'-hydroxy(2'-OH) containing nucleotides. In certain embodiments, short interfering nucleic acids do not require the presence of nucleotides having a 2'-hydroxy group for mediating RNAi and as such, short interfering nucleic acid molecules of the invention optionally do not contain any ribonucleotides (e.g., nucleotides having a 2'-OH group). The microRNAs can be of an agonist or antagonist and including, for example, antagomirs (as described in Krützfeldt et al. (2005) Nature 438(7068): 685-689). The siNA can be single stranded, double stranded or triple stranded.

In some instances, the siNA can be a sequence listed in the SEQUENCE LISTING included herewith.

In some instances, the siNA comprises a first sequence, for example, the antisense sequence of the siNA construct, complementary to a sequence or portion of sequence comprising a sequence represented by GenBank Accession Nos. shown in Table I of U.S. Patent Application Publication No. 2007/0160980 A1, or other sequence listed in that publication.

Further exemplary siNA is a siNA described in one or more of WO07/121,947, WO07/121,956, WO07/084,684, WO06/069782, WO06/023544, WO05/105152, WO05/000320, WO04/035615, European Patent and/or Application Nos. EP1857547, EP1771206, EP1527176, EP1638580, EP1551868, EP1536827, EP1527176, U.S. Patent Application Publication Nos. 2004/0180351 and 2005/0043263.

Still further exemplary siNA is siNA described in one or more of U.S. Pat. Nos. 5,898,031, 6,107,094, 7,056,704, 7,078,196, European Patent and Application Nos. EP1144623, EP1214945, EP1352061, German Patent 20023125, and U.S. Patent Application Publication Nos. 2005/0176667, 2005/0186591, 2005/0288244, 2006/0008822, 2006/0035254, 2006/0287260, 2007/0054279, 2007/0161595, 2007/0185050, 2007/0197460, 2007/0213292, 2007/0275465 and 2008/0194512.

Still further exemplary siNA is siNA described in one or more of the following U.S. Patent Application Publication Nos. 2005/0244858, 2005/0277610 and 2007/0265220.

Still further exemplary siNA is siNA described in one or more of the following publications Rose et al. (2005) Nucleic Acid Res. 33(13):4140-4156, Kim et al. (2005) Nat Biotechnol. 23(2):222-226 and Amarzguioui et al. (2006) Nature Protocol 1(2):508-517.

Still further exemplary siNA is siNA described in one or more of the following U.S. Patent Application Publication Nos. 2002/0086356, 2003/0108923, 2007/0229266, 2004/0259247, 2004/0259248, 2005/0026278, 2005/0059005, 2005/0182005, 2005/0227934, 2005/0234006, 2005/0234007, 2006/0166910, 2006/0212950, 2007/0003960, 2007/0003961, 2007/0003962, 2007/0003963, 2007/0093445 and 2007/0287179.

Still further exemplary siNA is siNA described in one or more of the following U.S. Patent Application Publication Nos. 2003/0190654, 2004/0001811, 2004/0038921, 2004/0053875, 2004/0072779, 2004/0091457, 2004/0102408, 2004/0121348, 2004/0126791, 2004/0175703, 2005/0074757, 2005/0100907 and 2008/0070856.

Still further exemplary siNA is siNA described in one or more of the following U.S. Patent Application Publication Nos. 2006/0014289, 2006/0035815, 2006/0122137, 2006/0142230, 2006/0160123, 2007/0155658, 2007/0172430, 2007/0213257, 2007/0213293, 2007/0254362, 2007/0269892, 2007/0275923, 2007/0276134, 2007/0281900, 2007/0293449, 2007/0293657 and 2008/0076701.

In one or more embodiments, the siNA is in the form of a siNA conjugated to a water-soluble polymer. Examples of siNA in the form of a siNA conjugated to a water-soluble polymer are described in By "inhibit" or "down regulate" it is meant that the activity of a gene expression product or level of RNAs or equivalent RNAs encoding one or more gene products is reduced below that observed in the absence of the nucleic acid molecule. In one embodiment, inhibition with a siRNA molecule preferably is below that level observed in the presence of an inactive or attenuated molecule that is unable to mediate an RNAi response. In another embodiment, inhibition of gene expression with the siRNA molecule included as part of the instant invention is greater in the presence of the siRNA molecule than in its absence.

By "RNA" is meant a molecule comprising at least one ribonucleotide residue. By "ribonucleotide" is meant a nucleotide with a hydroxyl group at the 2' position of a β-D-ribofuranose moiety. The terms include triple-stranded RNA, double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of a siRNA or internally (e.g. capped structures), for example, at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "gene" and "target gene" and "target nucleic acid" is meant, a nucleic acid that encodes an RNA, for example, nucleic acid sequences including, but not limited to, structural genes encoding a polypeptide. The target gene can be a gene derived from a cell, an endogenous gene, a transgene, or exogenous genes such as genes of a pathogen, for example a virus, which is present in the cell after infection thereof. The cell containing the target gene can be derived from or contained in any organism, for example a plant, animal, protozoan, virus, bacterium, or fungus.

"Optional" and "optionally" means that the subsequently described circumstance may or may not occur, so that the description includes instances where the circumstance occurs and instances where it does not. Thus, for example, a composition comprising an "optional excipient" includes compositions comprising one or more excipient as well as compositions any excipient.

The term "patient," refers to a living organism suffering from or prone to a condition that can be prevented or treated by administration of an active agent (e.g., a chitosan-siNA complex), and includes both humans and animals. The term "subject" refers to a living organism suffering from or prone to a condition that can be prevented or treated through RNAi.

"Optional" or "optionally" means that the subsequently described circumstance may or may not occur, so that the description includes instances where the circumstance occurs and instances where it does not.

As used herein, an "excipient" is a component of a pharmaceutical composition that does not have RNAi activity. Further, "excipients" such as buffers, sugars, amino acids, and so forth are intended components of a pharmaceutical composition and stand in contrast to unintended components of a composition such as impurities.

A "therapeutically effective amount" is an amount of siNA (e.g., sirNA) construct required to provide a desired therapeutic effect. The exact amount required will vary from subject to subject and will otherwise be influenced by a number of factors, as will be explained in further detail below. An appropriate "therapeutically effective amount," however, in any individual case can be determined by one of ordinary skill in the art.

The term "substantially" refers to a system in which greater than 50% of the stated condition is satisfied. For instance, greater than 85%, greater than 92%, or greater than 96% of the condition may be satisfied.

By "complex" is meant a substance formed from a high affinity interaction between a chitosan and a siNA, based upon non-covalent binding. Typically, the high affinity interaction is achieved by ionic bonds. In some instances, the high affinity interaction is can be brought about wholly or in part by hydrogen bonding, Van der Walls interactions or other non-covalently binding attractions.

Turning to one or more embodiments of the invention, a complex is provided, the complex comprising a residue of siNA complexed with covalently attached (either directly or through a spacer moiety) to a water-soluble polymer. The complexes of the invention will have one or more of the following features.

siNAs

Turning to exemplary aspects of the invention, the compositions include one or more siNA, which may take several forms. siNAs may be of a length of about 7 to 50 nucleotides (each strand of a single stranded, double stranded and triple stranded siNA is independently of from about 7 to 50 nucleotides in length), e.g., one of the following nucleotide lengths: 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50. In some instances, the nucleotide length satisfies one or more of the following ranges: from 10 to 30; from 15 to 25; from 15 to 30; from 26 to 28; from 15 to 26; from 27 to 50; from 27 to 30; and from 10 to 20. Many siNAs are known in the art. siNAs, particularly in their single-stranded form and individual strands of a double-stranded or triple stranded siNA, generally have the ability to bind to a target with a $K_D$ of about 0.1 nM to about 100 nM.

In one or more embodiments, the siNA is a siRNA comprising a double-stranded structure whereby the double-stranded structure comprises a first strand and a second strand, whereby the first strand comprises a first stretch of contiguous nucleotides and whereby said first stretch is at least partially complementary to a target nucleic acid, and the second strand comprises a second stretch of contiguous nucleotides, whereby said second stretch is at least partially identical to a target nucleic acid, and, optionally, one or more of the following apply: (i) the first stretch and/or the second stretch have a length of 15 to 23 nucleotides (e.g., 15, 16, 17, 18, 19, 20, 21 or 23 nucleotides); (ii) at least one of the two strands has an overhang of at least one nucleotide at the 5'-end or the 3'-end (preferably consisting of at least one nucleotide which is selected from the group comprising ribonucleotides and desoxyribonucleotides); (iii) a 2' modification (preferably selected from the group comprising amino, fluoro, methoxy, alkoxy and alkyl modifications; (iv) a 3' modification (preferably an inverted nucleotide); (v) said first strand and/or said second strand comprises a plurality of groups of modified nucleotides having a modification at the 2'-position whereby within the strand each group of modified nucleotides is flanked on one or both sides by a flanking group of nucleotides whereby the flanking nucleotides forming the flanking group of nucleotides is either an unmodified nucleotide or a nucleotide having a modification different from the modification of the modified nucleotides; (vi) the first strand and the target nucleic acid comprises at least 15 nucleotides wherein there is one mismatch or two mismatches between said first strand and the target nucleic acid forming said double-stranded structure; (vii) the first strand and the second strand are linked by a loop structure. In some instances, it is preferred that the double-stranded structure is blunt ended on both sides of a double-stranded structure. In other instances, it is preferred that the double-stranded structure is blunt ended on the double-stranded structure which is defined by the 5'-end of the first strand and the 3'-end of the second strand. In still other instances, it is preferred that the double-stranded structure is blunt ended on the double stranded structure which is defined by the 3'-end of the first strand and the 5'-end of the second strand.

In one or more embodiments of the invention, the modification(s) included within an oligonucleotide that is an siNA can be present such that a pattern of the modification(s) is apparent or can be present such that a pattern of the modification(s) is not apparent. As would be understood, it is not possible to understand whether a pattern of modification(s) within an oligonucleotide is present based on only modification(s) of a single nucleotide within the oligonucleotide; consequently, it is necessary to demonstrate any pattern within a stretch of oligonucleotides.

This discussion of a pattern (and lack of a pattern) of modifications will focus on a modified nucleotide wherein a methoxy group is formed via methylation of the 2'-OH-group of the ribose moiety of the nucleotide (i.e., a 2'-O-methyl modification); this disclosure relating to patterns (or lack of patterns) of modifications, however, applies to any given modification as in the context of discussing the pattern (or lack of the pattern), any modification can be substituted for 2'-O-methyl modification).

In one or more embodiments, a pattern arises within a stretch of oligonucleotides such that each nucleotide within a stretch of nucleotides within the siNA alternates between 2'-O-methyl modified and non-2'-O-methyl modified. In one or more embodiments, however, a stretch of oligonucleotides will not demonstrate a pattern wherein a stretch of nucleotides within the siNA alternates between 2'-O-methyl modified and non-2'-O-methyl modified nucleotides. In an convention wherein "M" is a 2'-O-methyl modified nucleotide and "O" is a non-2'-O-methyl modified nucleotide, the following arrangement is considered as exhibiting a pattern: MOMO-MOMOM, while the following arrangements are considered as not exhibiting a pattern: MOOOMOMOM; MOMOOO-MOM; MOMOMOMOO; MOOOOOMOM; MOMOOOOOO; MOOOOOMOM; MOMOOOOO; MMOMMOMMO; MOOMMOMMO; MOMOOOMMO; MOMOMOOOM; MMMOMOMOM; MOMMMOMOM; MOMOMMMOM; MOMOMOMMO; MOMOMOMOO; MMMOOMOMO; MMMOOOMOM; MMMOOOOMO; MMMOOOOOM; MMOOOMMOO; MMOMOMMOM; MMMMOMMMM; MMOMMMOMM; MOMMOM-MMO; MOMOMMOMM; MOMOMMMOO; MOMOM-MMOM; MOOMOOOMM; MOMOOMMMO; MOMOOOMOM; MMOOOMMM; MOOOMMOMO; MMMMMMOMM; MOMMMMMOM; OOMOMOMOM; OOOOMOMOM; OOMOOOMOM; OOMOMOMOO; OOOOOOMOM; OOMOOOOOO; OOOOOOMOM; OOMOOOOOO; OMOMMOMMO; OOOMMOMMO; OOMOOOMMO; OOMOMOOOM; OMMOMOMOM;

OOMMMOMOM; OOMOMMMOM; OOMOMOMMO; OOMOMOMOO; OMMOOMOMO; OMMOOOMOM; OMMOOOOMO; OMMOOOOOM; OMOOOMMOO; OMOMOMMOM; OMMMOMMMM; OMOMMMOMM; OOMMOMMMO; OOMOMMMOMM; OOMOMMMOO; OOMOMMMOM; OOOMOOOMM; OOMOOMMMO; OOMOOOOMM; OMOOOMOMM; OOOOMMOMO; OMMMMMOMM; and OOMMMMMOM. Of course, other arrangements are possible that similarly do not evidence a pattern. In another embodiment, the modified nucleotide comprises a 2'-fluoro modification.

The siNA is preferably targeted against a gene (i.e., the "target gene" or "target nucleic acid") selected from the group comprising structural genes, housekeeping genes, transcription factors, motility factors, cell cycle factors, cell cycle inhibitors, enzymes, growth factors, cytokines and tumor suppressors.

In one or more embodiments, the siNA may be covalently attached, either directly or through one or more atoms, to a water-soluble polymer, which optionally may have a bond connecting the water-soluble polymer to the siNA and/or a bond within the water-soluble polymer itself that is degradable, that is, a bond that undergoes cleavage in vivo caused by either acid or basic catalysis or through an enzymatic process.

siNA may be purchased from a commercial source or may be synthetically produced. For example siRNA can be purchased from Applied Biosystems (Foster City, Calif.) and Thermo Fisher Scientific Inc. (Waltham, Mass.). Those of ordinary skill in the art can prepare synthetic versions of siNA based on the references cited herein and elsewhere in the literature. For further details and a discussion of the synthesis of siRNA molecules in general see, U.S. Patent Application Publication No. 2003/0206887.

The Chitosan

As used herein, chitosan is understood to include not only chitin, which are linear polysaccharides comprised of 1-4 linked 2-amino-2-deoxy-β-D-glucose (GlcN) and the N-acetylated analogue 2-acetamido-2-deoxy-β-D-glucose (GlcNAc) monomers, but chitosan as well, which are the deacetylated versions of chitin. The chitin typically available is largely deacetylated but still has some chitin (acetylated) segments as well as chitosan (deacetylated) segments. The amine groups in the chitosan have a pKA of about 6.5, thereby generally resulting in a polycationic polymer under neutral conditions. With respect to the present invention, it is preferred that the chitosan used to form the complexes described herein is in the form of a polycationic polymer.

Chitosan also includes methylated chitosan (where the amino group has been mono-, di- or trimethylated).

Typically, the weight-average molecular weight of the chitosan is from about 500 Daltons to about 100,000 Daltons. Exemplary ranges, however, include weight-average molecular weights in the range of greater than 500 Daltons to about 90,000 Daltons, in the range of from about 600 Daltons to about 80,000 Daltons, in the range of from about 700 Daltons to about 70,000 Daltons, in the range of greater than 800 Daltons to about 50,000 Daltons, in the range of from about 900 Daltons to about 25,000 Daltons, in the range of from about 1,000 Daltons to about 22,000 Daltons, in the range of from about 1,000 Daltons to about 20,000 Daltons, in the range of from about 1,000 Daltons to about 15,000 Daltons, in the range of from about 2,000 Daltons to about 12,000 Daltons, in the range of from about 2,000 Daltons to about 5,000 Daltons, in the range of from about 6,000 Daltons to about 12,000 Daltons, and in the range of from about 2,000 Daltons to about 10,000 Daltons. For any given water-soluble polymer, PEGs having a molecular weight in one or more of these ranges are preferred.

Typically, the percent deacetylation of the raw material chitosan (percent free amine groups) is from about 50% to about 100%. Exemplary ranges, however, include deacetylation percentages in the range of 55% to about 98%, in the range of 65% to about 93%, and in the range of 74% to about 86%.

Complex Formation

The complexes of the invention are prepared by mixing the siNA with the chitosan. By "mixing" is meant a combining or physical mixture of substances, typically followed by the application of energy to the system, such as stirring or agitating. In one approach, the siNA is added by mixing to a chitosan. In another approach, the chitosan is added by mixing to a siNA.

Chitosan-Water-Soluble Polymer

As previously discussed, in one or more embodiments, the chitosan optionally will be in the form of a chitosan attached, either directly or through one or more atoms, to a water-soluble polymer. In some embodiments, the water-soluble polymer may be attached to multiple sites on the chitosan to give mono-, di-, tri-, and even polysubstituted chitosan. Also, in some embodiments, the water soluble polymer is bonded to the chitosan employing a bond that is degradable, that is using a bond that undergoes cleavage in vivo caused by either acid or basic catalysis or through an enzymatic process. With respect to the water-soluble polymer, the water-soluble polymer is nonpeptidic, nontoxic, non-naturally occurring and biocompatible. With respect to biocompatibility, a substance is considered biocompatible if the beneficial effects associated with use of the substance alone or with another substance (e.g., an active agent such as an siNA) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the nonpeptidic water-soluble polymer is biocompatible and nonimmunogenic.

Further, the polymer is typically characterized as having from 2 to about 300 termini. Examples of such polymers include, but are not limited to, poly(alkylene glycols) such as polyethylene glycol ("PEG"), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(α-hydroxy acid), poly(vinyl alcohol), polyphosphazene, polyoxazoline, poly(N-acryloylmorpholine), hydroxyalkyl starch, and combinations of any of the foregoing.

With respect to hydroxyalkyl starch (HAS), these sugars represent a water-soluble polymer useful for the present invention. Typical of HAS is hydroxethyl starch, which is a substituted derivative of the carbohydrate polymer amylopectin which occurs in maize starch in a concentration of up to 95%. Amylopectin consists of glucose units, wherein the main chains have α-1,4-glycosidic bonds, but α-1,6-glycosidic bonds are present at the branching sites. Methods for activating hydroxyalkyl starch (such as hydroxyethyl starch) for facile attachment to molecules are described in U.S. Patent Application Publication No. 2006/0188472.

The polymer is not limited to a particular structure and can be linear (e.g., alkoxy PEG or bifunctional PEG), branched or multi-armed (e.g., forked PEG or PEG attached to a polyol core), dendritic, or with degradable linkages. Moreover, the internal structure of the polymer can be organized in any number of different patterns and can be selected from the group consisting of homopolymer, alternating copolymer, random copolymer, block copolymer, alternating tripolymer, random tripolymer, and block tripolymer.

Typically, activated PEG and other activated water-soluble polymers (i.e., polymeric reagents) are activated with a suitable activating group appropriate for coupling to a desired site on the siNA. Thus, a polymeric reagent will possess a reactive group for reaction with the siNA. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenum Press, New York (1992), and in Zalipsky (1995) *Advanced Drug Reviews* 16:157-182.

Typically, the weight-average molecular weight of the water-soluble polymer in the conjugate is from about 100 Daltons to about 150,000 Daltons. Exemplary ranges, however, include weight-average molecular weights in the range of greater than 5,000 Daltons to about 100,000 Daltons, in the range of from about 6,000 Daltons to about 90,000 Daltons, in the range of from about 10,000 Daltons to about 85,000 Daltons, in the range of greater than 10,000 Daltons to about 85,000 Daltons, in the range of from about 20,000 Daltons to about 85,000 Daltons, in the range of from about 53,000 Daltons to about 85,000 Daltons, in the range of from about 25,000 Daltons to about 120,000 Daltons, in the range of from about 29,000 Daltons to about 120,000 Daltons, in the range of from about 35,000 Daltons to about 120,000 Daltons, and in the range of from about 40,000 Daltons to about 120,000 Daltons. For any given water-soluble polymer, PEGs having a molecular weight in one or more of these ranges are preferred.

Exemplary weight-average molecular weights for the water-soluble polymer include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 1,500 Daltons, about 2,000 Daltons, about 2,200 Daltons, about 2,500 Daltons, about 3,000 Daltons, about 4,000 Daltons, about 4,400 Daltons, about 4,500 Daltons, about 5,000 Daltons, about 5,500 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched versions of the water-soluble polymer (e.g., a branched 40,000 Dalton water-soluble polymer comprised of two 20,000 Dalton polymers) having a total molecular weight of any of the foregoing can also be used. In one or more embodiments, the conjugate will not have any PEG moieties attached, either directly or indirectly, with a PEG having a weight average molecular weight of less than about 6,000 Daltons.

When used as the polymer, PEGs will typically comprise a number of (OCH$_2$CH$_2$) monomers [or (CH$_2$CH$_2$O) monomers, depending on how the PEG is defined]. As used throughout the description, the number of repeating units is identified by the subscript "n" in "(OCH$_2$CH$_2$)$_n$." Thus, the value of (n) typically falls within one or more of the following ranges: from 2 to about 3400, from about 100 to about 2300, from about 100 to about 2270, from about 136 to about 2050, from about 225 to about 1930, from about 450 to about 1930, from about 1200 to about 1930, from about 568 to about 2727, from about 660 to about 2730, from about 795 to about 2730, from about 795 to about 2730, from about 909 to about 2730, and from about 1,200 to about 1,900. For any given polymer in which the molecular weight is known, it is possible to determine the number of repeating units (i.e., "n") by dividing the total weight-average molecular weight of the polymer by the molecular weight of the repeating monomer.

One particularly preferred polymer is an end-capped polymer, that is, a polymer having at least one terminus capped with a relatively inert group, such as a lower C$_{1-6}$alkoxy group, although a hydroxyl group can also be used. When the polymer is PEG, for example, it is preferred to use a methoxy-PEG (commonly referred to as mPEG), which is a linear form of PEG wherein one terminus of the polymer is a methoxy (—OCH$_3$) group (or —CH$_3$, again depending on how the PEG is defined), while the other terminus is a hydroxyl or other functional group that can be optionally chemically modified.

In one form useful in one or more embodiments of the present invention, free or unbound PEG is a linear polymer terminated at each end with hydroxyl groups:

HO—CH$_2$CH$_2$O—(CH$_2$CH$_2$O)$_n$—CH$_2$CH$_2$—OH, wherein (n) typically ranges from zero to about 4,000.

The above polymer, alpha-, omega-dihydroxylpoly(ethylene glycol), can be represented in brief form as HO-PEG-OH where it is understood that the -PEG- symbol can represent the following structural unit:

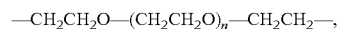

—CH$_2$CH$_2$O—(CH$_2$CH$_2$O)$_n$—CH$_2$CH$_2$—, wherein (n) is as defined as above.

In one or more embodiments, a heterobifunctional polymer is used to bond, either directly or through a series of atoms, first with siNA or chitosan and then at the remote terminus with some other moiety applicable to the invention, such as a targeting moiety. Thus, if PEG is the water-soluble polymer is such an embodiment then the following two structures represent possible configurations:

TG-O—CH$_2$CH$_2$O—(CH$_2$CH$_2$O)$_n$—CH$_2$CH$_2$—O-siNA, and

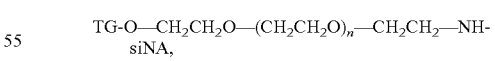

TG-O—CH$_2$CH$_2$O—(CH$_2$CH$_2$O)$_n$—CH$_2$CH$_2$—NH-siNA, wherein n is as defined above and may range from 1 to 1000 and TG is a targeting moiety.

Another type of PEG useful in one or more embodiments of the present invention is methoxy-PEG-OH, or mPEG in brief, in which one terminus is the relatively inert methoxy group, while the other terminus is a hydroxyl group. The structure of mPEG is given below:

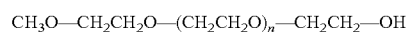

CH$_3$O—CH$_2$CH$_2$O—(CH$_2$CH$_2$O)$_n$—CH$_2$CH$_2$—OH wherein (n) is as described above.

Multi-armed or branched PEG molecules, such as those described in U.S. Pat. No. 5,932,462, can also be used as the PEG polymer. For example, PEG can have the structure:

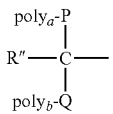

wherein:

poly$_a$ and poly$_b$ are PEG backbones (either the same or different), such as methoxy poly(ethylene glycol);

R" is a nonreactive moiety, such as H, methyl or a PEG backbone; and

P and Q are nonreactive linkages. In a preferred embodiment, the branched PEG polymer is methoxy poly(ethylene glycol) disubstituted lysine. Depending on the specific siNA used, the reactive ester functional group of the disubstituted lysine may be further modified to form a functional group suitable for reaction with the target group within the siNA.

In addition, the PEG can comprise a forked PEG. An example of a forked PEG is represented by the following structure:

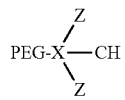

wherein: X is a spacer moiety of one or more atoms and each Z is an activated terminal group linked to CH by a chain of atoms of defined length. U.S. Pat. No. 7,223,803 discloses various forked PEG structures capable of use in one or more embodiments of the present invention. The chain of atoms linking the Z functional groups to the branching carbon atom serve as a tethering group and may comprise, for example, alkyl chains, ether chains, ester chains, amide chains and combinations thereof.

The PEG polymer may comprise a pendant PEG molecule having reactive groups, such as carboxyl, covalently attached along the length of the PEG rather than at the end of the PEG chain. The pendant reactive groups can be attached to the PEG directly or through a spacer moiety, such as an alkylene group.

In addition to the above-described forms of PEG, the polymer can also be prepared with one or more weak or degradable linkages (also referred to as "releasable" linkages") in the polymer, including any of the above-described polymers. For example, PEG can be prepared with ester linkages in the polymer that are subject to hydrolysis. As shown below, this hydrolysis results in cleavage of the polymer into fragments of lower molecular weight:

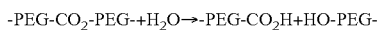

Other hydrolytically degradable linkages, useful as a degradable linkage within a polymer backbone, include: carbonate linkages; imine linkages resulting, for example, from reaction of an amine and an aldehyde (see, e.g., Ouchi et al. (1997) *Polymer Preprints* 38(1):582-3); phosphate ester linkages formed, for example, by reacting an alcohol with a phosphate group; hydrazone linkages which are typically formed by reaction of a hydrazide and an aldehyde; acetal linkages that are typically formed by reaction between an aldehyde and an alcohol; orthoester linkages that are, for example, formed by reaction between a formate and an alcohol; amide linkages formed by an amine group, e.g., at an end of a polymer such as PEG, and a carboxyl group of another PEG chain; urethane linkages formed from reaction of, e.g., a PEG with a terminal isocyanate group and a PEG alcohol; peptide linkages formed by an amine group, e.g., at an end of a polymer such as PEG, and a carboxyl group of a peptide; and oligonucleotide linkages formed by, for example, a phosphoramidite group, e.g., a phosphoramidite group introduced at the end of a polymer, and a 5' hydroxyl group of an oligonucleotide.

The water-soluble polymer associated with the chitosan can also be "releasable" (also referred to as "cleavable"). That is, the water-soluble polymer is released (either through hydrolysis, enzymatic processes, or otherwise). In some instances, releasable polymers detach from the chitosan in vivo without leaving any fragment of the water-soluble polymer or spacer moiety. In other instances, releaseable polymers detach from the chitosan in vivo leaving a relatively small fragment (e.g., a succinate tag) from the water-soluble polymer. An exemplary releasable polymer includes one that attaches to the chitosan via a carbonate linkage.

Those of ordinary skill in the art will recognize that the foregoing discussion concerning nonpeptidic and water-soluble polymers is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

As described above, optionally a water-soluble polymer is covalently attached to the chitosan. Typically, in such an instance, there will be 1, 2, 3, 4, 5, 6, 7, 8 or more water-soluble polymers covalently attached to the chitosan. ** IS THIS TRUE?

The particular linkage between the chitosan and water-soluble polymer depends on a number of factors. Such factors include, for example, the particular linkage chemistry employed, the particular polymer and chitosan, the available functional groups, and the like. Exemplary linkages include amide, urethane (also known as carbamate), amine, thioether (also known as sulfide), and urea (also known as carbamide).

In one or more embodiments, the complexes of the invention further comprise a targeting moiety. Targeting moiety may comprise of, but is not limited to, an antibody or a fragment of an antibody, a protein or a fragment thereof, a receptor or a subunit thereof, a peptide, a lipid, a carbohydrate, a polymer, a radiolabel, or other suitable targeting moiety. For example, an antibody to a cell surface receptor or the receptor's ligand may be used as a targeting moiety that would deliver the complex to cells expressing the receptor on its surface. Other examples of targeting moieties and their targets include: glucose or mannose-terminal glycoproteins for macrophages; galactose-terminal glycoproteins for hepatocytes; phosphovitellogenins for developing oocyte; fibrin for epithelial cells; and insulin and/or other hormones and transferring for various cell types. Once bound to a receptor or to the cell surface, the conjugates of the invention may be endocytosed, either by receptor-mediated endocytosis, pinocytosis, clathrin-mediated endocytosis, caveolae-mediated endocytosis, or some other mechanism. The endosomes (or commonly referred to as "vesicles"), containing the target-moiety-containing complex may fuse with other vesicles, such as lysozomes, phagosomes, storage vesicles, or uncoupling vesicles called the compartment of uncoupling receptor and ligand (CURL). CURLs are characterized by an internal pH of ~5.0. Eventually, these vesicles may fuse with other vesicles or dissolve and release their contents in the cytoplasm, thus delivering the siNA to the intended cell and its cytoplasm.

As noted previously, the siNA can be in the form of a conjugate of siNA. Conjugates of siNA are described herein and in McManus et al., copending international patent application PCT/US09/04747, filed on Aug. 19, 2009, entitled "Conjugates of Small Interfering Nucleic Acids." The conjugates can be formed from reagents bearing multiple polymer "arms" and functional groups.

For example, one such approach has the following formula:
The conjugates can be formed from reagents bearing multiple polymer "arms" and functional groups.

For example, one such multiarm approach has the following formula:

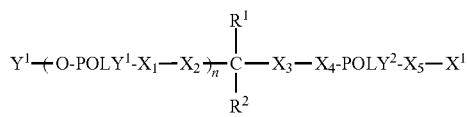

charges of the siNA would be attracted to the positive charges of POLY$^2$. Depending on the complexity of the Y$^1$, and the molecular weight of the PEG in this example, the polymeric mixture in water could form a micelle. Micelles are known to have useful drug delivery properties. See Kataoka et al. (1993) *J. Controlled Rel.* 24:119-132 and Husseini et al. (2002) *J. Controlled Rel.* 83:302-304.

Exemplary constructs are provided below.

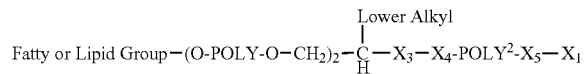

A second generic structure that will be applicable to siNA delivery is shown below. Methods for preparing the structure are described in U.S. Patent Application Publication No. 2007/0031371. While this structure is shown in a six-arm form which delivers up to six drug molecules, this structural type is also available in other numbers of arms, including two- and four-arm varieties.

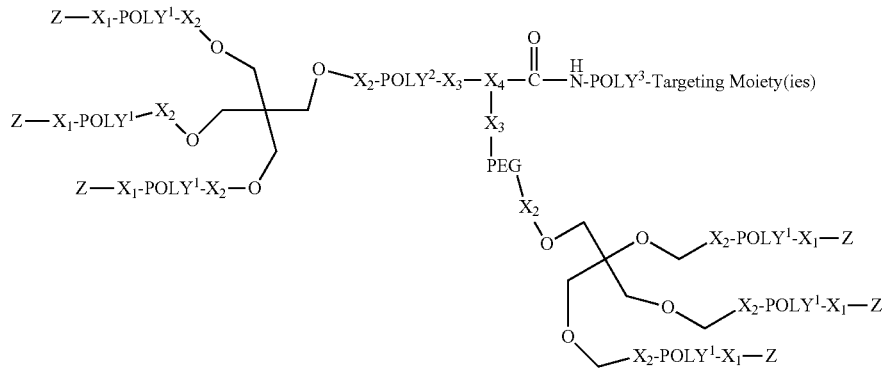

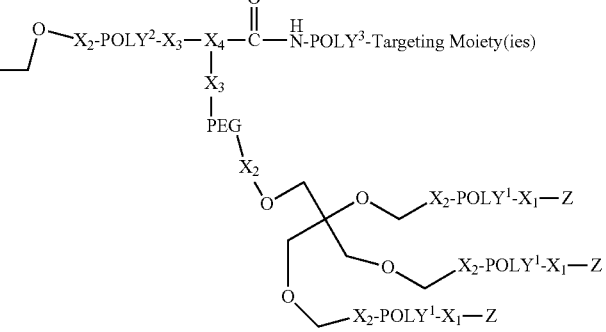

wherein:

as X$_1$, X$_2$, X$_3$, X$_4$, X$_5$ are each independently optional spacer moieties;

each POLY$^1$ is a water-soluble polymer (e.g., a PEG);

POLY$^2$ is a positively charged or neutral polymer (e.g., chitosan, polylysine, and polyethylenemine);

n is 1, 2, or 3;

R$^1$ is H or alkyl;

R$^2$ is H or alkyl;

Y$^1$ is H, lower alkyl, substituted alkyl, a fatty group (optionally substituted) including lipids (e.g., phospholipids, lipophilic vitamins, lipophilic coenzymes, or lipophilic antioxidants); and X$^1$ is an endcapping group or spacer moiety connecting an siNA or a targeting moiety (e.g., folate, pemetrexed, RGD peptide, and cholesterol).

One specific example of the use of this structure follows. POLY$^1$ is a branched PEG polymer that includes a lipid or fatty group, Y$^1$, at a terminus of a branched PEG (POLY$^1$) and as POLY$^2$ is the positively charged polymer selected from the group consisting of a polylysine (such as a modified polylysine) and polyethyleneimine. Further, optional spacer moiety, X$_5$, is present and is a releasable linker, which, when X$^1$ is a spacer moiety connecting an siNA, provides for a release of the siNA. In addition, this structure can deliver the siNA as an unbound component in a composition as the negative wherein:

X$_1$ is a degradable or releaseable spacer moiety or linker (e.g., ester, releasable carbamate, releasable disulfide, and releasable thioether);

each of X$_2$, X$_3$, X$_4$ is independently a stable spacer moiety;

each Z is a residue of a pharmacologically active agent (e.g., a siNA);

each POLY$^1$ is a water soluble polymer (e.g., a PEG);

POLY$^2$ is a water soluble oligomeric linker (e.g., a PEG, a polycationic polymer, and carbohydrate);

POLY$^3$ is a water soluble polymeric linker that is optionally positively charged (e.g., chitosan, polylysine, an polyethyleneimine); and each Targeting moiety is an organic or biologically active moiety that can binds to target and is selected to fit a specific delivery application (e.g., folate, pemetrexed and RGD peptide, or cholesterol).

The residue of the pharmacologically active agent, (Z) can also contain various structural motifs especially for siNA delivery (e.g., Z is a targeting moiety-Xn-Z— or Z-Xn-Targeting moiety-; where Xn may be a stable or releasable spacer moiety). Alternatively spacer moieties (X$_1$) could be polycationic moieties that form non-covalent ionic complex with the siNA drug.

A third generic multiarm structure is shown below. Methods for preparing the structure are described in U.S. Patent Application Publication No. 2007/0031371. This particular multiarm may have two or more arms depending on the functionality of the polypeptide linker (two or more amino acids, lysines in this example).

Drug-$X_2$-POLY$^1$-$X_1$—NH

Drug-$X_2$-POLY$^1$-$X_1$—N(H)—[...]—NH

Drug-$X_2$-POLY$^1$-$X_1$—NH

Drug-$X_2$-POLY$^1$-$X_1$—N(H)—[...]—$X_3$-POLY$_2$-Targeting Moiety wherein:

Drug is a residue of a pharmacologically active agent drug that is released in vivo;

each $X_1$ is a stable spacer moeity;

$X_3$ is a stable spacer moeity;

$X_2$ is a releasable spacer moiety (e.g., ester, releasable carbamate, releasable disulfide, and releasable thioether);

each POLY$^1$ is a water soluble polymer (e.g., a PEG);

POLY$^2$ is neutral or, optionally, positively charged water soluble polymeric linker (e.g., a PEG, polycationic polymer, and carbohydrate); and Targeting moiety is an organic or biologically active moiety that can bind to a target and is selected to fit a specific delivery application.

Spacer moieties, end groups and targeting groups will include, in some cases, lipid or phospholipids moieties. Positively charged polymers may include polyamines or polymers containing positively charged amine groups. Releaseable linkers may be, for example, FMOC-based structures and esters.

Note that the pharmacologically active agent moiety (Drug) may also contain various structural motifs especially for siNA delivery (e.g., Drug=TM-Lx-Drug- or Drug-Lx-TM-; where Lx may be a stable or releasable linker and TM is a targeting moiety). Alternatively, linkers ($X_2$) could be polycationic moieties that form non-covalent ionic complex with the siNA drug.

Additional multiarm approaches are envisioned, an example of which is provided below.

TM—$X_3$
 \\Z—$X_1$-POLY$^1$-$X_2$
              O
TM—$X_3$
 \\Z—$X_1$-POLY$^1$-$X_2$
              O
                  O—$X_2$-POLY$^1$-$X_1$—Z—$X_3$-TM
TM—$X_3$       O
 \\Z—$X_1$-POLY$^1$-$X_2$ wherein:

each $X_1$ is a releaseable spacer moiety;

each $X_2$ is a stable spacer moiety;

$X_3$ is an optionally stable or releasable spacer moiety (e.g., ester, releasable carbamate, releasable disulfide, and releasable thioether);

Z is a residue of a pharmacologically active agent (e.g., a siRNA);

each POLY$^1$ is a water soluble polymer (e.g., a PEG);

each TM is a targeting moiety, which is an optional presence on one or more polymer-linked pharmacologically active agent moieties (e.g., folate, pemetrexed, RGD peptide and cholesterol).

More structures may also be useful for targeted conjugate delivery of siNA. The targeting moieties may optionally be present on one or more of the polymer linked drug moieties and be linked via a stable or releasable linker (when the targeting moiety is stably linked to siNA, conjugation to the passenger or sense strand would be preferred).

Y-POLY$^1$-$X_1$—Z—$X_3$-TM wherein:

$X_1$ is a releaseable spacer moiety;

Y is an end-capping group or spacer moiety containing lower alkyl, alkyl or a lipid and optionally connected to a stable or releasable linked targeting moiety (e.g., folate or pemetrexed);

$X_3$ is an optional stable or releasable spacer moiety (e.g., ester, disulfide, releasable carbamate, releasable thioether, cleavable amide and peptide);

Z is a residue of a pharmacologically active agent (e.g., siRNA)

POLY$^1$ is a water soluble polymer (e.g., a PEG); and each TM is a targeting moiety (e.g., folate, pemetrexed, RGD peptide, and cholesterol), which is an optional presence on one or more polymer-linked pharmacologically active agent moieties.

Note that linear and branched PEG architectures may also be used in this context as shown above.

In the above-described structures, please note that the drug moiety (Z) may also contain various structural motifs especially for siNA delivery (e.g., Z is a targeting moiety-Xn-Z— or Z-Xn-Targeting moiety-; where Xn may be stable or releasable linker). Alternatively linkers ($X_1$) could be polycationic moieties that form non-covalent ionic complex with the siNA drug.

With respect to polymeric reagents, those described here and elsewhere can be purchased from commercial sources (e.g., Nektar Therapeutics, Huntsville, Ala. and NOF Corporation, Japan). In addition, methods for preparing the polymeric reagents are described in the literature.

The attachment between the chitosan and the non-peptidic, water-soluble polymer can be direct, wherein no intervening atoms are located between the chitosan and the polymer, or indirect, wherein one or more atoms are located between the chitosan and the polymer. With respect to the indirect attachment, a "spacer moiety" or "linker" serves as a linker between the chitosan and the water-soluble polymer. The one or more atoms making up the spacer moiety can include one or more of carbon atoms, nitrogen atoms, sulfur atoms, oxygen atoms, and combinations thereof. The spacer moiety can comprise an amide, secondary amine, carbamate, thioether, and/or disulfide group. Nonlimiting examples of specific spacer moieties include those selected from the group consisting of "—" (a covalent bond), —O—, —S—, —S—S—, —C(O)—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—, —CH$_2$—O—CH$_2$—CH$_2$—, —CH$_2$—CH$_2$—O—CH$_2$—, —CH$_2$—CH$_2$—O—CH$_2$—CH$_2$—, —O—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—CH$_2$—, —O—C(O)—NH—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_h$—(OCH$_2$CH$_2$)$_j$—, bivalent cycloalkyl group, —O—, —S—, an amino acid, —N(R$^6$)—, and combinations of two or more of any of the foregoing, wherein R$^6$ is H or an organic radical selected from the group consisting of alkyl, substituted alkyl, alkenyl, substituted alkenyl, alkynyl, substituted alkynyl, aryl and substituted aryl, (h) is zero to six, and (j) is zero to 20. Other specific spacer moieties have the following structures: —C(O)—NH—(CH$_2$)$_{1-6}$—NH—C(O)—, —NH—C(O)—NH—(CH$_2$)$_{1-6}$—NH—C(O)—, and —O—C(O)—NH—(CH$_2$)$_{1-6}$—NH—C(O)—, wherein the subscript values following each methylene indicate the number of methylenes contained in the structure, e.g., (CH$_2$)$_{1-6}$ means that the structure can contain 1, 2, 3, 4, 5 or 6 methylenes. Additionally, any of the above spacer moieties may further include an ethylene oxide oligomer chain comprising 1 to 20 ethylene oxide monomer units [i.e., —(CH$_2$CH$_2$O)$_{1-20}$]. That is, the ethylene oxide oligomer chain can occur before or after the spacer moiety, and optionally in between any two atoms of a spacer moiety comprised of two or more atoms. Also, the oligomer chain would not be considered part of the spacer moiety if the oligomer is adjacent to a polymer segment and merely represent an extension of the polymer segment.

Targeting Moiety

In one or more embodiments of the invention, a targeting moiety is included within the constructs.

A. Types of Targeting Moieties

With respect to the targeting moiety, the targeting moiety can be any moiety that serves to bind or to provide localization to a target or epitope of interest. Those of ordinary skill in the art can identify whether a target or epitope is associated with a useful target in a given patient, and if so, what the target or epitope is and/or how to obtain a targeting moiety (e.g., raising an antibody to the epitope) that will bind to that target or epitope. Often, the target will be a xenobiotic, cancer cell, and/or a protein indicative of a diseased state.

The constructs of the invention, by including a targeting moiety, are more likely to localize to the ligand or target of interest to which the targeting moiety binds or is otherwise directed. In some instances, the ligand or targeting area is located on and/or associated with a larger particle (e.g., a protein, such as a receptor protein, on a cell or virus). In some instances, the ligand or targeting area circulates and/or travels in vivo, such as a ligand located on and/or associated with a cell or soluble macromolecule. Furthermore, because the constructs of the invention also include a siNA, the constructs similarly localize the siNA. In this way, upon administration of a construct, a siNA can better localize to an area of interest.

Nonlimiting examples of targeting moieties useful as part of the constructs of the invention are those made from nucleic acids (e.g., one or more nucleic acids used for base pairing and aptamers), amino acids (e.g., proteins, peptides, and polypeptides), carbohydrates and small molecules (e.g., folic acid and folic acid derivatives).

For example, targeting moieties include fibronectin targeting molecules such as adnectins (see e.g., WO 01/64942 and U.S. Pat. Nos. 6,673,901, 6,703,199, 7,078,490, and 7,119,171), affibodies (see e.g., U.S. Pat. Nos. 6,740,734 and 6,602,977 and WO 00/63243), anticalins (also known as "lipocalins") (see e.g., WO99/16873 and WO 05/019254), and A domain proteins (see e.g., WO 02/088171 and WO 04/044011). Additional nonlimiting examples of targeting moieties include repeat proteins and antibody moieties. Exemplary targeting moieties are described below.

i. Repeat Proteins as the Targeting Moiety

"Repeat proteins," either naturally or designed, are proteins that comprise a set of target interaction residues that can bind to a target and can serve as a targeting moiety within the constructs of the invention. These target interaction residues are often a part of a series of "repeat units" which include the target interaction residues as well as framework residues. A series (e.g., two to six) of "repeat units," in turn, makes up a distinct repeat module. A series of "repeat modules," in turn, forms a "repeat domain." Finally, a series of "repeat domains" forms a repeat protein. Although naturally occurring repeat proteins are known, "designed" repeat proteins (often based on these naturally occurring repeat proteins) have also been disclosed and both of which (i.e., naturally occurring and designed) can be used a "targeting moiety" herein.

Exemplary designed repeat proteins are based on ankyrin repeat proteins (sometimes referred to as "DARPins" or designed ankyrin repeat proteins) and armadillo repeat proteins (or designed armadillo repeat proteins). These and other repeat proteins are more fully explained in the literature. See for example, U.S. Patent Application Publication No. 2009/0082274, WO 09/040,338, WO 06/083275 and WO 02/20565 and Stumpp et al. (2007) "DARPins: a True Alternative to Antibodies" Curr. Opin. Drug. Discov. Devel. 10:153-159; Zahnd et al. (2007) "A designed ankyrin repeat protein evolved to picomolar affinity to Her2." J. Mol. Biol. 369: 1015-1028; Amstutz et al. (2005) J. Biol. Chem. 280:24715-24722; Binz et al. (2005) "Engineering Novel Targeting Proteins from Nonimmunoglobulin Domains" Nat. Biotechnol. 23:1257-1268; Binz et al. (2004) "High-affinity Binders from Designed Ankyrin Repeat Protein Libraries" Nat. Biotechnol. 22:575-582; and Forrer et al. (2003) "A Novel Strategy to Design Targeting Molecules Harnessing the Modular Nature of Repeat Proteins" FEBS Lett. 539:2-6.

ii. Antibody Moieties as the Targeting Moiety

With respect to an antibody moiety as the targeting moiety, in one or more embodiments of the invention, an antibody moiety can be a full length antibody or a fragment of an antibody, so long as the antibody moiety (full length or fragment) can bind to an epitope associated with a target desired in a patient. Nonlimiting examples of antibody moieties useful in accordance with the invention include antibody moieties to microorganisms (including respiratory pathogens), monoclonal antibody moieties directed against tumor antigens and antibody moieties to cell receptors (including receptors involved in inflammation and allergy). The antibody moiety may be a full-length antibody as well as an antibody-fragment. When an antibody fragment is used, any fragment type may be used so long as the antibody fragment of interest can bind to an epitope of interest. Generally, however, when an antibody fragment is used, the antibody fragment will usually be selected from the group consisting of Fab fragments, F(ab)$_2$ fragments, Fv fragments, scFv fragments, and single polypeptide chain targeting molecules.

With regard to an antibody fragment serving as the targeting moiety, technologies have been developed which take advantage of the functional $V_{HH}$ targeting domains of antibodies including a heavy-chain. The $V_{HH}$ domain can be cloned and isolated and still have functional targeting capacity. These $V_{HH}$ are the smallest available intact antigen-targeting fragments having a molecular weight of approximately 15 kiloDaltons (approximately 118 to 136 amino acid residues). For this reason they are sometimes referred to as "nanobodies." Functional $V_{HH}$ can be made by proteolysed HCAb of an immunized camelid, cloned $V_{HH}$ genes from immunized camelid B-cells, or from libraries. Phage display techniques can be used to select the $V_{HH}$ having the desired specificity. Other $V_H$ can be made more soluble and non-specific targeting can be minimized by replacing amino acid residues therein with $V_{HH}$ residues or residues with similar chemical properties. This process is known in the art as "camelization."

In addition, a single polypeptide chain (e.g., a single $V_H$ chain), preferably derived from a library of camel or llama antibodies or camelized antibodies (Nuttall et al., Curr. Pharm. Biotechnol. 1: 253-263 (2000); J. Biotechnol. 74: 277-302 (2001)) can be used as the targeting moiety. In the case of the single $V_H$ chain polypeptides, the polypeptides can comprise the polypeptide sequence of a whole heavy chain antibody or only the amino terminal variable domain of the heavy chain antibody. In another aspect, the targeting moiety will comprise in a single polypeptide chain the variable light chain domain ($V_L$) linked to the variable heavy chain domain ($V_H$) to provide a single recombinant polypeptide comprising the Fv region of the antibody molecule (scFv).

Antibodies suitable for use as an antibody moiety include IgA, IgE, IgG, IgD and IgM. It is preferred, however, that IgA, IgG and IgM are used, with IgG and IgA antibodies being particularly preferred.

In some instances, the antibody moiety used to make constructs described herein can be in the form of polyclonal antibodies. Polycloncal antibodies can be formed by injecting (e.g., by subcutaneous, intraperitoneal, or intramuscular injection) into an animal host the antigen against which the antibody will bind. The animal host is typically, although not necessarily, a rabbit or a mouse. Often, the injection site on the host will be shaved and swabbed with alcohol prior to the injection. The injection generally occurs in multiple sites in the animal host. Typically, the total volume of the antigen-containing injection is not more than about 1 mL.

Having injected the antigen into the host animal, the host animal's immune response is allowed to start producing antibodies directed against the antigen. Specifically, lymphocytes of the host animal will produce and secrete antibodies to the antigen into the blood stream. Although each targeting to same antigen, the different antibodies likely bind to different antigenic epitopes, thereby providing the "polyclonal" nature of antibodies produced in this approach.

In order can recover the polyclonal antibodies now circulating in the animal host's blood stream, blood collection from the animal is performed. The blood can be collected using conventional techniques such as inserting the tip of a needle equipped with a syringe into the host. Blood is then collected and typically allowed to clot at 37° C. overnight. The clotted blood is then generally refrigerated for 24 hours before the serum is recovered by conventional techniques (e.g., by running a centrifuge at 2500 revolutions per minute for about 20 minutes and collecting the antibody-containing portion). Blood collection is performed periodically, such as at about four weeks following injection of the antigen, seven weeks following injection of the antigen, 11 weeks following injection of the antigen, and every three weeks thereafter.

The blood collections serve the dual purposes of determining the titer of the desired antibody (through, for example, conventional enzyme-linked immunosorbant assay or "ELISA") as well as recovering the antibodies (assuming a sufficient titer is present). The antibodies in any given sample can be recovered through, for example, centrifuging, separating through an affinity column (e.g., a "protein-A" column), and a combination thereof. Additional recovery techniques are known to those of ordinary skill in the art and can be used as well.

To the extent that any given sample of the blood has an insufficient or a generally low titer, a number of approaches are used to increase the titer and/or maintain the titer at levels sufficient to provide antibodies. In one approach, the antigen introduced into the animal host can be conjugated to a protein (e.g., keyhole limpet hemocyanin or serum albumin), thereby increasing the overall antigenicity of the antigen. In addition, other substances known as adjuvants can be injected along with the antigen in order to enhance the immunogenic response. Typically, complete Freund's adjuvant is injected along with the antigen in the initial injection and incomplete Fruend's adjuvant is injected along with the antigen during subsequent injections. Both complete Freund's adjuvant and incomplete Freund's adjuvant are available commercially and through, for example, Sigma-Aldrich, Inc. (St. Louis, Mo.).

In some instances, the antibody moiety used to make the constructs described herein can be in the form of a monoclonal antibody. Monoclonal antibodies can also be used in accordance with the present invention. Produced from a cultured colony of cells derived from a single lymphocyte, monoclonal antibodies recognize only one eptitope on an antigen. Monoclonal antibodies can conveniently be prepared using the process described in Kohler et al. (1975) *Nature* 256:495.

Briefly, monoclonal antibodies can be prepared by first injecting the antigen of interest into a suitable animal host such as a mouse. Thereafter, the animal host is euthanized and the spleen is removed so as to recover the animal host's antibody-producing lymphocytes in the spleen. Due to their limited growth potential, the normal, antibody-producing lymphocytes are fused with cancer cells in order to take advantage of the prolific and virtually unlimited growth of cancer cells. The fusion of the lymphocyte and cancer cell results in a hybridoma cell. When placed in a suitable cell medium, the hybridoma cell line can grow indefinitely. Fusion of the two different types of cells occurs using a conventional fusing agent, such as polyethylene glycol.

The cancer cell used in the hybridoma and the cell culture medium are specifically chosen so that it is possible to select for hybridomas. This can be accomplished by using a myeloma cell that has lost the ability to synthesize hypoxanthine-guanine phosphoribosyltransferase (HGPRT) as the cancer cell and a HAT medium (i.e., a cell culture medium comprising hypoxanthine, aminopterin and the pyrimidine thymidine) as the cell culture medium. This approach is premised on the ability of cells to obtain life-sustaining purines through two pathways: a first pathway that requires the enzyme HGPRT in the presence of hypoxanthine; and a second pathway mediated by folic acid that is blocked in the presence of a folic acid antagonist such as methotrexate or aminopterin. The logic of this approach is as follows: (i) unfused myeloma cells lacking HGPRT will not grow because they cannot use the hypoxanthine present in the HAT medium since they lack the necessary enzyme HGPRT and because the folic acid antagonist, aminopterin, in the HAT medium blocks the folic acid mediated pathway to purine synthesis; (ii) unfused lymphocytes cannot grow indefinitely due to their limited life spans; and (iii) hybridoma cells (successful fusions between the lymphocyte and cancer cells) are able to growth indefinitely because the lymphocyte provides the HGPRT necessary to utilize the hypoxanthine necessary to form purines.

Preferred HGPRT-deficient cells include the murine-based MOPC-21 and MPC-11 cells available from the Salk Institute Cell Distribution Center (San Diego, Calif.) and the SP2 cells available from the American Type Culture Collection (Rockville, Md.). Cell media, including the HAT medium, are available commercially from sources such as Sigma-Aldrich, Inc. (St. Louis, Mo.).

The hybridomas are then assayed for the production of antibodies using conventional techniques such as immunoprecipitation, radioimmunoassay, ELISA or a similar technique. When a hybridoma is identified that produces the desired antibody (i.e., an antibody directed against a specific epitope on a specific antigen), the hybridoma is then subcloned by placing the hybridoma in a suitable medium and allowed to grow. In this way, a monoclonal population is formed.

The monoclonal antibodies secreted by subcloned hybridomas are separated using conventional techniques such as through protein-A columns, gel electrophoresis, the affinity chromatography, and the like.

In some instances, the targeting moiety used to prepare the constructs described herein can be derived using recombinant DNA technology. For example, the DNA encoding the monoclonal antibodies can be isolated from the hybridoma cells through, for example, use of the appropriate oligonucleotide probes. Thereafter, the DNA can be placed into suitable expression vectors, which can then be transfected into host cells such as E. coli cells, Chinese hamster ovary (CHO) cells or other cell that does not produce immunoglobulins. The DNA obtained from the hybridoma cells can, of course, be modified prior to transfection. For example, the coding sequences for human heavy- and light-chain constant domains or other regions can be substituted for the homologous host (murine) cell's sequences. In this way, the resulting antibody is more humanized and will typically be less antigenic upon administration to a human. See, for example, U.S. Pat. No. 4,816,567.

In some instances, the targeting moiety used to prepare constructs described herein can conveniently be obtained through a variety of suppliers. For example, cells producing antibodies can be obtained from the Salk Institute Cell Distribution Center (San Diego, Calif.) and the American Type Culture Collection (Rockville, Md.). In addition, commercial suppliers such as Sigma-Aldrich (St. Louis, Mo.) and others can provide antibodies.

In some instances, the targeting moiety used to prepare constructs described herein can be adapted or further modified, depending on the needs or desires of the scientist, clinician, or diagnostician. For example, chimeric forms of an antibody that combine two or more portions derived from or based on different organisms can be used. In addition, CDR-grafted antibodies and/or different glycosylated forms can be used.

Any type of targeting moiety can be used and the invention is not limited in this regard. For example, chimeric antibodies can be used in which the whole of the variable regions of a mouse or other host are expressed along with human constant regions, thereby providing the antibody with human effector functions as well as decreased immunogenicity. In addition, humanized and CDR grafted antibodies in which the complimentarity determining regions from the mouse or host antibody V-regions are combined with framework regions from human V-regions, thereby resulting in decreased immunogenicity. In addition, fully human antibodies can be used that have been prepared from synthetic phage libraries or from transgenic mice or other transgenic animals treated such that they synthesize human immunoglobulin germline gene segments. It will be understood that the term "antibody moiety" as used herein encompasses each of these types of antibodies.

Exemplary targeting moieties include (without limitation) abciximab, adalimumab, afelimobam, alemtuzumab, AME-133v, AMG-655, antibody in PSMA ADC (Progenics Pharmaceuticals, Inc., Tarrytown N.Y.), antibody to B-lymphocyte, antibody to FZD-10, antibody marketed under the AUROGRAB® trademark (Neutec Pharma Ltd., Manchester England), antibody marketed under the MYCOGRAB® trademark (Neutec Pharma Ltd., Manchester, England), apomab, apolizumab, atlizumab, ATM-027, basiliximab, bevacizumab, biciromab, bivatuzumab, BMS-188667, BMS-224818, BR96, CAT-213 or bertilimumab, capromab, CDP-571, CDP-860, CDP-870, cetuximab, clenoliximab, CS-1008, dacetuzumab, daclizumab, denosumab, eculizumab, edrecolomab, efalizumab, epratuzumab, fanolesomab, fontolizumab, GA101, gavilimomab, gemtuzumab, golimumab, ibalizumab, ibritumomab, infliximab, inolimomab, J-695, keliximab, labetuzumab, LBY135, lerdelimumab, lexatumumab, liciliomab, lintuzumab, lym-1, mapatumumab, matuzumab, MDX-070, metelimumab, mepolizumab, MH-1, mitumomab, $MLN_{591}RL$; MLN-2704; muromonad-CD3, nebacumab, natalizumab, ocrelizumab, odulimomab, ofatumumab, omalizumab, oregovomab, palivizumab, panitumumab, pascolizumab, pemtumomab, pertuzumab, pexelizumab, PRO-120, ranibizumab, rituximab, satumomab pendetide, SC-1, sevirumab, SGN-15, SGN-70, siplizumab, stamulumab or MYO-029, sulesomab, tositumomab, trastuzumab, TRU-015, tuvirumab, ustekinumab, veltuzumab, and visilizumab.

Exemplary targets of the targeting moiety include, without limitation CCR5, CXCR4, CD4, CD20, efflux transporters, epidermal growth factor-receptor (EGFR) (also referred to as erbB-1 or HER1); erbB-2 (also referred to as HER2); erbB-3 (also referred to as HER3); erbB-4 (also referred to as HER4); FCεR; frizzled-10 (FZD-10); gp41; gp120; IgE antibodies, insulin-like growth factor (IGF1); insulin-like growth factor receptor (IGF1R); IGF2R; InsR; interleukin-1 receptor, mesenchymal-epithelial transition factor receptor (c-MET receptor); outer membrane proteins (Omps) including, for example, OmpA, OmpC, and OmpF (OprF); matrix metalloproteinase-9; matrix metalloproteinase-13; methacillin-resistant S. aureus ABC proteins (MSRA ABC proteins); myostatin penicillin-targeting proteins (PBPs), including, for example, PBP1, PBP1a, PBP1b, PBP2, PBP2a, PBP2', PBP3; peptidoglycan (also referred to as murein); prostate-specific antigen (PSA); prostate-specific membrane antigen (PSMA);

pneumococcal surface adhesion protein A (PsaA); receptor activator for nuclear factor κ B (RANK); receptor activator for nuclear factor κ B ligand (RANKL); sclerostin; *S. pneumoniae* Pit1 (also referred to as Piu); *S. pneumoniae* Pit2 (also referred to as Pia); tumor markers, uPA; uPAR; and vancomycin-resistant *E. Faecium* ABC proteins.

Compositions

The complexes are typically part of a composition. Generally, the composition comprises a plurality of complexes, preferably although not necessarily, each complex is comprised of the same siNA (i.e., within the entire composition, only one type of siNA is found). In addition, the composition can comprise a plurality of complexes wherein any given complex is comprised of a moiety selected from the group consisting of two or more different siNA moieties (i.e., within the entire composition, two or more different siNA moieties are found). Optimally, however, substantially all complexes in the composition (e.g., 85% or more of the plurality of conjugates in the composition) are each comprised of the same siNA.

The complexes can be purified to obtain/isolate different complex species. The strategy for purification of the final complex reaction mixture will depend upon a number of factors, including, for example, the molecular weight of the components employed, the particular siNA, the desired dosing regimen, and so forth.

If desired, complexes having different molecular weights can be isolated using gel filtration chromatography and/or ion exchange chromatography. That is to say, gel filtration chromatography is used to fractionate differently sized complexes on the basis of their differing molecular weights.

Optionally, the composition of the invention further comprises a transfection agent to enhance, for example, the intracellular update of one or more components of the complex. Exemplary transfection agents include, but are not limited to, DEAE, dextran, DEAE-dextran, calcium phosphate, cationic lipids, and the like.

Optionally, the composition of the invention further comprises a pharmaceutically acceptable excipient. If desired, the pharmaceutically acceptable excipient can be added to a complex to form a composition.

Exemplary excipients include, without limitation, those selected from the group consisting of carbohydrates, inorganic salts, antimicrobial agents, antioxidants, surfactants, buffers, acids, bases, and combinations thereof.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myoinositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for one or more embodiments of the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in one or more embodiments of the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the active agent and the polymeric reagent) in the composition will vary depending on a number of factors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", 19$^{th}$ ed., Williams & Williams, (1995), the "Physician's Desk Reference", 52$^{nd}$ ed., Medical Economics, Montvale, N.J. (1998), and Kibbe, A. H., Handbook of Pharmaceutical Excipients, 3$^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

In some embodiments of the invention, the compositions comprising the complexes may further be incorporated into a suitable delivery vehicle. Such delivery vehicles may provide controlled and/or continuous release of the complexes and may also serve as a targeting moiety. Non-limiting examples of delivery vehicles include, adjuvants, synthetic adjuvants, microcapsules, microparticles, liposomes, and yeast cell wall particles. Yeast cells walls may be variously processed to selectively remove protein component, glucan, or mannan layers, and are referred to as whole glucan particles (WGP), yeast beta-glucan mannan particles (YGMP), yeast glucan particles (YGP), *Rhodotorula* yeast cell particles (YCP). Yeast cells such as *S. cerevisiae* and *Rhodotorula* sp. are preferred; however, any yeast cell may be used. These yeast cells exhibit different properties in terms of hydrodynamic volume and also differ in the target organ where they may release their contents. The methods of manufacture and characterization of these particles are described in U.S. Pat. Nos. 5,741,495; 4,810,646; 4,992,540; 5,028,703; 5,607,677, and U.S. Patent Applications Nos. 2005/0281781, and 2008/0044438. In one or more embodiments, the delivery vehicle is not a liposomal in nature (i.e., lacks liposomes).

The compositions of one or more embodiments of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

With respect to pulmonary delivery of the complexes described herein, it is preferred to employ one or more of the approaches described in U.S. Pat. Nos. 6,565,885; 6,946,117; 6,309,623; and 6,433,040; the contents of all of which are hereby incorporated herein by reference in their entirety.

The invention also provides a method for administering a complex as provided herein to a patient suffering from a condition that is responsive to treatment with complex. The method comprises administering to a patient, generally via injection, a therapeutically effective amount of the complex (preferably provided as part of a pharmaceutical composition). As previously described, the complexes can be administered injected parenterally by intravenous injection. Advantageously, the complex can be administered by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of the complex. Those of ordinary skill in the art appreciate which conditions a specific complex can effectively treat. Advantageously, the complex can be administered to the patient prior to, simultaneously with, or after administration of another active agent.

The actual dose to be administered will vary depending upon the age, weight, and general condition of the subject as well as the severity of the condition being treated, the judgment of the health care professional, and complex being administered. Therapeutically effective amounts are known to those skilled in the art and/or are described in the pertinent reference texts and literature. Generally, a therapeutically effective amount will range from about 0.001 mg to 100 mg, preferably in doses from 0.01 mg/day to 75 mg/day, and more preferably in doses from 0.10 mg/day to 50 mg/day. A given dose can be periodically administered up until, for example, symptoms of organophosphate poisoning lessen and/or are eliminated entirely.

The unit dosage of any given complex (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration once daily, three times weekly, twice weekly, once weekly, twice monthly, once monthly, and any combination thereof. Once the clinical endpoint has been achieved, dosing of the composition is halted.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

EXPERIMENTAL

The practice of the invention will employ, unless otherwise indicated, conventional techniques of organic synthesis and the like, which are within the skill of the art. Such techniques are fully described in the literature. Reagents and materials are commercially available and/or their syntheses (particularly with respect to polymeric reagents) are described in the literature unless specifically stated to the contrary. See, for example, M. B. Smith and J. March, *March's Advanced Organic Chemistry: Reactions Mechanisms and Structure*, 6th Ed. (New York: Wiley-Interscience, 2007), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R., et al., Elsevier Science.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

References in this Experimental to polymeric reagents identified by the following designations shall represent the following structure:

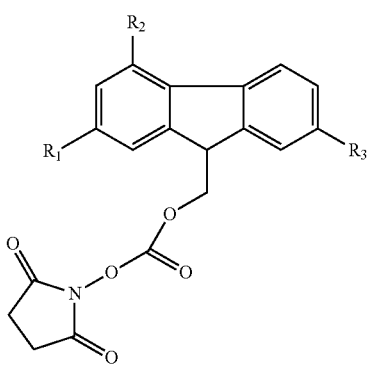

wherein, when the polymeric reagent designated as:
"C2," $R_2$ is H and each of $R_1$ and $R_3$ is

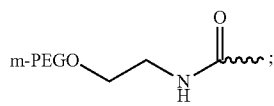

"G2," $R_2$ is H and each of $R_1$ and $R_3$ is

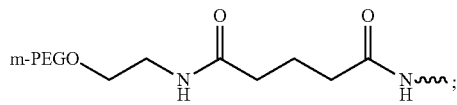

"CG," $R_1$ is H, $R_2$ is

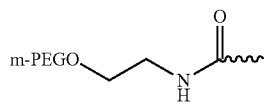

and $R_3$ is

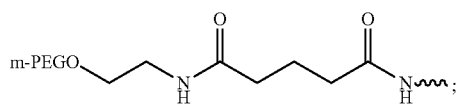

and
"CAC," $R_1$ is H, $R_2$ is

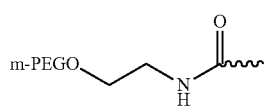

and $R_3$ is

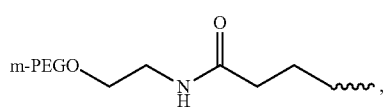

and each m-PEG represents $CH_3$—O—$(CH_2CH_2O)_n$—$CH_2CH_2$~ and (n) is defined such that both m-PEG moieties in the structure provide the molecular weight stated in the particular example.

Further, the following structures shall be identified in this Experimental by the designations located adjacent to the structure:

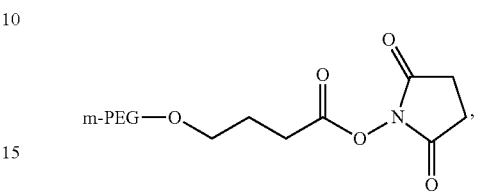

m-PEG-SBA

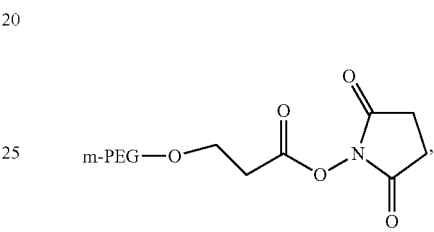

m-PEG-SPA

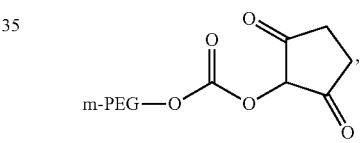

m-PEG-SC;

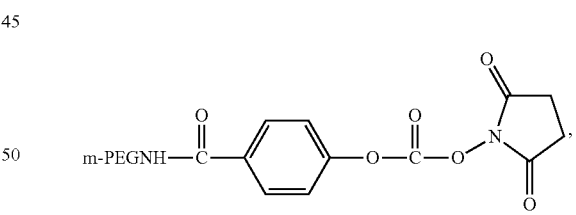

m-PEG-SBC;

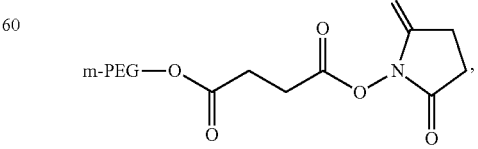

m-PEG-SS

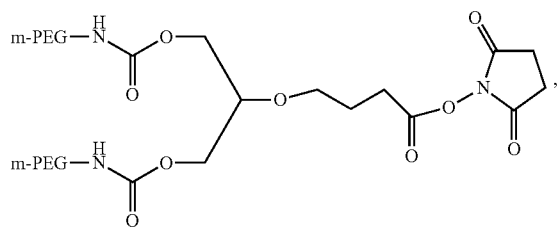

m-PEG2-RU-NHS; and ride with average MW about 10,000 Daltons (measured by GPC) and with ~94% deacetylation (measured by NMR) and chitooligosaccharide average MW 3,000-5,000 Daltons (measured by GPC) and with ~86% deacetylation (by NMR). Generally, it is preferred to use chitosan lacking derivatization with side chains of $-NH-(CH_2)_a-(NH(CH_2)_2)_e-NH_2$, where (a) and (e) are independently 1 to 5. Generally, it is also preferred to use chitosan with a molecular weight of less than about 100,000 Daltons, more preferably less than about 60,000 Daltons, still more preferably less than 30,000 Daltons, with less than 20,000 Daltons being most preferred.

Further, the following siNAs (single-stranded oligonucleotide sequences are identified with SEQ ID NOs), shall be identified in this Experimental by the SEQ ID NOs located adjacent to the sequence or corresponding oligonucleotide (oligo) number:

| Sequence | Name | SEQ ID NO: |
|---|---|---|
| 5'(C6-NH2) AmCAmACmAGmACmUUmUAmAUmGUmAA-3' | Oligo 13 | 183 |
| 5'(C6-NH2) AmCAmACmAGmACmUUmUAmAUmGUmAA-3'(C6-SH)(Cy5.5) | Oligo 14 | 184 |
| 5'(C6-NH2) AmCAmACmAGmACmUUmUAmAUmGUmAA-3'(cholesteryl-TEG) | Oligo 18 | 185 |
| 5'(C6-S-SC6)-AmCAmACmAGmACmUUmUAmAUmGUmAA-3' | Oligo 3 | 186 |
| 5'(C6-NH2)AmCAmACmAGmACmUUmUAmAUmGUmAA-3'(C6-NH) | Oligo 5 | 187 |
| 5'mUUmACmAUmUAmAAmGUmCUmGUmUGmU-3'(C6-NH)(Cy5.5) | Oligo 28 | 188 |
| 5'mUUmACmAUmUAmAAmGUmCUmGUmUGmU-3'C6-NH2) | Oligo 31 | 189 |
| 5'mUUmACmAUmUAmAAmGUmCUmGUmUGmU-3' C3-S-S-C3 | Oligo 34 | 190 |
| 5' AmCAmACmAGmACmUUmUAmAUmGUmAA-3' | Sense | 191 |
| 5'mUUmACmAUmUAmAAmGUmCUmGUmUGmU-3' | Antisense | 192 |
| - Ai2FCAAi2FCAGAi2FCTi2FUTAATGTAAmUmU | Sense | 193 |
| 5'- rUmUrAmCAi2FUmUAmAAmGmUi2FCi2FUmGi2FUmUmGi2FUmUmU | Antisense | 194 |

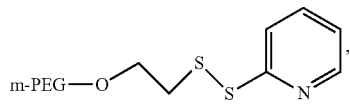

m-PEG-OPSS,
wherein m-PEG represents $CH_3-O-(CH_2CH_2O)_n-CH_2CH_2\sim$ and (n) is defined such that m-PEG moiety in the structure provides the molecular weight stated in the particular example.

The C2, G2, CG, CAC, SBC and SS polymeric reagents, upon conjugation to the siNA, provide conjugates that are releaseable in vivo (i.e., wherein the polymeric reagent detaches or substantially detaches from the conjugate, thereby releasing the original siNA or an siNA only slightly modified with a small residue from the polymeric reagent), whereas the PEG2-RU-NHS polymeric reagent, upon conjugation to the siNA, provides a substantially stable conjugate. The OPSS polymeric reagent, upon conjugation to the siNA, provides a conjugate that may undergo disulfide exchange. Single- and double-stranded RNA sequences were manufactured by Tri-Link BioTechnologies, San Diego, Calif., Dharmacon RNAi Technologies, Lafayette, Colo., and IDT Inc., Coralville, Iowa. Chitosan was obtained from Kitto Life, Kyongki-Do, Korea. Two forms were used: chitooligosaccha- Example 1

Conjugation of Double-Stranded siRNA with a 5'-aminoC6 Linker with

1a) CAC 20K Polymeric Reagent ["9-hydroxymethyl-4-(mPEG(10,000)-carboxyamide)-7-(3-(mPEG (10,000)carbamoyl-propyl)-fluorene-N-hydroxysuccinimide" or "4,7-CAC-PEG2-FMOC-NHS 20K"]

and

1b) GC 20K Polymeric Reagent ["9-hydroxymethyl-4-(mPEG(10,000)-carboxyamide)-7-(3-(mPEG(10, 000) amidoglutaric amide)-fluorene-N-hydroxysuccinimide" or "4,7-CG-PEG2-FMOC-NHS 20K"]

Sodium phosphate buffer (25 mM; pH 7.5) was prepared. A stock solution (280 µM) of double-stranded siRNA with a 5'-aminoC6 linker on the sense strand (SEQ ID NO: 183:SEQ ID NO: 192) (IDT Inc., Coralville, Iowa) was prepared in 1×siRNA buffer (diluted from 5×siRNA buffer, pH 7.5, Dharmacon Lafayette, Colo.). The reactions were run by dissolution of the indicated polymeric reagent CAC or GC (4 mg, 0.2 µmol) in a mixture of siRNA stock solution (27 µl, 0.0075 µmol) and the indicated sodium phosphate buffer (25 mM, 173 µl). The reaction mixtures were stirred and incubated at room temperature for three hours. Aliquots (2 µl) were taken, quenched with 0.1 M glycine (2 µl) and diluted with RNAse free water and 6× loading buffer (comprised of 10 mM pH 7.6 Tris buffer, 60 mM EDTA, 60% glycerol, 0.03% bromophenol blue and 0.03% xylene cyanol). The samples were loaded on a non-denaturing PAGE gel (Invitrogen 20% TBE gel) and run at 100 V for 120 min. The gels were removed, stained with ethidium bromide (BioChemika, Sigma) for 30 minutes and then destained for more than one hour.

Figure 1:
FIG. 1 is a representation of a gel as further described in Example 1.

The gel is provided in FIG. 1, wherein lanes 1 and 2 correspond to siRNA-CAC conjugate, lane 3 corresponds to siRNA, and lanes 4 and 5 correspond to siRNA-CG conjugate.

Example 2

Conjugation of Double-Stranded siRNA and Single-Stranded siRNA with 2a) m-PEG-SBA 5K ["mPEG-succinimidyl butanoate 5K"

and 2b) m-PEG-SPA 5K [or "mPEG-succinimidyl propionate 5K"]

Preparation of Conjugates with a Double-Stranded siRNA

Sodium phosphate buffer (100 mM; pH 8.0) was prepared. A stock solution (280 µM) of double-stranded siRNA with a 5'-aminoC6 linker on the sense strand (SEQ ID NO: 183:SEQ ID NO: 192) (IDT Inc., Coralville, Iowa) was prepared in 1×siRNA buffer (diluted from 5×siRNA buffer, pH 7.5, Dharmacon, Lafayette, Colo.). The reactions in were run by dissolution of the indicated polymeric reagent (1 mg, 0.2 µmol) in a mixture of siRNA stock solution (10 µl, 0.0028 µmol) and the indicated sodium phosphate buffer (100 mM, 90 µl). The reaction mixtures were stirred and incubated at room temperature for three hours. Aliquots (2 µl) were taken, quenched with 0.1 M glycine (2 µl) and diluted with RNAse free water and loading buffer.

Preparation of Conjugates with a Single-Stranded siRNA

A stock solution (1000 µM) of siRNA sense-strand with a 5'-aminoC6 linker (SEQ ID NO: 183) (IDT Inc., Coralville, Iowa) was prepared in 1×siRNA buffer. The reactions were run by dissolution of mPEG-SBA 5K reagent (1 mg, 0.2 µmol) in a mixture of siRNA stock solution (10 µl, 0.01 µmol) and the indicated sodium phosphate buffer (100 mM, 90 µl). The reaction mixtures were stirred and incubated at room temperature for three hours. Aliquots (2 µl) were taken, quenched with 0.1 M glycine (2 µl) and diluted with RNAse free water and loading buffer.

The samples were loaded on a non-denaturing PAGE gel (Invitrogen 20% TBE gel) and run at 100 V for 120 minutes. The gels were removed, stained with ethidium bromide (BioChemika, Sigma) for 30 minutes and then destained for more than one hour.

Figure 2:
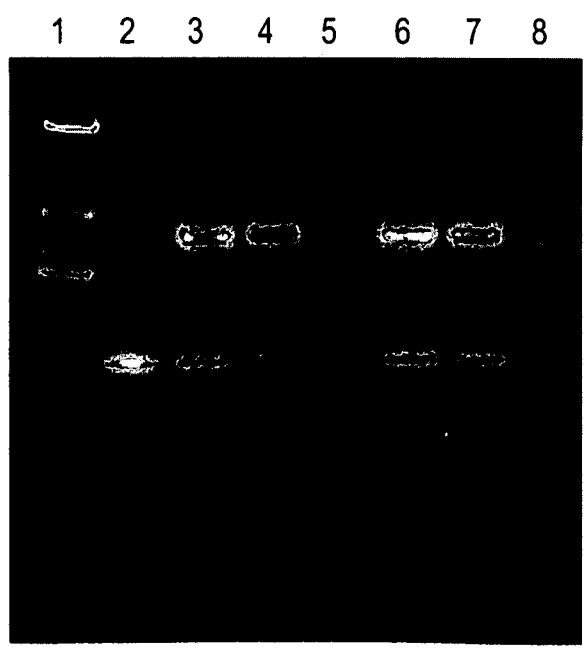
FIG. 2 is a representation of a gel as further described in Example 2.

The gel is provided in FIG. 2, showing native PAGE 5'-aminoC6 double-stranded siRNA (280 µM)+mPEG-SBA 5K or mPEG-SPA 5K (70×) comparisons with 5'-aminoC6 siRNA sense strain (1000 µM)+mPEG-SBA 5K (20×) at pH 8.0 in 100 mM phosphate buffer for three hours. Lane corresponds to a 10 bp DNA ladder, lane 2 corresponds to double-stranded siRNA, lane 3 corresponds to double-stranded siRNA-mPEG-SBA 5K conjugate, lane 4 corresponds to double-stranded siRNA-mPEG-SPA 5K conjugate, lane 5 corresponds to siRNA sense strain-mPEG-SBA 5K conjugate, lane 6 corresponds to double-stranded siRNA-mPEG-SBA 5K conjugate, lane 7 corresponds to double-stranded siRNA-mPEG-SPA 5K conjugate, lane 8 corresponds to siRNA sense strain-mPEG-SBA 5K, conjugate, and 9 corresponds to double-stranded siRNA.

Example 3a-3f

Conjugation of Double-Stranded siRNA (ds-siRNA) and Single-Stranded siRNA (ss-siRNA) with Polymeric Reagents 3a) and 3b) m-PEG2-RU-NHS 20K ["reversed-urethane branched PEG NHS 20K"], 3c) and 3d) m-PEG-SC 20K ["mPEG succinimido carbonate 20K"]

and 3e) and 3f) CAC ["9-hydroxymethyl-4-(mPEG(10,000)-carboxyamide)-7-(3-(mPEG(10,000)carbamoyl-propyl)-fluorene-N-hydroxysuccinimide" or "4,7-CAC-PEG2-FMOC-NHS 20K"]

The reaction parameters were set up according to Table 4. The polymeric reagents were dissolved in 2 mM HCl (100 mg/ml) and used immediately. Each portion of PEG reagent was added every 30 minutes. The concentration of 5'-AminoC6 double-stranded (SEQ ID NO: 183:SEQ ID NO: 192) or single stranded siRNA (SEQ ID NO: 183) in the reaction solution was 28 µM. The reaction mixtures were incubated at ambient temperature (22 C) with stirring. At 3 hours, 10 µl reaction mixtures were mixed with 2.5 µl 0.2 M glycine (unbuffered) to quench the reaction. The reaction mixtures were analyzed by 20% non-denaturing PAGE and 4-20% native PAGE gels. See FIG. 3, FIG. 4, FIG. 5A and FIG. 5B.

TABLE 4

Reaction Parameters for Examples 3a-3f

| Example | Polymeric Reagent 100 mg/mL, µl | 500 mM EPPS buffer, pH 8.5, µl | siRNA | RNAse free water (µl) | Total volume (µl) | Ratio |
| --- | --- | --- | --- | --- | --- | --- |
| 3a | m-PEG2-RU-NHS 20K, 85%, 20 µl × 4 (340 nmole) | 40 | ds-5' AminoC6, 0.28 mM in siRNA buffer, 20 µl (5.6 nmole) | 60 | 200 | 60:1 |

TABLE 4-continued

Reaction Parameters for Examples 3a-3f

| Example | Polymeric Reagent 100 mg/mL, µl | 500 mM EPPS buffer, pH 8.5, µl | siRNA | RNAse free water (µl) | Total volume (µl) | Ratio |
|---|---|---|---|---|---|---|
| 3b | m-PEG2-RU-NHS 20K, 85%, 20 µl × 4 (336 nmole) | 40 | ss-5' AminoC6, 1.0 mM in siRNA buffer, 5.6 µl (5.6 nmole) | 74.4 | 200 | 60:1 |
| 3c | mPEG-SC 20K, 85%, 20 µl × 4 (340 nmole) | 40 | ds-5' AminoC6, 0.28 mM in siRNA buffer, 20 µl (5.6 nmole) | 60 | 200 | 60:1 |
| 3d | mPEG-SC 20K, 85%, 20 µl × 4 (340 nmole) | 40 | ss-5' AminoC6, 1.0 mM in siRNA buffer, 5.6 µl (5.6 nmole) | 74.4 | 200 | 60:1 |
| 3e | 4,7-CAC-mPEG-FMOC-NHS, 87%, 20 µl × 4 (340 nmole) | 40 | ds-5' AminoC6, 0.28 mM in siRNA buffer, 20 µl (5.6 nmole) | 60 | 200 | 60:1 |
| 3f | 4,7-CAC-PEG2-FMOC-NHS, 87% 20 µl × 4 (340 nmole) | 40 | ss-5' AminoC6, 1.0 mM in siRNA buffer, 5.6 µl (5.6 nmole) | 74.4 | 200 | 60:1 |

Figure 3:
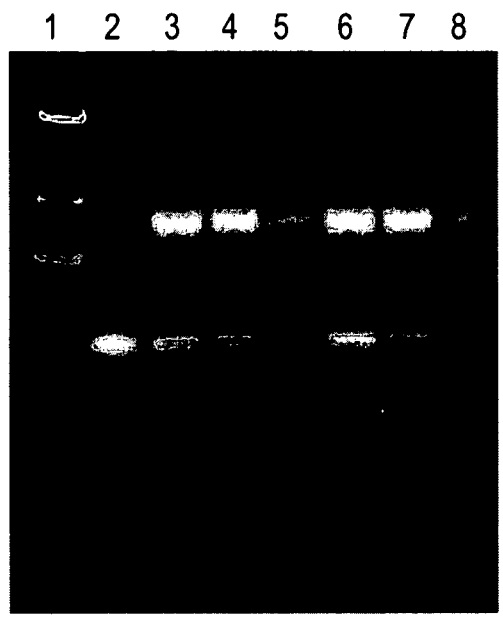
FIG. 3, FIG. 4, FIG. 5A and FIG. 5B are representations of gel as further described in Examples 3a-3f.
Figure 4:

A gel is provided in FIG. 3, showing native 20% PAGE 5'-aminoC6 ds-siRNA+indicated polymeric reagent (60×) comparisons with 5'-aminoC6 ss-siRNA at pH 8.5 in 100 mM EPPS buffer for three hours. Lane 1 corresponds to a 10 bp DNA ladder, lane 2 corresponds to ds-siRNA-m-PEG2-RU-NHS 20K conjugate, 1 and 3 corresponds to ss-siRNA-m-PEG2-RU-NHS conjugate, lane 4 corresponds to ds-siRNA-m-PEG-SC 20K conjugate, lane 5 corresponds to ss-siRNA-m-PEG-SC 20K conjugate, lane 6 corresponds to ds-siRNA-CAC 20K conjugate, lane 7 corresponds to ss-siRNA-4,7-CAC 20K conjugate (although the bands crossed over to lane 6). The conversion yields of ds-siRNA conjugation were estimated with density scanning: all were roughly 50%. FIG. 4 represents the gel of FIG. 3 stained with iodine, thereby showing the PEG components.

Figure 5A:
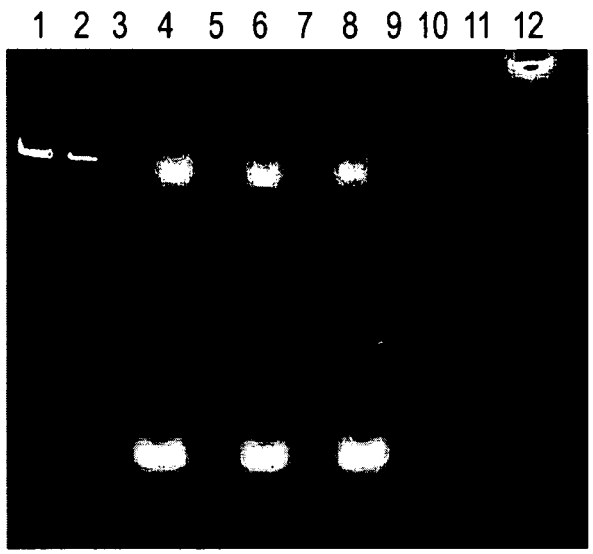
Figure 5B:
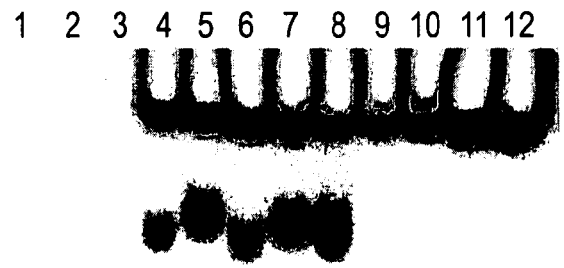

A gel is provided in FIG. 5A, showing igure native 4-20% gradient PAGE 5'-aminoC6 double-stranded siRNA+indicated polymeric reagent comparisons with 5'-aminoC6 siRNA sense strain at pH 8.5 in 100 mM EPPS buffer for three hours. Lanes 1 and 2 correspond to a 10 bp DNA ladder, lane 3 corresponds to ds-siRNA, lane 4 corresponds to ds-siRNA-m-PEG2-RU-NHS 20K conjugate, lane 5 corresponds to ss-siRNA-m-PEG2-RU-NHS 20K conjugate, lane 6 corresponds to ds-siRNA-m-PEG-SC 20K conjugate, lane 7 corresponds to ss-siRNA-m-PEG-SC 20K conjugate, lane 8 corresponds to ds-siRNA-4,7-CAC 20K conjugate, lane 9 corresponds to ss-siRNA-4,7-CAC 20K conjugate (although the bands crossed over to lane 6), lane 10 corresponds to mPEG2-RU-NHS 20K, lane 11 corresponds to mPEG-SC 20K, lane 12 corresponds to CAC 20K. Conversion yields of ds-siRNA conjugation were estimated by density scanning: all were roughly 50%. FIG. 5B represents the gel of FIG. 5A stained with iodine, thereby showing the PEG components.

Figure 6A:
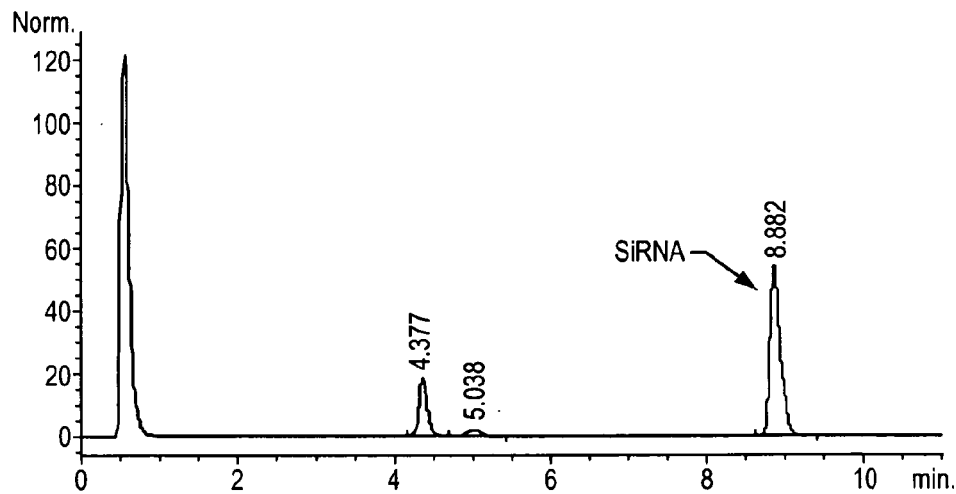
FIG. 6A, FIG. 6B and FIG. 6C are representations of chromatograms as further described in Examples 3a-3f.
Figure 6B:
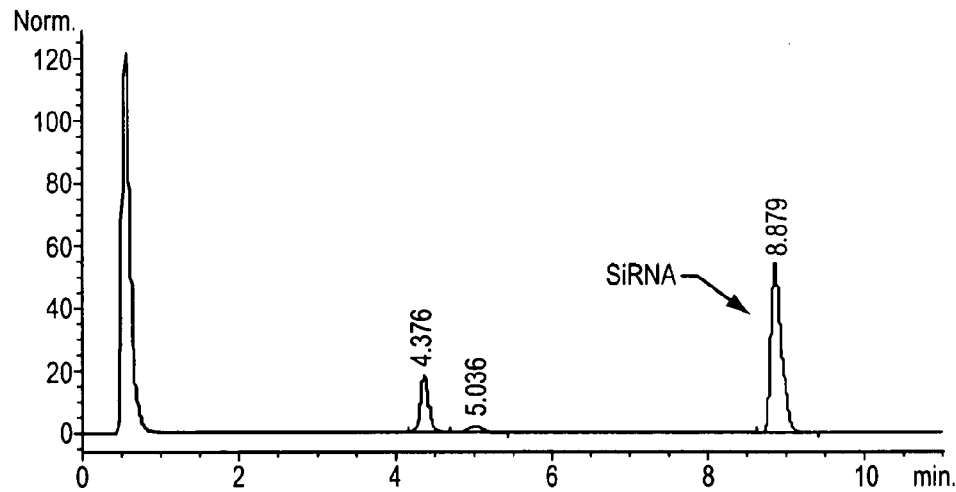
Figure 6C:
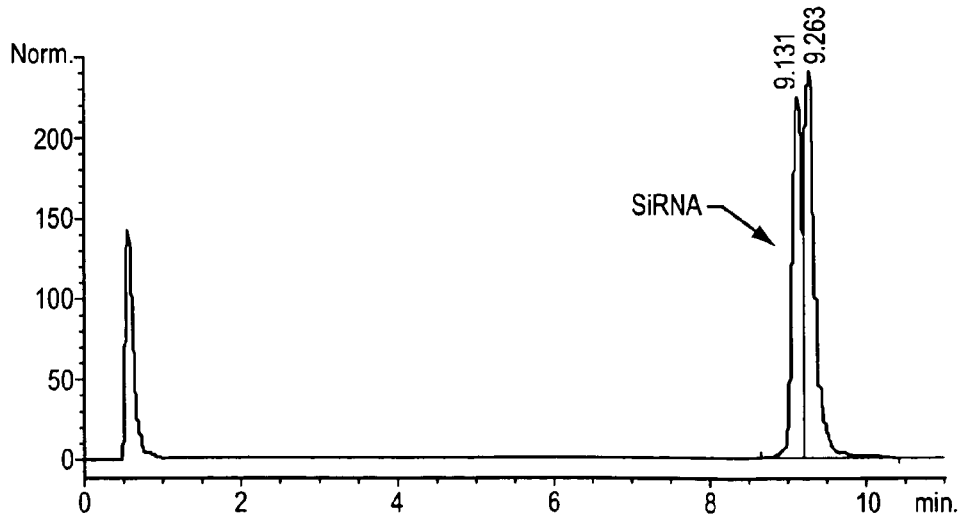

Single stranded siRNA conjugation mixtures were analyzed by RP-HPLC (reversed phase-high performance liquid chromatography), results shown in FIG. 6A, FIG. 6B and FIG. 6C, wherein the chromatogram provided in FIG. 6A corresponds to the product resulting from the reaction parameters for Example 3b, 74% conversion, FIG. 6B corresponds to the product resulting from the reaction parameters for Example 3d, 63.8% conversion, and FIG. 6C corresponds to the product resulting from the reaction parameters for Example 3f, complete conversion detected.

Example 4

Conjugation of 5'AminoC6 Tetramer with m-PEG2-RU-NHS 20K "Reversed-Urethane Branched PEG NHS 20K"

Figure 7:
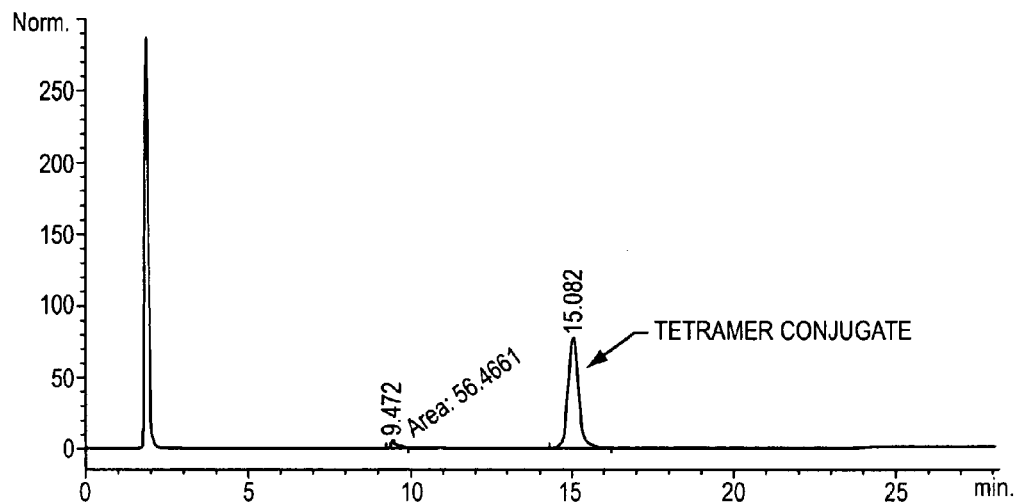
FIG. 7 is a representation of a chromatogram as further described in Example 4.

EPPS buffer (500 mM) was prepared at pH 8.5. A stock solution (14.723 mM) of 5'-aminoC6 ACAA tetramer (Trilink Biotechnology, San Diego, Calif.) was prepared in 1×siRNA buffer (diluted from 5×siRNA buffer, pH 7.5, Dharmacon, Lafayette, Colo.). The reaction was run by dissolution of the indicated polymeric reagent (36.8 mg, 85%) in a mixture of siRNA stock solution (10 µl) and the indicated EPPS buffer (500 mM, 490 µl). The reaction mixture was stirred and incubated at room temperature for three hours. Aliquot (2 µl) was taken, quenched with 0.1 M glycine (2 µl) and diluted with RNAse free water. The sample was analyzed on RP-HPLC, wherein the chromatogram provided in FIG. 7 corresponds to this example and shows a conversion yield of 97%.

Examples 5a and 5b

Conjugation of ss-siRNA with m-PEG-SC 20K ["mPEG Succinimido Carbonate 20K"]

Figure 8:
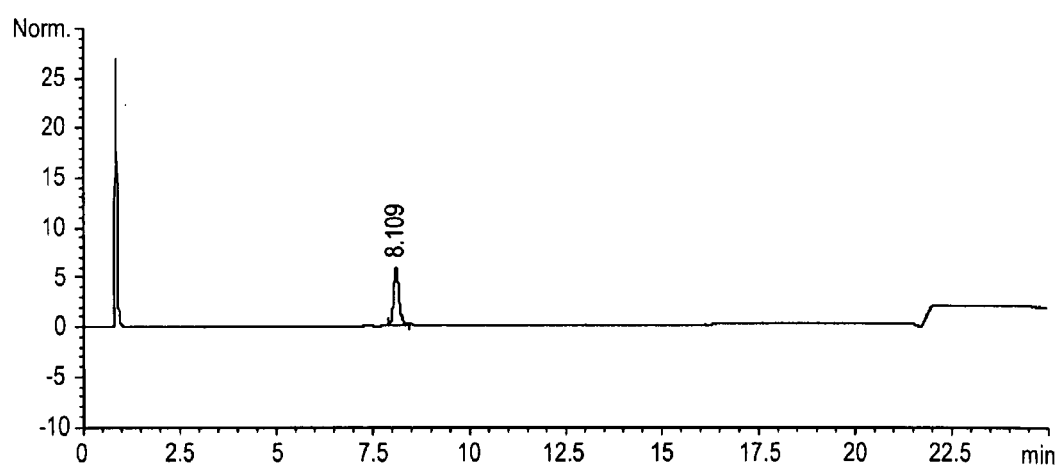
FIG. 8 is a representation of a chromatogram as further described in Examples 5a and 5b and FIG. 9 is a representation of mass spectrometry results as further described in Examples 5a and 5b.
Figure 9:
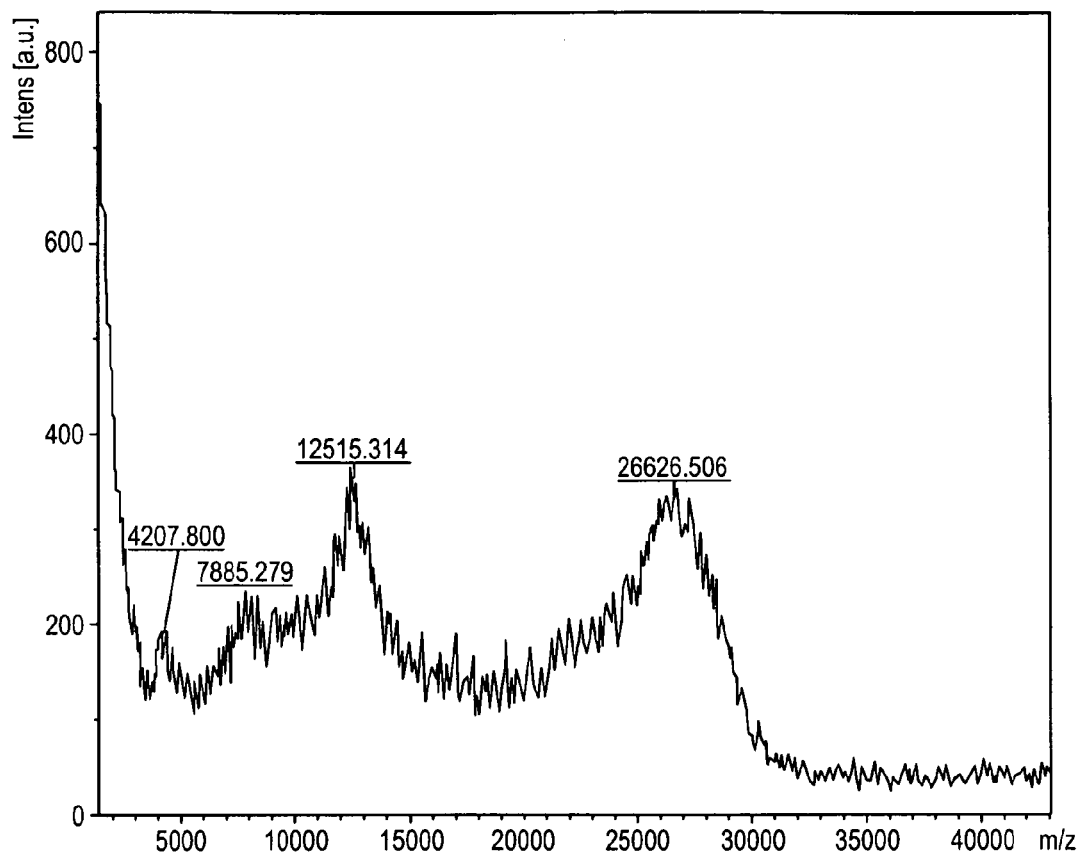

The mPEG reagent was dissolved in 2 mM HCl (100 mg/ml) and used immediately. A stock solution (10.0 mM) of 5'-AminoC6 siRNA sense strain (SEQ ID NO: 183) (Trilink Biotechnology, San Diego, Calif.) was prepared. The reaction was conducted using the reaction parameters set forth in Table 5. The reaction mixtures were incubated at ambient temperature (22° C.). At 15, 30, 60, 90 minutes, 2 µl reaction mixtures were mixed with 2 µl 0.2 M glycine (unbuffered) to quench the reaction. The samples were analyzed via RP-HPLC (results provided in Table 6). The reaction mixture was subjected to purification on FPLC system equipped with Hi-Trap Q HP anion-exchange cartridge. Pure conjugate was obtained, as shown in the chromatogram provided in FIG. 8 while FIG. 9 provides mass spectrometry results (MALDI-MS) of the m-PEG-SC-(ss-siRNA) conjugate.

TABLE 5

Reaction Parameters for Example 5a and Example 5b

|  | Example 5a | Example 5b |
| --- | --- | --- |
| m-PEG-SC 20K (90%, 100 mg/ml), µl | 14.12 | 28.24 |
| ss-siRNA (96%, 10 mM), µl | 1 | 1 |
| EPPS buffer (1M, pH 8.5), µl | 3.33 | 3.33 |
| RNAse free water, µl | 14.88 | 0.76 |
| Total Volume, µl | 33.33 | 33.33 |
| Ratio | 6:1 | 12:1 |

TABLE 6

Results at Time Points 15, 30, 60 and 90 minutes for Example 5a and Example 5b

| Time | Conversion Yield, % | |
| --- | --- | --- |
| Point (minutes) | Example 5a 6:1 | Example 5b 12:1 |
| 15 | 49.0 | 67 |
| 30 | 59.3 | 76.8 |
| 60 | 64.0 | 85.4 |
| 90 | 63.3 | 88.0 |

Example 6

Conjugation of ss-siRNA with CAC 20K Polymeric Reagent "4,7-CAC-PEG2-FMOC-NHS 20K"

Figure 10:
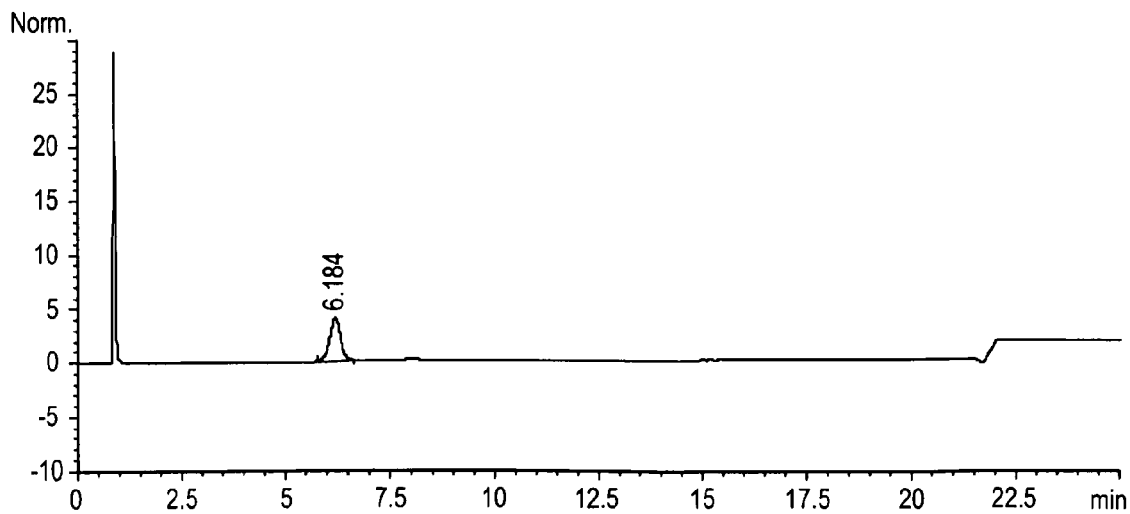
FIG. 10 is a representation of a chromatogram as further described in Example 6.
Figure 11:
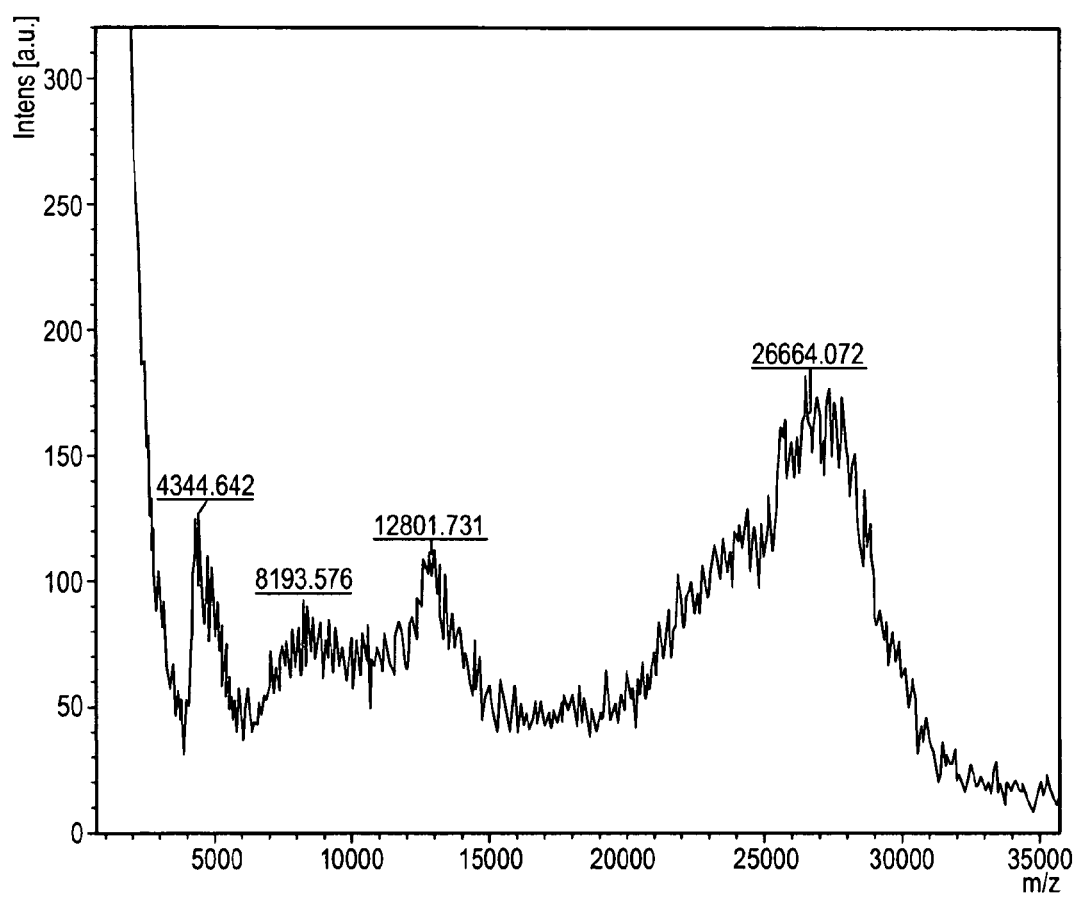
FIG. 11 is a representation of mass spectrometry results as further described in Example 6.

The reaction was conducted in a manner similar to those of the previous examples, using the reaction parameters set forth in Table 7. The reaction mixtures were incubated at ambient temperature (22° C.). At 15, 30, 60, 90, and 180 minutes, 2 µl reaction mixtures were mixed with 2 µl 0.2 M glycine (unbuffered) to quench the reaction. The samples were analyzed on RP-HPLC (results provided in Table 8). The reaction mixture was subjected to purification on FPLC system equipped with Hi-Trap Q HP anion-exchange cartridge. The pure product was obtained. The RP-HPLC chromatogram of the product is provided in FIG. 10 while FIG. 11 provides mass spectrometry results (MALDI-MS) of the CAC-(ss-siRNA) conjugate.

TABLE 7

Reaction Parameters for Example 6a and Example 6b

|  | Example 6a | Example 6b |
| --- | --- | --- |
| CAC 20K (90%, 100 mg/ml), µl | 14.12 | 28.24 |
| ss-siRNA (96%, 10 mM), µl | 1 | 1 |
| EPPS buffer (1M, pH 8.5), µl | 3.33 | 3.33 |
| RNAse free water, µl | 14.88 | 0.76 |
| Total Volume, µl | 33.33 | 33.33 |
| Ratio | 6:1 | 12:1 |

TABLE 8

Results at Time Points 15, 30, 60, 90 and 180 minutes for Example 6a and Example 6b

| Time | Conversion Yield, % | |
| --- | --- | --- |
| Point (minutes) | Example 6a 6:1 | Example 6b 12:1 |
| 15 | 37.8 | 54.0 |
| 30 | 50.3 | 69.1 |
| 60 | 55.0 | 77.8 |
| 90 | 56.3 | 80.4 |
| 180 | 56.4 | 79.6 |

Figure 12:
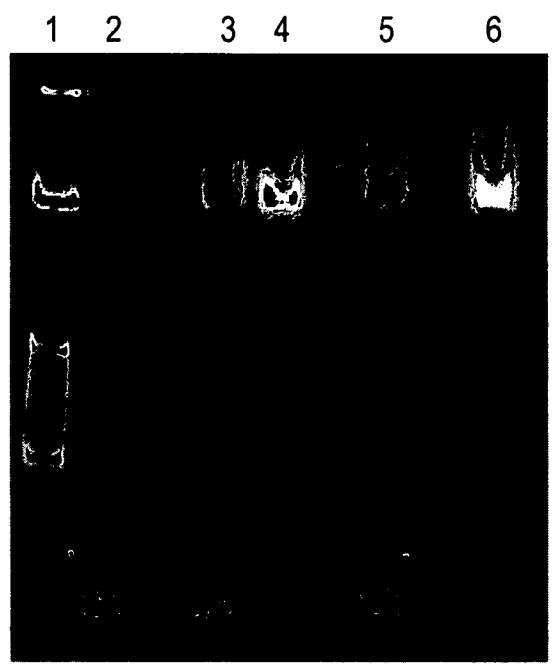
FIG. 12 is a representation of a gel as further described in Example 6.

Further analysis via a native gel analysis for the reaction conducted for 180 minutes were performed by mixing 0.5 µl of the reaction mixture with 1 µl 0.2 M glycine (unbuffered) to quench the reaction. The reaction mixtures were analyzed by 4-20% native PAGE gel as shown in FIG. 12. In FIG. 12, lane 1 corresponds to a 10 bp DNA ladder, lane 2 corresponds to ss-siRNA, lane 3 corresponds to m-PEG-SC 20K-ss-siRNA conjugate (6:1), lane 4 corresponds to m-PEG-SC 20K-ss-siRNA conjugate (12:1), lane 5 corresponds to CAC 20K-ss-siRNA (6:1) conjugate, lane 6 corresponds to CAC 20K-ss-siRNA conjugate (12:1).

Example 7

PEGylation and Purification of CAC 20K-ssRNA Conjugate "CAC-PEG2-FMOC-20K-ssRNA Conjugate"

Figure 13:
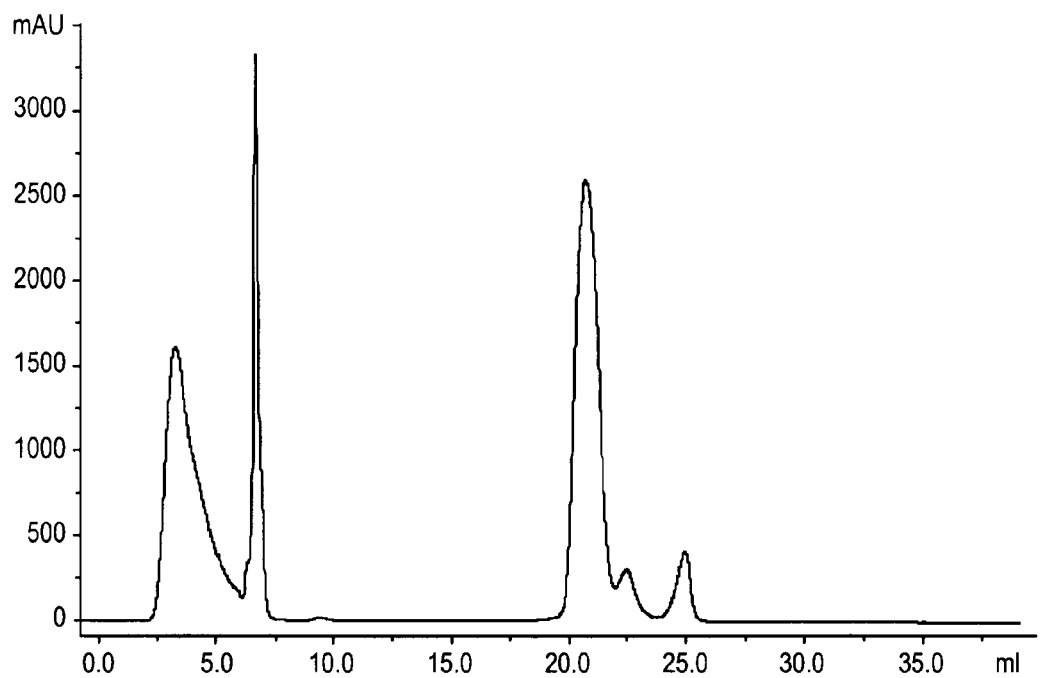
FIG. 13 is a representation of a chromatogram as further described in Example 7.

CAC-ssRNA conjugate was produced in a 0.3-mL reaction mixture consisting of 0.030 mL 1 M EPPS buffer, pH 8.5, 0.009-ML 10 mM ssRNA (sequence: 5'-C6-$NH_2$—AmCA-mACmAGmACmUUmUAmAUmGUmAA-3', SEQ ID NO: 183) and 0.261 ml of 100 mg/mL CAC 20K polymeric reagent. The CAC 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris buffer, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (5 column volumes). The linear gradient consisted of 10 to 80% of the buffer B over the twenty column volumes at the elution flow rate of 1 mL/min. The chromatogram of the reaction mixture is provided in FIG. 13. The concentration of the conjugate was determined by UV spectrophotometry. The purity of the conjugate was confirmed by ion-exchange HPLC. MALDI-TOF analysis was performed to confirm the molecular weight of the conjugate.

Example 8

PEGylation and Purification of CG 20K-ssRNA Conjugate "CG-PEG2-FMOC-20K-ssRNA conjugate"

Figure 14:
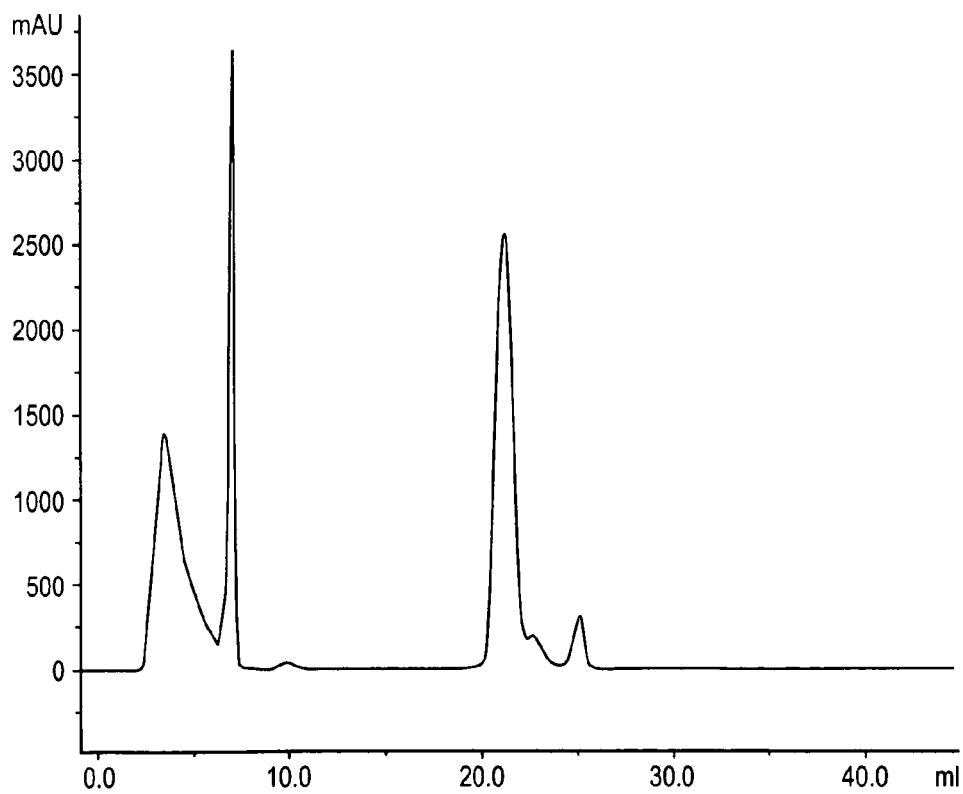
FIG. 14 is a representation of a chromatogram as further described in Example 8.

CG 20K-ssRNA conjugate was produced in a 0.3-mL reaction mixture consisting of 0.030 mL 1 M EPPS buffer, pH 8.5, 0.009-ML 10 mM ssRNA (sequence: 5'-C6-NH$_2$— AmCAmACmAGmACmUUmUAmAUmGUmAA-3', SEQ ID NO: 183) and 0.261 ml of 100 mg/mL CG 20K polymeric reagent. The CG 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-ML with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow ratio 1 mL/min and then the column was washed with the buffer A (5 column volumes). The linear gradient consisted of 10 to 80% of the buffer B over the twenty column volumes at the elution flow rate of 1 mL/min. The chromatogram of the reaction mixture is provided in FIG. 14. The concentration of the conjugate was determined by UV spectrophotometry. The purity of the conjugate was determined by ion-exchange HPLC. MALDI-TOF analysis was performed to confirm the molecular weight of the conjugate.

Example 9

PEGylation and Purification of C2 20K-ssRNA Conjugate "C2-PEG2-FMOC 20K-ssRNA Conjugate"

Figure 15:
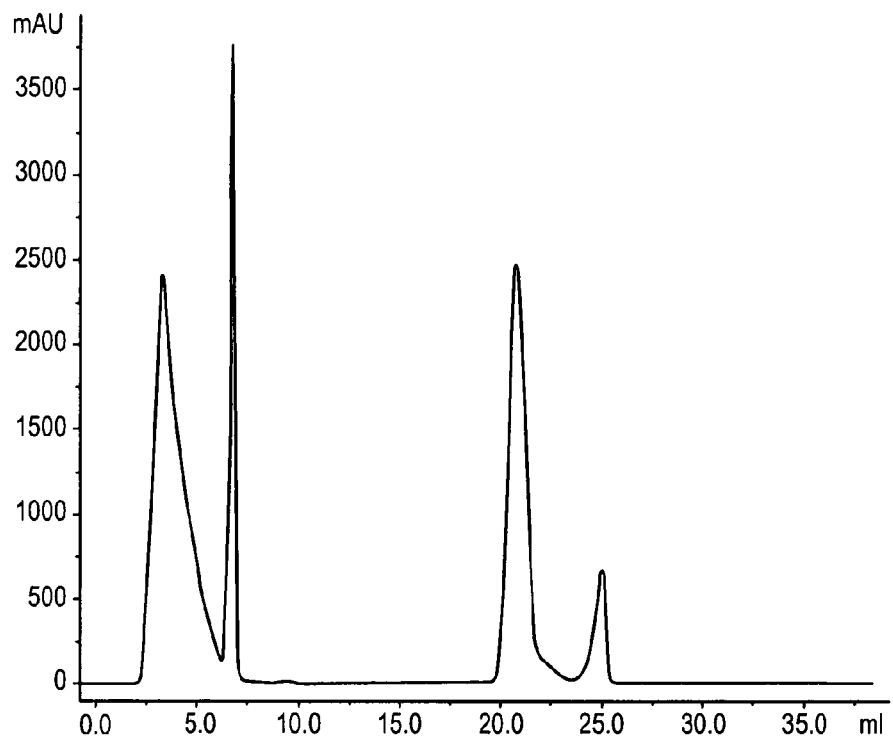
FIG. 15 is a representation of a chromatogram as further described in Example 9.

C2 20K-ssRNA conjugate was produced in a 0.3-mL reaction mixture consisting of 0.030 mL 1 M EPPS buffer, pH 8.5, 0.009-ML 10 mM ssRNA (sequence: 5'-C6-NH$_2$— AmCAmACmAGmACmUUmUAmAUmGUmAA-3', SEQ ID NO: 183) and 0.261 ml of 100 mg/mL C2 20K polymeric reagent. The C2 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow ratio 1 mL/min and then the column was washed with a 5 column volume of the buffer A. The linear gradient consisted of 10 to 80% of the buffer B over the twenty column volumes at the elution flow rate of 1 mL/min. The chromatogram of the reaction mixture is provided in FIG. 15. The concentration of the conjugate was determined by UV spectrophotometry. The purity of the conjugate was confirmed by ion-exchange HPLC. MALDI-TOF analysis was performed to confirm the molecular weight of the conjugate.

Example 10

Figure 16:
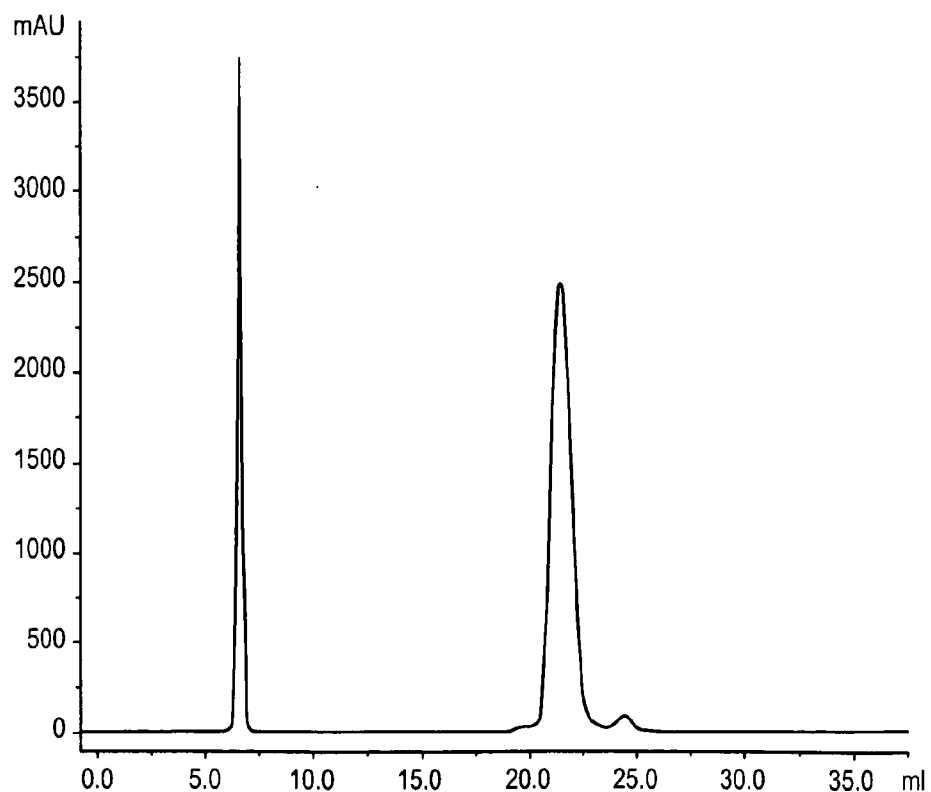
FIG. 16 is a representation of a chromatogram as further described in Example 10.

PEGylation and Purification of m-PEG-SS 20K-ssRNA Conjugate m-PEG-SS 20K-ssRNA conjugate was produced in a 0.3-mL reaction mixture consisting of 0.030 mL 1 M EPPS buffer, pH 8.5, 0.009-ML 10 mM ssRNA (sequence: 5'-C6-NH$_2$— AmCAmACmAGmACmUUmUAmAUmGUmAA-3', SEQ ID NO: 183) and 0.261 ml of 100 mg/mL m-PEG-SS 20K polymeric reagent. The m-PEG-SS 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (5 column volumes). The linear gradient consisted of 10 to 80% of the buffer B over the twenty column volumes of the eluate at an elution flow rate of 1 mL/min. The chromatogram of the reaction mixture is provided in FIG. 16. The concentration of the conjugate was determined by UV spectrophotometry. The purity of the conjugate was confirmed by ion-exchange HPLC. MALDI-TOF analysis was performed to confirm the molecular weight of the conjugate.

Example 11

Figure 17:
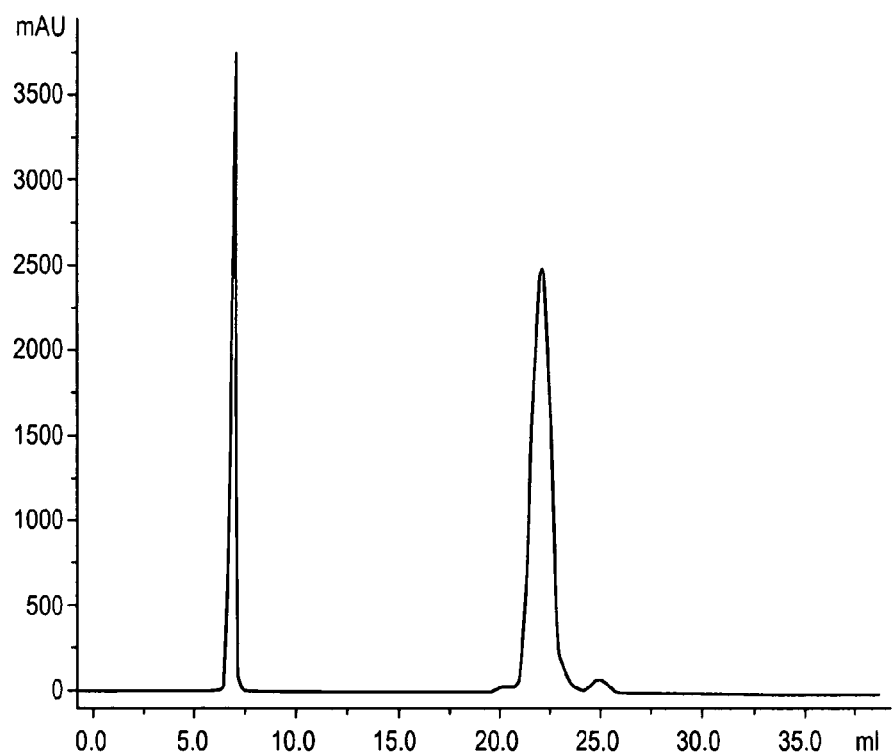
FIG. 17 is a representation of a chromatogram as further described in Example 11.

PEGylation and Purification of m-PEG-SBC 30K-ssRNA Conjugate m-PEG-SBC 30K-ssRNA conjugate was produced in a 0.3-mL reaction mixture consisting of 0.030 mL 1 M EPPS buffer, pH 8.5, 0.009-mL 10 mM ssRNA (sequence: 5'-C6-NH$_2$— AmCAmACmAGmACmUUmUAmAUmGUmAA-3', SEQ ID NO: 183) and 0.261 ml RNAse free water. The m-PEG-SBC 30K polymeric reagent (31.5 mg) was added into the RNA with three portions within 20 minutes. After the last addition of the m-PEG-SBC 30K reagent, the reaction mixture was further incubated at 25° C. for 20 minutes; then 0.05 mL 0.4 M glycine (unbuffered) was added into the reaction mixture to quench the unreacted polymeric reagent. After an additional 30 minutes of incubation at 25° C., the reaction mixture was diluted to a final volume of 1-mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (5 column volume). The linear gradient consisted of 10 to 80% of the buffer B over the twenty column volumes of the eluate at an elution flow rate of 1 mL/min. The chromatogram of the reaction mixture is provided in FIG. 17. The concentration of the conjugate as determined by UV spectrophotometry. The purity of the conjugate was confirmed by ion-exchange HPLC. MALDI-TOF analysis was performed to confirm the molecular weight of the conjugate Example 12

Figure 18:
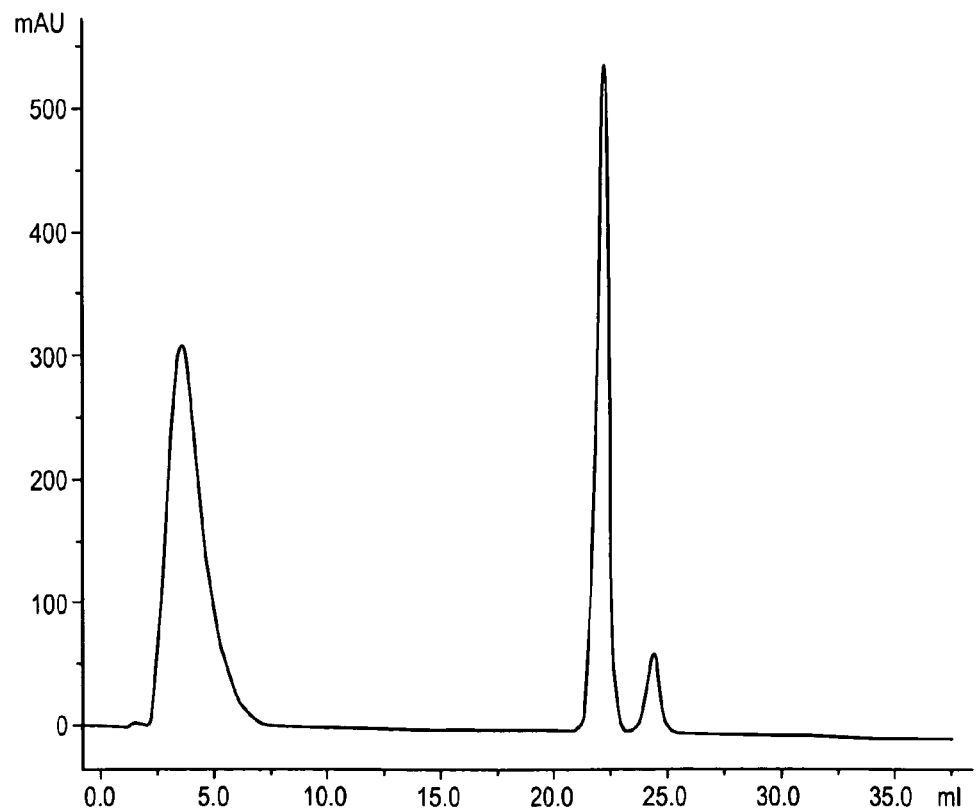
FIG. 18 is a representation of a chromatogram as further described in Example 12.

PEGylation and Purification of m-PEG-OPSS 5K-ssRNA Conjugate m-PEG-OPSS 5K-ssRNA conjugate was produced by the reduction of 5'capped-RNA (5'-C6-S-SC6-AmCAmACmAGmACmUUmUAmAUmGUmAA-3', SEQ ID NO: 186) with Tris(2-Carboxyethyl)phosphine hydrochloride (TCEP HCl) followed by PEGylation with m-PEG-OPSS 5K. To reduce 5'-capped-RNA, a 0.03 mL solution containing 0.002 mL of 5'capped-RNA, 0.006 mL, 1 M, EPPS buffer, pH 8.5 and 0.022-mL 18 mM TCEP.HCl was incubated at 25° C. without stirring for 60 minutes. After 60 minutes incubation, 0.03 mL reaction mixture was loaded on a desalting column (pre-equilibrated with 20 mM HEPES, 50 mM NaCl, pH 7.4) and rinsed with 0.03 mL buffer (20 mM HEPES, 50 mM NaCl, pH 7.4). A total of 0.06 mL solution containing RNA with free thiol group (5'-HSC6-AmCAmACmAGmAC-mUUmUAmAUmGUmAA-3' (SEQ ID NO: 195)) was collected. To PEGylate free thiol-ss-RNA, 7.2 mg m-PEG-OPSS 5K was added into the 0.06-ML solution containing RNA with free thiol group. After incubation at 25° C. without stirring for three hours, the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow ratio 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 18. The concentration of the conjugate was determined by UV spectrophotometry. The purity of the conjugate was confirmed by ion-exchange HPLC. MALDI-TOF analysis was performed to confirm the molecular weight of the conjugate.

Example 13

PEGylation and Purification of Di-C2 20K-ssRNA Conjugate [or "Di-C2-mPEG2-FMOC-20K-ssRNA conjugate"]

Figure 19:
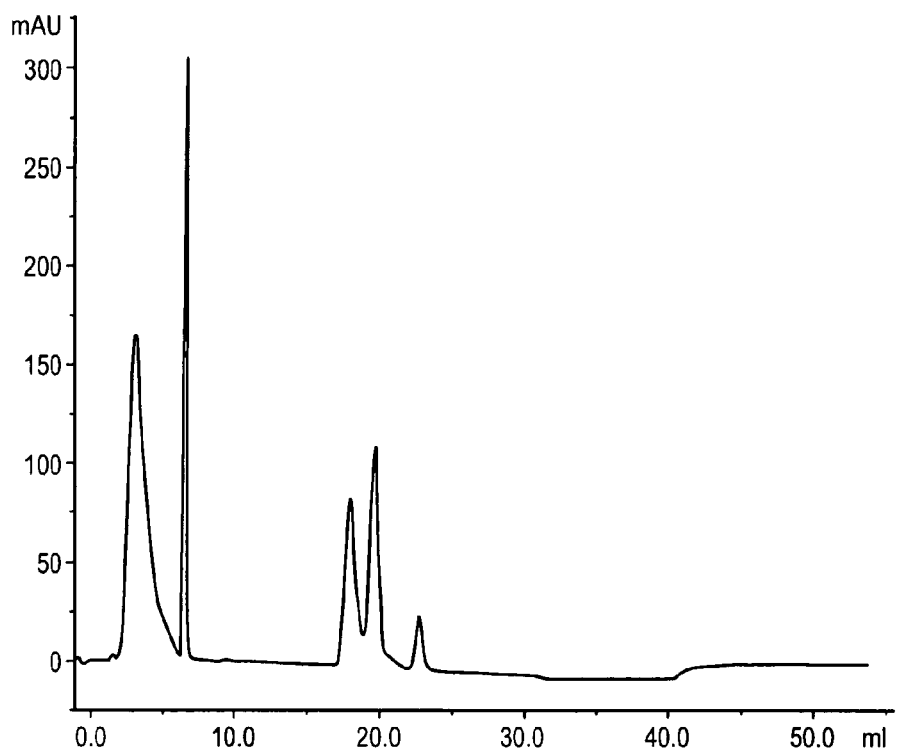
FIG. 19 is a representation of a chromatogram as further described in Example 13.

Di-C2 20K-ssRNA conjugate was produced in a 0.033 mL reaction mixture consisting of 0.003 mL 1 M EPPS buffer, pH 8.5, 0.001 mL 10 mM ssRNA (sequence: 5'-C6-NH$_2$—AmCAmACmAGmACmUUmUAmAUmGUmAA C6 SEQ ID NO: 183) and 0.0281 ml of 100 mg/mL C2 20K polymeric reagent. The C2 20K reagent, the last reactive component added to the mixture, was dissolved in RNAse-free water to a final concentration of 100 mg/mL immediately before use. The reaction mixture was incubated at 25° C. without stirring for 60 minutes. After 60 minutes, 0.005 mL 0.4 M glycine (unbuffered) was added into the reaction mixture to quench the unreacted polymeric reagent. After an additional 30 minutes of incubation at 25° C., the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 19. The concentration of the conjugate was determined by UV spectrophotometry. The purity of the conjugate was confirmed by ion-exchange HPLC. MALDI-TOF analysis was performed to confirm the molecular weight of the conjugate.

Example 14

Figure 20:
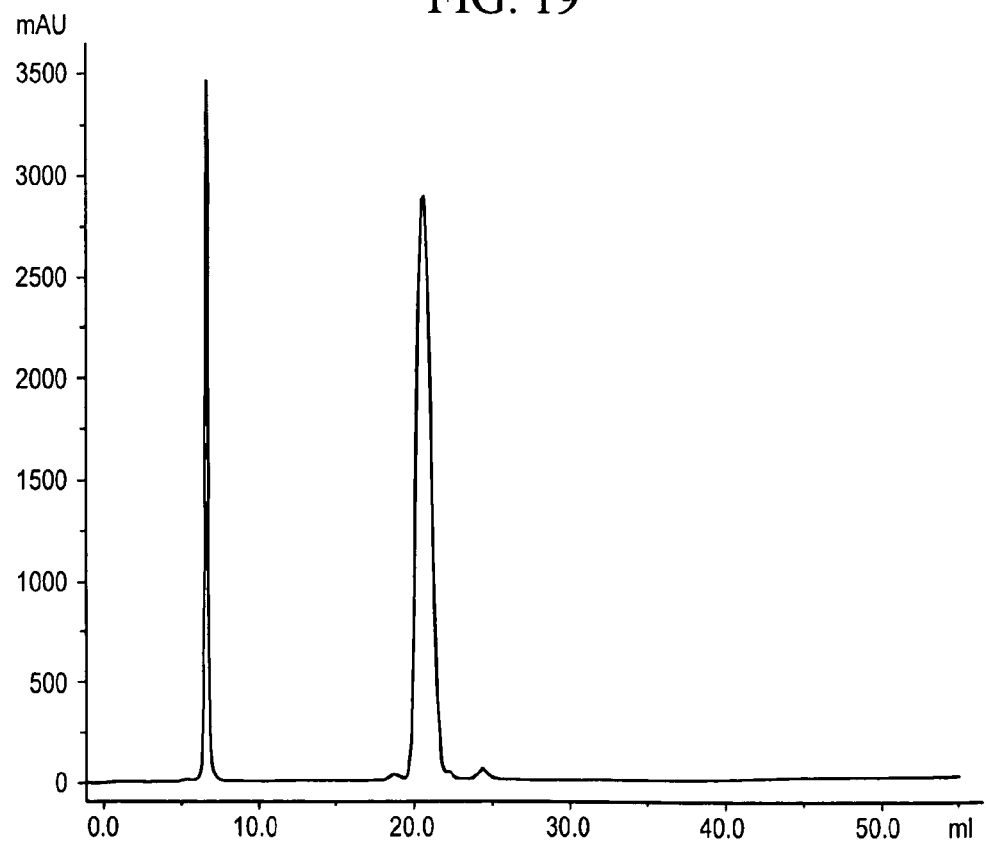
FIG. 20 is a representation of a chromatogram as further described in Example 14.

PEGylation and Purification of m-PEG2-RU-NHS 20K-ssRNA Conjugate [or "ruPEG2-20K-ssRNA Conjugate]

m-PEG2-RU-NHS 20K-ssRNA conjugate was produced in a 0.3 mL reaction mixture consisting of 0.030 mL 1 M EPPS buffer, pH 8.5, 0.009 mL 10 mM ssRNA (sequence: 5'-C6-NH$_2$—AmCAmACmAGmACmUUmUAmAUmGUmAA-3', SEQ ID NO: 183) and 0.261 ml of 100 mg/mL m-PEG2-RU-NHS 20K polymeric reagent. The m-PEG2-RU-NHS 20K reagent, the last reactive component added to the mixture, was dissolved in 2 mM HCl to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 20. The concentration of the conjugate was determined by UV spectrophotometry. The purity of the conjugate was confirmed by ion-exchange HPLC. MALDI-TOF analysis was performed to confirm the molecular weight of the conjugate.

Example 15

Figure 21:
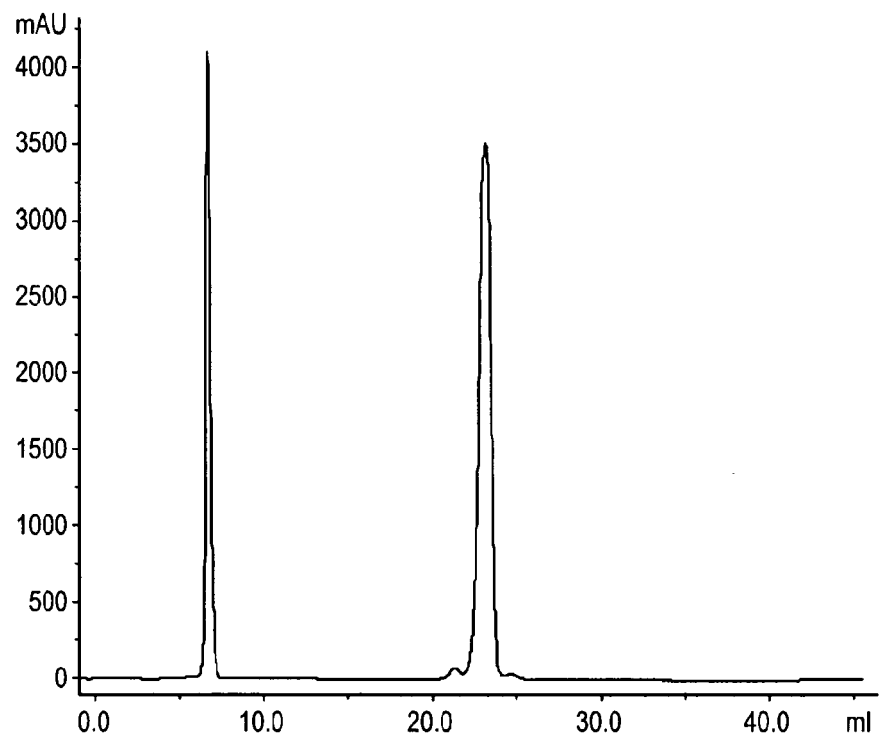
FIG. 21 is a representation of a chromatogram as further described in Example 15.

PEGylation and Purification of mPEG-SBA 5K-ssRNA Conjugate m-PEG-SBA 5K-ssRNA conjugate was produced in a 0.3 mL reaction mixture consisting of 0.030 mL 1 M EPPS buffer, pH 8.5, 0.009 mL 10 mM ssRNA (sequence: 5'-C6-NH$_2$—AmCAmACmAGmACmUUmUAmAUmGUmAA-3', SEQ ID NO: 183) and 0.261 ml of 100 mg/mL m-PEG-SBA 5K polymeric reagent. The m-PEG-SBA 5K reagent, the last reactive component added to the mixture, was dissolved in 2 mM HCl to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1-ML with 20 mM Bis-tris, pH 6.8 and purified by anion exchange chromatography (HiTrap Q HP; 1 mL). A linear salt gradient separated the PEGylated ss-RNA from the unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 21. The concentration of the conjugate was determined by UV spectrophotometry. The purity of the conjugate was confirmed by ion-exchange HPLC. MALDI-TOF analysis was performed to confirm the molecular weight of the conjugate.

Example 16

Figure 22:
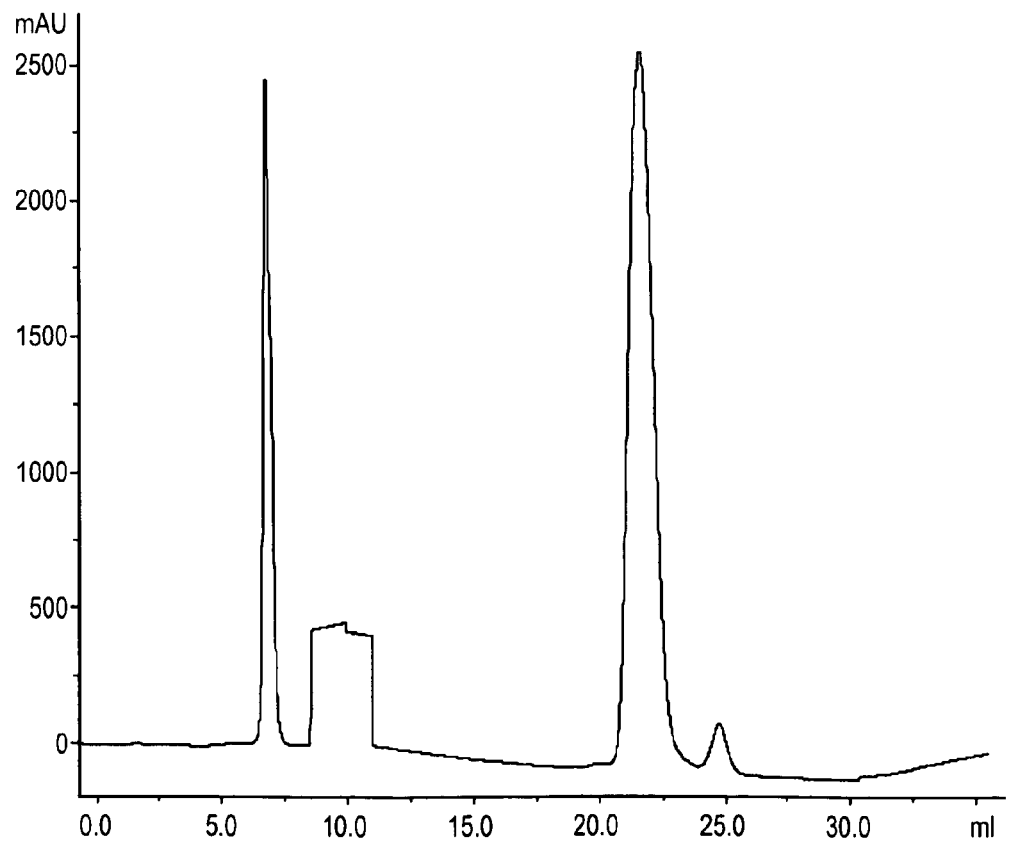
FIG. 22 is a representation of a chromatogram as further described in Example 16.

PEGylation and Purification of m-PEG-SC 20K-ssRNA Conjugate m-PEG-SC 20K-ssRNA conjugate was produced in a 0.3 mL reaction mixture consisting of 0.030 mL 1 M EPPS buffer, pH 8.5, 0.009 mL 10 mM ssRNA (sequence: 5'-C6-NH$_2$—AmCAmACmAGmACmUUmUAmAUmGUmAA-3', SEQ ID NO: 183) and 0.261 ml of 100 mg/mL mPEG-SC 20K polymeric reagent. The mPEG-SC 20K reagent, the last reactive component added to the mixture, was dissolved in 2 mM HCl to a final concentration of 100 mg/mL immediately before use. The reaction mixture was incubated at 25° C. without stirring for 60 minutes. After 60 minutes, 0.05 mL 0.4 M glycine (unbuffered) was added into the reaction mixture to quench the unreacted polymeric reagent. After an additional 30 minutes of incubation at 25° C., the reaction mixture was diluted to a final volume of 1 mL with 20 mM Bis-tris, pH 6.8 and purified by anion exchange chromatography (HiTrap Q HP; 1 mL). A linear salt gradient separated the PEGylated ss-RNA from unreacted polymeric reagent and unreacted ssRNA. Purification buffers were as follows: A: 20 mM Bis-tris, pH 6.8, and B: 20 mM Bis-tris, 1.0 M sodium chloride, pH 6.8. The diluted reaction mixture was loaded at the flow rate 1 mL/min and then the column was washed with the buffer A (a 5 column volume). The linear gradient consisted of 10 to 80% of the buffer B over the twenty column volumes of the eluate at an elution flow rate of 1 mL/min. The chromatogram of the reaction mixture is provided in FIG. 22. The concentration of the conjugate was determined by UV spectrophotometry. The purity of the conjugate was confirmed by ion-exchange HPLC. MALDI-TOF analysis was performed to confirm the molecular weight of the conjugate.

Example 17

Comparison of Conjugates

A comparison of some of the analytical data of the conjugates prepared in Examples 7 through 16 is provided in Table 9. Purity % was determined by anion exchange HPLC while observed molecular weight (MW) was established using MALDI.

Anion exchange HPLC was carried out using a DIONEX BioLC DNAPac PA-10 column (P/N: 043010, Ser#: 007409; Lot#: 008-20-009) having dimensions of 4 mm×250 mm. Flow rate was set at 1.5 mL/min with a column temperature of 25° C. The detection wavelength was 260 nm. Eluent buffer A was 25 mM Tris/0.5% ACN, pH 8.0/HCl and eluent buffer B was 25 mM Tris/0.5% ACN, NH$_4$Cl: 1.6M, pH 8.0/NH$_4$OH. The eluent profile for the approach designated as "IEX-6" is set forth in Table 10a and the eluent profile for the approach designated as "IEX-8" is set forth in Table 10b.

TABLE 9

Comparison of Conjugates Prepared in Example 7 through 16

| Conjugates | Purity (%) | Calculated MW (kD) | Observed MW (kD) |
|---|---|---|---|
| CAC 20K-ssRNA (Example 7) | 97 | 26.3 | 27.7 |
| CG 20K-ssRNA (Example 8) | >99 | 26.3 | 27.3 |
| C2 20K-ssRNA (Example 9) | 97 | 26.3 | 27.8 |
| m-PEG-SS 20K-ssRNA (Example 10) | 93 | 26.3 | 26.8 |
| m-PEG-SBC 30K-ssRNA (Example 11) | 90 | 36.3 | 33.7 |
| m-PEG-OPSS 5K-ssRNA (Example 12) | >99 | 11.3 | 12.2 |
| Di-C2 20K-ssRNA (Example 13) | >99 | 46.3 | 48.7 |
| m-PEG2-RU-NHS 20K-ssRNA (Example 14) | 97 | 26.3 | 27.6 |
| m-PEG-SBA 5K-ssRNA (Example 15) | 93 | 11.3 | 11.9 |
| m-PEG-SC 20K-ssRNA (Example 16) | 92 | 26.3 | 26.7 |

TABLE 10a

Eluent Profile for IEX-6 Approach

| Time (minutes) | A | B |
|---|---|---|
| −10 | 85 | 15 |
| 0 | 85 | 15 |
| 3 | 85 | 15 |
| 20 | 66.5 | 33.5 |
| 20.1 | 0 | 100 |
| 26 | 0 | 100 |
| 26.1 | 85 | 15 |
| 26.2 | Stop | |

TABLE 10b

Eluent Profile for IEX-6 Approach

| Time (minutes) | A | B |
|---|---|---|
| −10 | 95 | 5 |
| 0 | 95 | 5 |
| 3 | 95 | 5 |
| 29.3 | 66.5 | 33.5 |
| 29.4 | 0 | 100 |
| 36.4 | 0 | 100 |
| 36.5 | 95 | 5 |
| 36.6 | Stop | |

Example 18

PEG-ssRNA Conjugate Release Kinetics

NH$_2$—C6-ssRNA Release from C2-PEG2-FMOC-20K-ssRNA Conjugate.

Figure 23:
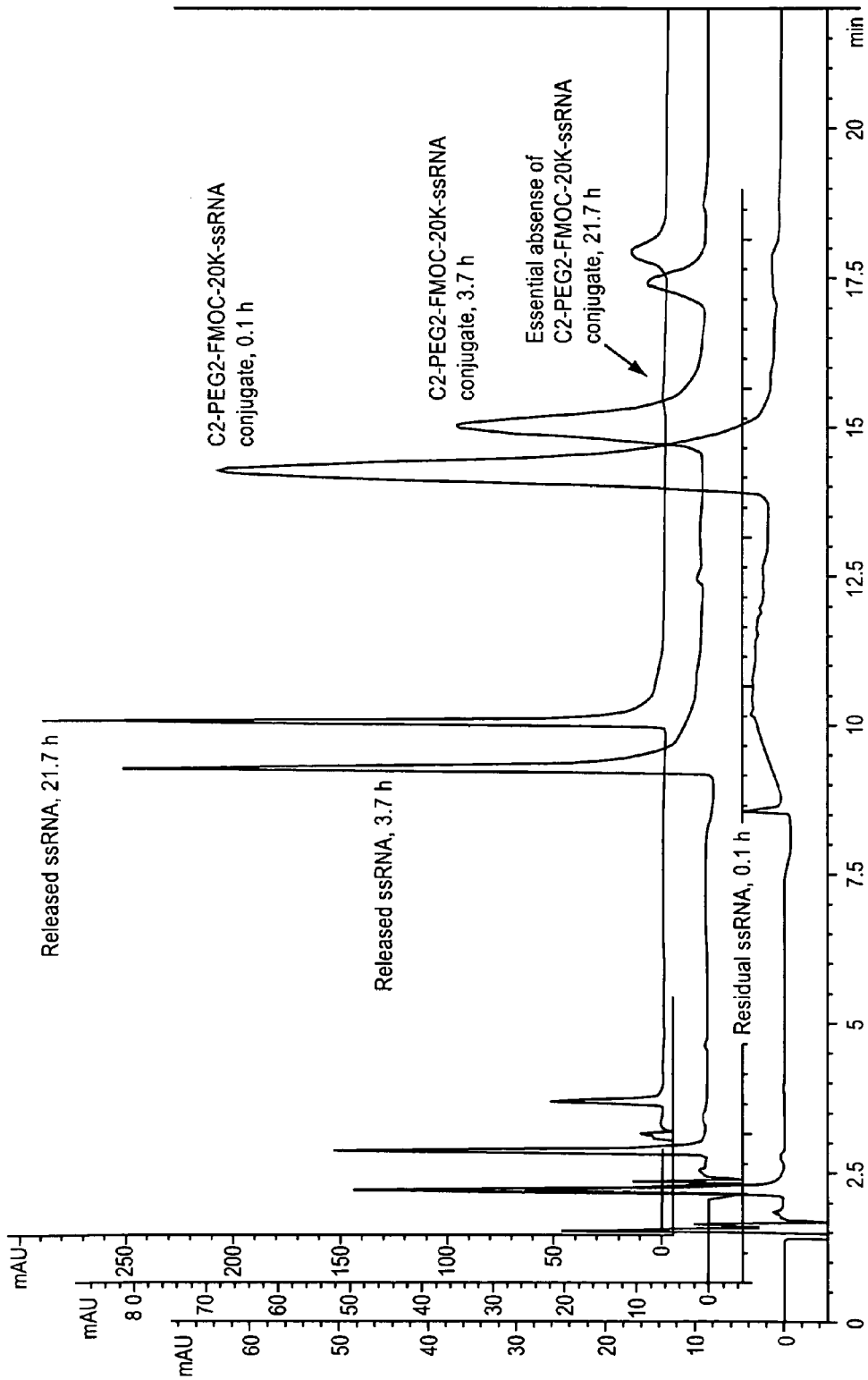
FIG. 23 is a series of chromatograms showing the release of ssRNA from C2-PEG2-FMOC-20K-ssRNA as further described in Example 18.
Figure 24:
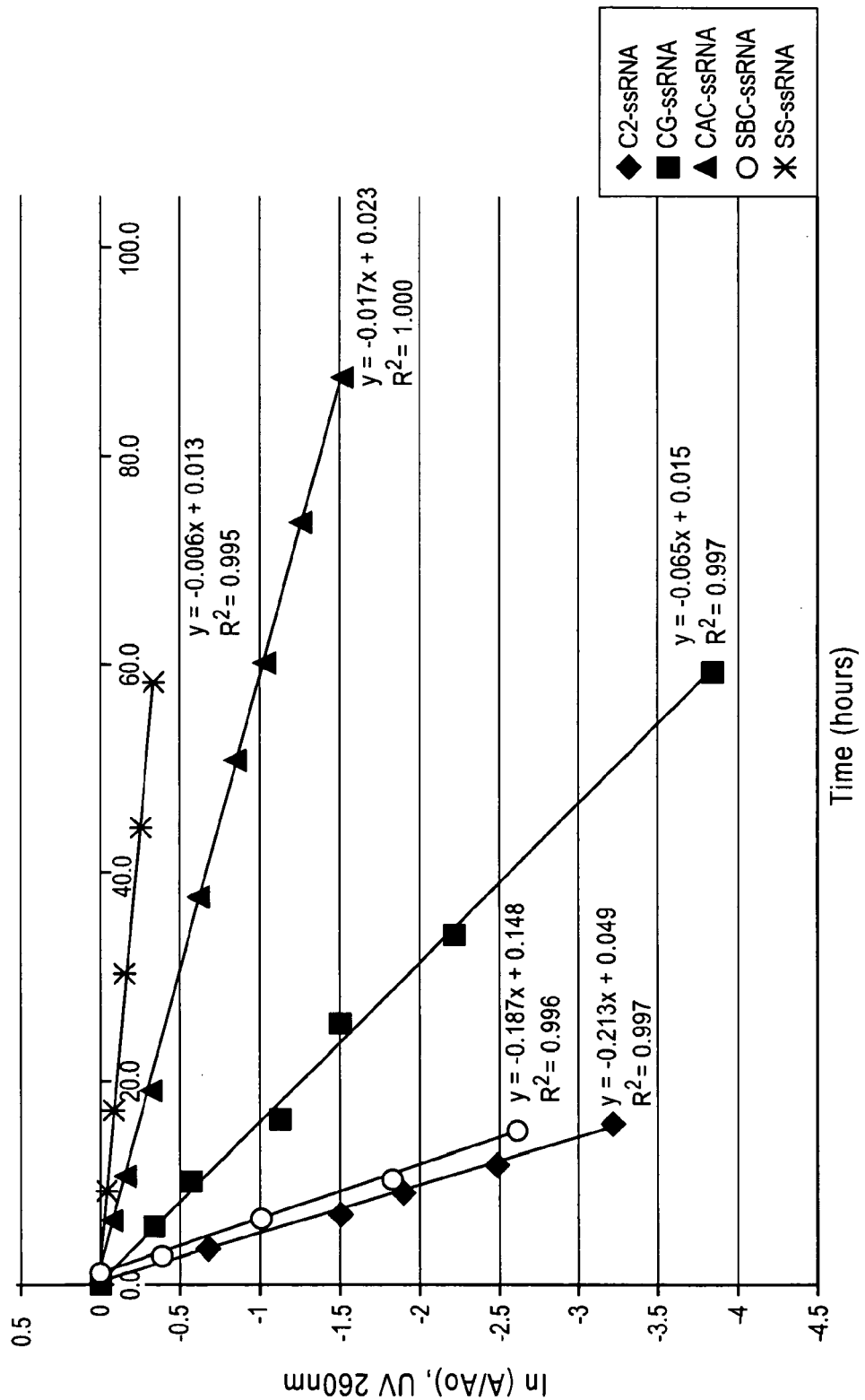
FIG. 24 is a time-concentration plot of PEG-ssRNA conjugates, wherein release kinetics (0.4 M HEPES, pH 7.4, 37° C.) are shown as further described in Example 18.

C2-PEG2-FMOC-20K-ssRNA conjugate, prepared as described in Example 9, 24 µM in 20 mM Bis-Tris buffer, pH 6.8, NaCl solution (50 µL) was combined with 0.6M HEPES buffer, pH 7.5 (100 µL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected (reverse phase HPLC at 260 nm with TEAA water/acetonitrile gradient) at various intervals. Observed results demonstrated a decrease in the PEG-ssRNA conjugate peak with an increase in peaks correlating with released NH$_2$—C6-ssRNA and PEG2-fulvene (see the corresponding chromatograms of FIG. 23). See also the time-concentration plot of FIG. 24 and Table 11.

NH$_2$—C6-ssRNA Release from CG-PEG2-FMOC-20K-ssRNA Conjugate.

CG-PEG2-FMOC-20K-ssRNA conjugate, prepared as described in Example 8, 25 μM in 20 mM Bis-Tris buffer, pH 6.8, NaCl solution (50 μL) was combined with 0.6M HEPES buffer, pH 7.5 (100 μL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected (reverse phase HPLC at 260 nm with TEAA water/acetonitrile gradient) at various intervals. Observed results demonstrated a decrease in the PEG-ssRNA conjugate peak with an increase in peaks correlating with released NH$_2$—C6-ssRNA and PEG2-fulvene. See Table 11 and the time-concentration plot of FIG. 24.

NH$_2$—C6-ssRNA Release from CAC-PEG2-FMOC-20K-ssRNA Conjugate.

CAC-PEG2-FMOC-20K-ssRNA conjugate, prepared as described in Example 7, 24 μM in 20 mM Bis-Tris buffer, pH 6.8, NaCl solution (50 μL) was combined with 0.6M HEPES buffer, pH 7.5 (100 μL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected at various intervals. Observed results demonstrated a decrease in the PEG-ssRNA conjugate peak with an increase in peaks correlating with released NH$_2$—C6-ssRNA and PEG2-fulvene. See Table 11 and the time-concentration plot of FIG. 24.

Succinate modified NH$_2$—C6-ssRNA release from SS-PEG-20K-ssRNA conjugate.

SS-PEG-20K-ssRNA Conjugate, Prepared as Described in Example 10, 25.8 μM in 20 mM Bis-Tris buffer, pH 6.8, NaCl solution (50 μL) was combined with 0.6M HEPES buffer, pH 7.5 (100 μL, containing 5'-aminoC6 ACAA tetramer as standard) to provide a conjugate solution of 0.4 M HEPES buffer, pH 7.4. The conjugate solution was incubated in an HPLC vial at 37° C. and aliquots were injected at various intervals. Observed results demonstrated a decrease in the PEG-ssRNA conjugate peak with an increase in peaks correlating with released succinate modified NH$_2$—C6-ssRNA (i.e., COOHCH$_2$CH$_2$CO—NH—C6-ssRNA). See Table 11 and the time-concentration plot of FIG. 24.

NH$_2$—C6-ssRNA Release from SBC-PEG-30K-ssRNA Conjugate.

SBC-PEG-30K-ssRNA conjugate, prepared as described in Example 11, 17.6 μM in 20 mM Bis-Tris buffer, pH 6.8, NaCl solution (50 μL) was combined with 0.6M HEPES buffer, pH 7.5 (100 μL) to provide a conjugate solution of 0.4 M HEPES buffer, pH 7.4. The conjugate solution was incubated in an HPLC vial at 37° C. and aliquots were injected at various intervals. Observed results demonstrated a decrease in the PEG-ssRNA conjugate peak with an increase in peaks correlating with released NH$_2$—C6-ssRNA and PEG-phenol. See Table 11 and the time-concentration plot of FIG. 24.

PEG Conjugate Release Results.

Release of the PEG-ssRNA conjugates were analyzed by reverse phase HPLC at 260 nm with TEAA water/acetonitrile gradient. Decrease of the conjugate peaks were observed and plotted according to first order rate plot; ln A/A$_0$ (peak area at 260 nm) vs. time (h). The release half-life ($t_{1/2}$) for each conjugate was calculated from the slope (m=–k) of the first order rate plot where $t_{1/2}$=ln 2/k. See Table 11 and the time-concentration plot of FIG. 24.

Glycine conjugates were prepared by dissolving 10 mg PEG2-FMOC-NHS 20K reagent, as labeled, in 50 μL of 1% glycine buffer pH 9. After 15 minutes of incubation, the glycine conjugate was diluted with water (283 μL) and was combined with 0.6M HEPES buffer, pH 7.5 (667 pit) to provide a conjugate solution of 0.4 M HEPES buffer, pH 7.5. Glycine conjugates incubated at 37° C. in HPLC vials and aliquots were injected at various intervals for analysis by gel-permeation chromatography with refractive index detection. See Table 11.

TABLE 11

Release Half-life Observed for Indicated Conjugates in 0.4M HEPES, 37° C.

| | C2-PEG2-FMOC 20K | CG-PEG2-FMOC 20K | CAC-PEG2-FMOC 20K | mPEG-SBC 30K | mPEG-SS 20K |
|---|---|---|---|---|---|
| Gly Conjugate (pH 7.5) | 1.2 h | 5.1 h | 16.5 h | | |
| ssRNA Conjugate (pH 7.4) | 3.3 h | 10.7 h | 39.8 h | 3.7 h | 115.5 h |

OPSS-5K-ssRNA Release Kinetics.

Release of the PEG from the OPSS-5K-ssRNA conjugate occurs by a displacement mechanism. The substrate prepared in Example 12 above was carried out using a 50 μL, 47 μM sample in FPLC purification buffer (20 mM Bis-Tris, 200 mM NaCl, pH 6.8) using a releasing buffer: KCl: 2.7 mM, NaCl: 137 mM, phosphate: 10 mM, pH 7.4 with reduced glutathione in releasing buffer, 293 mM, was freshly made and used immediately. 50 μL RNA conjugate buffer was exchanged into releasing buffer via gel filtration; dilute RNA was added to a final volume of 0.3 mL with releasing buffer; the reduced glutathione was added into 0.3 mL RNA conjugate solution. In the final solutions; RNA conjugate concentration: 7.7 μM (estimated); reduced glutathione: 4.8 mM. The mixture was incubated at 37° C. The samples were analyzed by HPLC and the data were analyzed with Prism 4 software assuming a pseudo-first order reaction. The half-life release of the conjugate disulfide under the reduced glutathione conditions described above was 6.3 hours.

Example 19

Preparation of Chitosan 10K/FMOC-CAC 20K Conjugate

Figure 25:
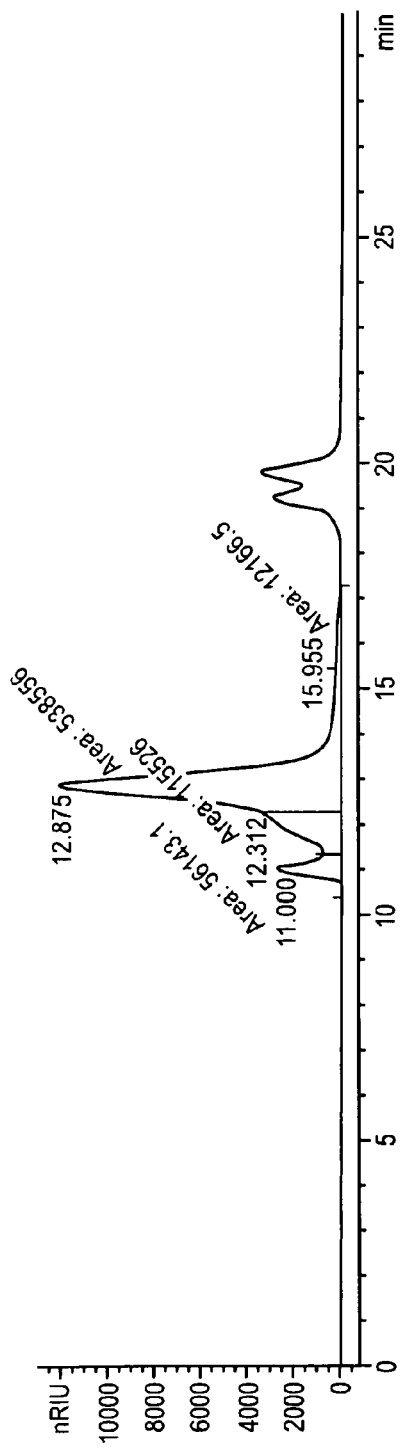
FIG. 25 is a representation of a chromatogram as further described in Example 19.

The pH of the chitosan 10K (MW=10000, 0.05 g, 0.28 mmol) solution in 5 mL of Phosphate Buffered Saline (PBS) was adjusted to pH 6.3 using 1M hydrochloric acid (HCl) or 1M sodium hydroxide (NaOH). To the solution was added 9-hydroxymethyl-4-(mPEG(10,000)-carboxyamide)-7-(3-(mPEG(10,000))carbamoyl-propyl)-N-hydroxysuccinimide polymeric reagent (FMOC-CAC 20K, 0.1 g, 5.0 μmol). The solution was stirred at room temperature. The product was purified by cation exchange chromatography using a POROS 50© cation exchange resin and a 1M sodium chloride (NaCl) solution as an eluent. The collected eluent was dialyzed to remove the excess salt using a SpectraPor MWCO 6-8000 membrane and the resulting solution was evaporated at the reduced pressure. Purified yield 42 mg. The GPC chromatogram (FIG. 25) (Ultrahydrogel 250 column, mobile phase: 0.2M sodium acetate/0.3M acetic acid, flow rate running at 0.5 mL/min, temperature 25° C., refractive index detector) shows peaks at 11.0 minutes, 12.3 minutes, 12.8 minutes, and 15.9 minutes as evidence of at least mono- and di-PEGylation of the chitosan.

Example 20

Preparation of Chitosan 10K/mPEG-SS 20K Conjugate

Figure 26:
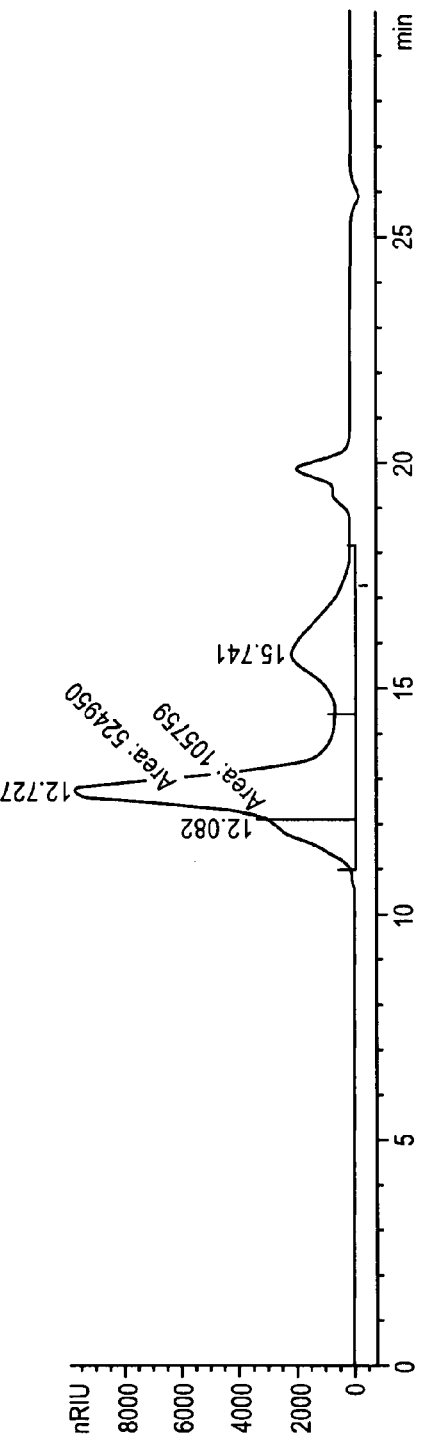
FIG. 26 is a representation of a chromatogram as further described in Example 20.

The pH of the chitosan 10K (MW=10000, 0.1 g, 0.56 mmol) solution in 5 mL of Phosphate Buffered Saline (PBS) was adjusted to pH 6.3 using 1M hydrochloric acid (HCl) or 1M sodium hydroxide (NaOH). To the solution was added mPEG-SS 20 20K polymeric reagent (double ester 20K, 0.2 g, 10.0 μmol). The solution was stirred at room temperature. The product was purified by cation exchange chromatography using a POROS 50© cation exchange resin and a 1M sodium chloride (NaCl) solution as an eluent. The collected eluent was dialyzed to remove the excess salt using a SpectraPor MWCO 6-8000 and the resulting solution was evaporated at the reduced pressure. The GPC chromatogram (FIG. 26) (Ultrahydrogel 250 column, mobile phase: 0.2M sodium acetate/0.3M acetic acid, flow rate 0.5 mL/min, temperature 25° C.; refractive index detector) shows peaks at 12.1 minutes, 12.7 minutes, and 15.7 minutes.

Example 21

Preparation of Chitosan 3-5K/IR Dye 800CW Conjugate

To a solution of the chitosan 3-5K (MW=3-5000, 0.01 g, 55.6 μmol) in 0.5 mL of DI water, 35 μL of 0.5M sodium hydroxide was added. A solution of the IR Dye 800CW NHS ester from LiCor® (MW=1166.2, 0.0025 g, 2.15 μmol) in 125 μL of DMSO (dimethyl sulfoxide) was added to the dissolved chitosan. The solution is stirred at room temperature. The product was purified by cation exchange chromatography using a 1M HCl eluent on a POROS 50© cation exchange resin. The collected acidic fraction was neutralized using 1M NaOH and was dialyzed to remove the excess salt using a SpectraPor MWCO 6-8000 membrane. Next, water was evaporated from the resulting solution at the reduced pressure.

Example 22

Preparation of Chitosan 10K/IR Dye 800CW Conjugate

To a solution of the chitosan 10K (MW=10000, 0.01 g, 55.6 μmol) in 0.5 mL of DI water, 25 μL of 0.5M sodium hydroxide was added. The IR Dye 800CW NHS ester from LiCor® (MVV=1166.2, 0.005 g, 4.3 μmol) was dissolved in 250 μL of DMSO (dimethyl sulfoxide). Next, f 60 μL of the resulting solution is removed and added to the dissolved chitosan. The solution is stirred at room temperature. The product was purified by cation exchange chromatography using a POROS 50© cation exchange resin and a 1M HCl as an eluent. The collected acidic fraction was neutralized using 1M NaOH and was dialyzed to remove the excess salt using a SpectraPor MWCO 6-8000 membrane. Next, water was evaporated from the resulting solution at the reduced pressure.

Example 23

Preparation of Chitosan 3-5K/mPEG-BTC 5K and IR Dye 800CW Conjugate

A solution of the chitosan 3-5K/mPEG-BTC 5K conjugate (MW=18-20000, 0.01 g) in 0.5 mL of DI water was prepared. The IR Dye 800CW NHS ester from LiCor® (MW=1166.2, 0.005 g, 4.3 μmol) was dissolved in 250 μL of DMSO (dimethyl sulfoxide). Next, 125 μL of the resulting solution was removed and added to the dissolved chitosan. The solution was stirred at room temperature. The product was purified by cation exchange chromatography using a POROS 50© cation exchange resin and a 1M HCl as an eluent. The collected acidic fraction was neutralized using 1M NaOH and was dialyzed to remove the excess salt using a SpectraPor MWCO 6-8000 membrane. Next, water was evaporated from the resulting solution at the reduced pressure.

Example 24

Preparation of Chitosan 10K/mPEG-BTC 5K and IR Dye 800CW Conjugate

A solution of the chitosan 10K/mPEG-BTC 5K conjugate (MW=25000, 0.01 g) in 0.5 mL of DI water was prepared. The IR Dye 800CW NHS ester from LiCor® (MW=1166.2, 0.005 g, 4.3 μmol) was dissolved in 250 μL of DMSO (dimethyl sulfoxide). Next, 60 μL of the resulting solution was removed and added to the dissolved chitosan. The solution is stirred at room temperature. The product was purified by cation exchange chromatography using a POROS 50© cation exchange resin and a 1M HCl as an eluent. The collected acidic fraction was neutralized using 1M NaOH and was dialyzed to remove the excess salt using a SpectraPor MWCO 6-8000 membrane. Next water was evaporated from the resulting solution at the reduced pressure.

Example 25

Preparation of Chitosan 3-5K/mPEG-butrALD 5K Conjugate

Figure 27:
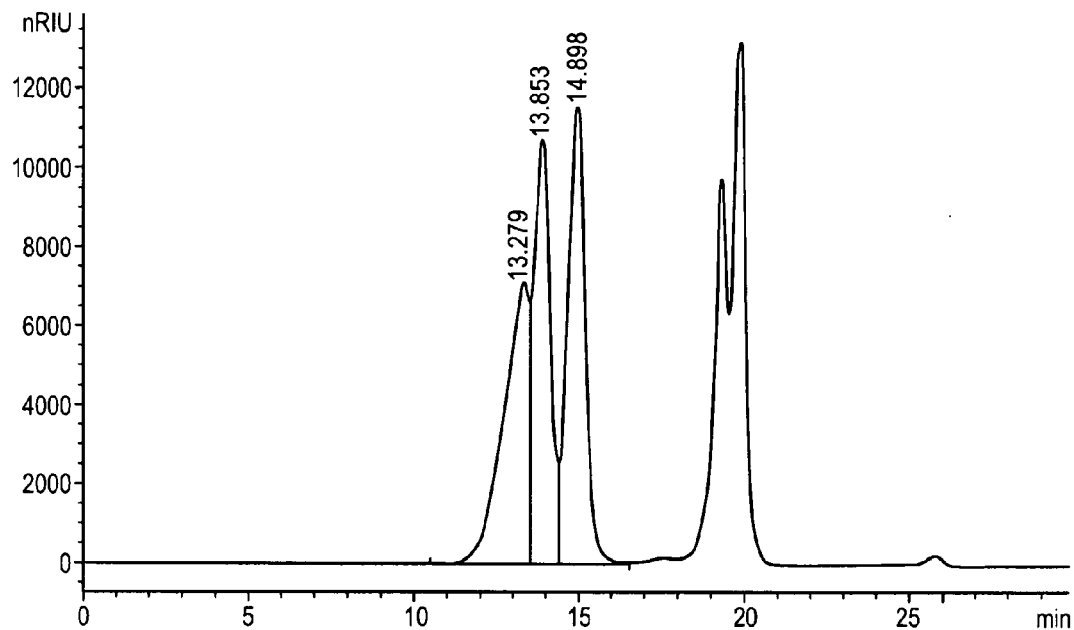
FIG. 27 is a representation of a chromatogram as further described in Example 25.

Chitosan 3-5K (MW=3-5000, 0.1 g, 0.56 mmol) was dissolved in 5 mL of DI water and the pH of the solution was adjusted to pH 8.4 using 1M sodium hydroxide (NaOH). To the solution was added mPEG-butrALD 5K (MW=5000, 1.39 g, 0.278 mmol). The solution was stirred at room temperature for one hour and then added 0.21 g sodium borohydride (5.56 mmol) was added and the mixture was stirred overnight. The reaction mixture was transferred to SpectraPor MW6-8000 dialysis tubing and dialyzed versus DI water. The dialysate is changed every hour for a total of four washes. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL and transferred to SpectraPor MWCO 6-8000 dialysis tubing and dialyzed to remove the excess salt. The conductivity of the dialysate is monitored and replaced every hour until the conductivity is approximately 4 μS/cm. The resulting solution is transferred to a round bottom flask and the solvent was evaporated at the reduced pressure. The GPC chromatogram (FIG. 27) (Ultrahydrogel 250 column, mobile phase: 0.2M sodium acetate/0.3M acetic acid, flow rate 0.5 mL/min, temperature 25° C.; refractive index detector) shows peaks at 13.2 minutes, 13.8 minutes, and 14.8 minutes.

Example 26

Preparation of Chitosan 10K/mPEG-butrALD 5K Conjugate

Figure 28:
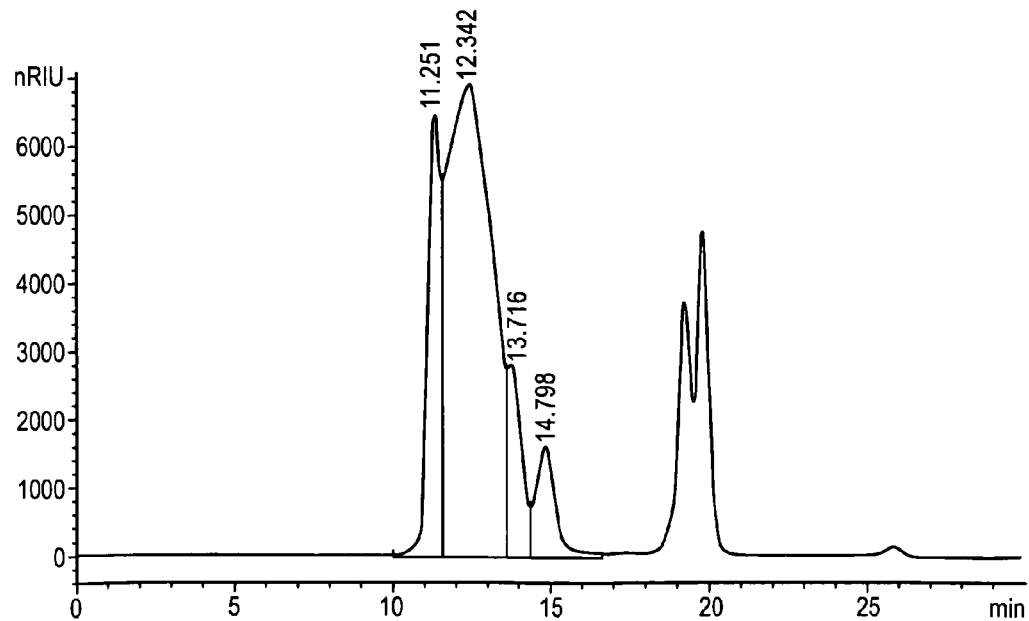
FIG. 28 is a representation of a chromatogram as further described in Example 26.

Chitosan 10K (MW=10000, 0.1 g, 0.56 mmol) was dissolved in 5 mL of DI water and the pH of the solution was adjusted to pH 6.3 using 1M sodium hydroxide (NaOH). To the solution was added mPEG-butrALD 5K (MW=5000, 1.39 g, 0.278 mmol). The solution was stirred at room temperature for one hour and then 0.21 g sodium borohydride (5.56 mmol) was added and the mixture was stirred overnight. The reaction mixture was transferred to SpectraPor MW6-8000 dialysis tubing and dialyzed versus DI water. The dialysate is changed every hour for a total of four washes. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution is transferred to a round bottom flask and water was evaporated at the reduced pressure. The GPC chromatogram (FIG. 28) (Ultrahydrogel 250 column, mobile phase: 0.2M sodium acetate/0.3M acetic acid, flow rate 0.5 mL/min, temperature 25° C.; refractive index detector) shows peaks at 11.2 minutes, 12.3 minutes, 13.7 minutes, and 14.7 minutes.

Example 27

Preparation of Chitosan 3-5K/mPEG-BTC 5K Conjugate

Chitosan 3-5K (MW=3-5000, 0.1 g, 0.56 mmol) in 10 mL of 0.1M boric acid and adjusted solution to pH 8.5 using 0.1M sodium hydroxide (NaOH). To the solution was added mPEG-BTC 5K (MW=5000, 0.77 g, 0.14 mmol). The solution was stirred at room temperature overnight. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution was transferred to a round bottom flask and water was evaporated at the reduced pressure. The GPC chromatogram (not shown) (Ultrahydrogel 250 column, mobile phase: 0.2M sodium acetate/0.3M acetic acid, flow rate 0.5 mL/min, temperature 25° C.; refractive index detector) shows peaks at 13.2 minutes, 14.4 minutes, and 17.1 minutes indicating mono-, di- and tri-PEGylation.

Example 28

Preparation of Chitosan 10K/mPEG-BTC 5K Conjugate

Chitosan 10K (MW=10000, 0.1 g, 0.56 mmol) was dissolved in 10 mL of 0.1M boric acid solution and the pH of the solution was adjusted solution to pH 6.5 using 0.1M sodium hydroxide (NaOH). To the solution was added mPEG-BTC 5K polymeric reagent (MW=5000, 0.77 g, 0.14 mmol). The solution was stirred at room temperature overnight. The product was purified by cation exchange chromatography using a POROS 50© cation exchange resin and a 1M HCl as an eluent. The collected acidic fraction was neutralized using 1M NaOH and concentrated under vacuum. The resulting material is redissolved in 10 mL DI water and transferred to SpectraPor MWCO 6-8000 dialysis tubing and dialyzed to remove the excess salt. The conductivity of the dialysate is monitored and replaced every hour until the conductivity is approximately 4 µS/cm. The resulting solution is transferred to a round bottom flask and water was evaporated at reduced pressure. The GPC chromatogram (not shown) (Ultrahydrogel 250 column, mobile phase: 0.2M sodium acetate/0.3M acetic acid, flow rate 0.5 mL/min, temperature 25° C.; refractive index detector) shows peaks at 11.4 minutes, 12.5 minutes, 13.5 minutes and 14.9 minutes indicating mono-, di- and tri-PEGylation.

Example 29

Preparation of Chitosan and Peg-Chitosan/siRNA Ionic Complexes

The chitosan or chitosan/PEG conjugate was dissolved in PBS buffer at pH 5.3, 6.3, or 7.3 with the resulting solution having a final concentration of 5 mg/mL. The siRNA duplex was dissolved in DI water at a final concentration of 2.5 mg/mL. The resulting ionic complexes were prepared by the addition of the specific quantities of the chitosan or chitosan/PEG conjugate solution (listed in the Table 12A to 12D) to the specific quantities of the solution of siRNA.

TABLE 12A

Summary of data for Chitosan 3-5K/siRNA Ionic Complexes

| Chitosan 3-5K (µL) | siRNA (µL) | PBS (µL) | Ratio (N:P) |
|---|---|---|---|
| 3 | 3 | 9 | 1:1 |
| 4.5 | 3 | 7.5 | 1.5:1 |
| 6 | 3 | 6 | 2:1 |
| 7.5 | 3 | 4.5 | 2.5:1 |

TABLE 12B

Summary of data for Chitosan 10K/siRNA Ionic Complexes

| Chitosan 10K (µL) | siRNA (µL) | PBS (µL) | Ratio (N:P) |
|---|---|---|---|
| 1.5 | 3 | 10.5 | 1:1 |
| 3 | 3 | 9 | 2:1 |
| 4.5 | 3 | 7.5 | 3:1 |
| 6 | 3 | 6 | 4:1 |
| 7.5 | 3 | 4.5 | 5:1 |

TABLE 12C

Summary of data for PEG-Chitosan 3-5K/siRNA Ionic Complexes

| PEG-Chitosan 3-5K (µL) | siRNA (µL) | PBS (µL) | Ratio (N:P) |
|---|---|---|---|
| 3 | 3 | 9 | 1:1 |
| 4.5 | 3 | 7.5 | 1.5:1 |
| 6 | 3 | 6 | 2:1 |
| 7.5 | 3 | 4.5 | 2.5:1 |

TABLE 12D

Summary of data for PEG-Chitosan 10K/siRNA Ionic Complexes

| PEG-Chitosan 10K (μL) | siRNA (μL) | PBS (μL) | Ratio (N:P) |
|---|---|---|---|
| 1.5 | 3 | 10.5 | 1:1 |
| 3 | 3 | 9 | 2:1 |
| 4.5 | 3 | 7.5 | 3:1 |
| 6 | 3 | 6 | 4:1 |
| 7.5 | 3 | 4.5 | 5:1 |

Evaluation of the prepared chitosan and chitosan-PEG complexes with siRNAs is described in the Example 35.

Example 30

PEG-Chitosan Release Kinetics

CAC-PEG2-FMOC-20K-Chitosan-10K Conjugate Release.

CAC-PEG2-FMOC-20K-Chitosan-10K conjugate, prepared as described in Example 19, 1 mg in 20 mM Bis-Tris, pH 6.8, NaCl solution (167 μL) was combined with 0.6M HEPES, pH 7.5 (333 μL) to provide a conjugate solution of 0.4 M HEPES, pH 7.4. The conjugate solution was incubated in an HPLC vial at 37° C. and aliquots were injected (reverse phase HPLC at 260 nm with TEAA water/acetonitrile gradient) at various intervals. Observed results demonstrated a decrease in the PEG-Chitosan conjugate peaks with an increase in peak correlating with released and PEG2-fulvene.

Release of the PEG-Chitosan conjugate was analyzed by reverse phase HPLC at 260 nm with TEAA water/acetonitrile gradient. Increase of the PEG-fulvene peak was observed and plotted according to first order rate plot; $\ln A/A_0$ (peak area at 260 nm) vs. time (h). The release half-life ($t_{1/2}$) for each conjugate was calculated from the slope (m=k) of the first order rate plot where $t_{1/2} = \ln 2/k$. Data provided in Table 13.

TABLE 13

Release Half-life Observed for Indicated Conjugates in 0.4M HEPES, 37° C.

| | C2-PEG2-FMOC 20K | CG-PEG2-FMOC 20K | CAC-PEG2-FMOC 20K | mPEG-SBC 30K | mPEG-SS 20K |
|---|---|---|---|---|---|
| CAC-Chitosan Conjugate, pH 7.4 | NA | NA | 2.4 h* | NA | NA |

(*Calculated from limited data, t = 0 and t = 7.2 h. NA = Data not available)

Example 31

Synthesis of an Oligomer Having an Ortho Pyridyl Disulfide (OPSS) Active Group and a RGD Peptide Targeting Moiety Following the reaction schematic shown below, the synthesis of an oligomer having an ortho pyridyl disulfide (OPSS) active group and a RGD peptide targeting moiety was conducted.

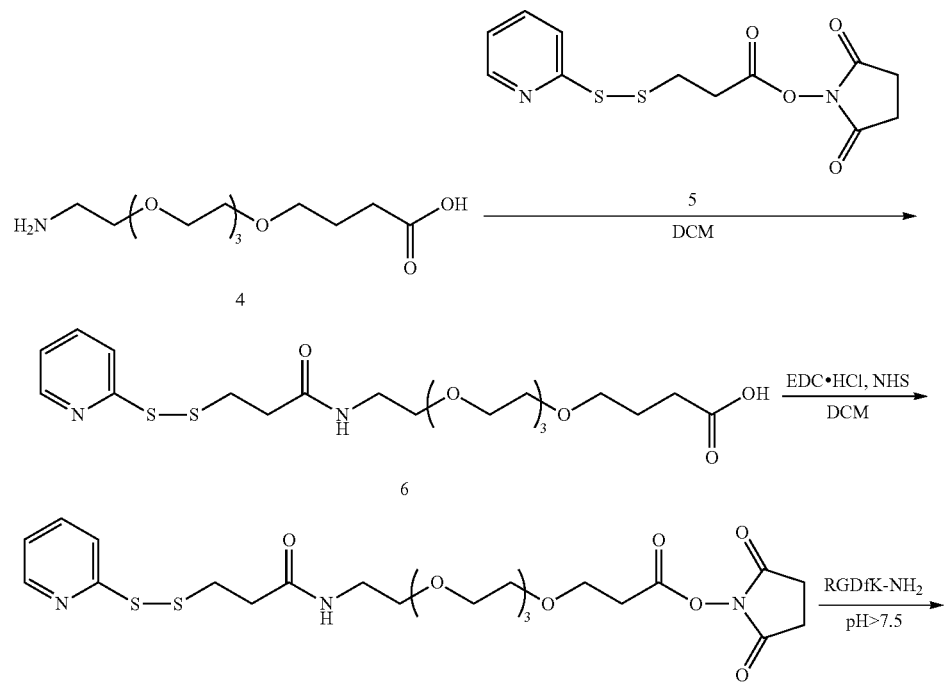

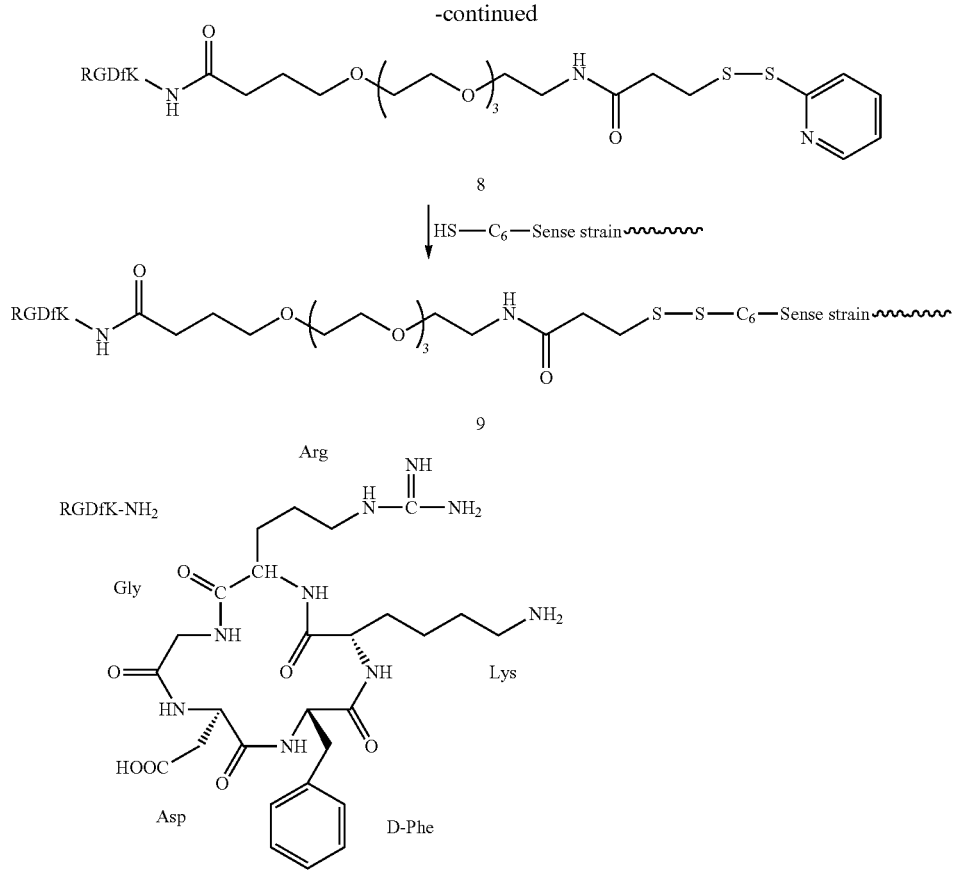

4-(2-(2-(3-(pyridin-2-yldisulfanyl)propanamido) ethoxy)ethoxy)butanoic acid (Compound 6)

4-(2-(2-aminoethoxy)ethoxy)butanoic acid (Compound 4) (F.W. 312.37, 100 mg, 0.377 mmole) in 20 mL of anhydrous toluene was azetropically distilled under reduced pressure at 60° C. on a rotary evaporator. The azeotropic distillation was repeated with 20 mL of anhydrous toluene. Then, the resulting residue was dissolved in anhydrous DCM (20 ml). To the above solution was added N-succinimidyl-3-(2-pyridithio) propionate (Compound 5) (SDPD, F.W. 265.3, 100 mg, 0.32 mmole) and triethylamine (105 µl, 0.75 mmole). The mixture was allowed to stand for overnight under stirring at room temperature. TLC showed the disappearance of SPDP. The reaction solution was washed with diluted phosphoric acid (pH4, 5 ml×2). The organic phase was dried over anhydrous $Na_2SO_4$ and concentrated under reduced pressure. The resulting residue was subject to flash chromatography on a Biotage system, giving 140 mg of Compound 6, purity>95% (HPLC). $^1$H NMR in $CDCl_3$, δ ppm: 8.49 (1H, s), 7.74 (1H, d), 7.69 (1H, m), 7.15 (1H, q), 3.80 (2H, t), 3.64 (12H, m), 3.59 (2H, t), 3.46 (2H, dd), 3.07 (2H, t), 2.64 (4H, m). ESI-MS: [M+H]$^+$ 417.

N-(2-(2-(4-(2,5-dioxopyrrolidin-1-yl)-4-oxobutoxy) ethoxy)ethyl)-3-(pyridin-2-yldisulfanyl)propanamide (Compound 7)

Compound 6 (15 mg, 0.036 mmol) was dissolved in 10 mL of anhydrous DCM. To the above solution were added NHS (4.54 mg, 1.05 equiv.) and EDC hydrochloride (7.25 mg, 1.10 equiv.), respectively. The mixture was stirred for one day at room temperature. Reverse phase HPLC analysis showed that the reaction was complete. The reaction solution was washed with diluted phosphoric acid (pH 4, 10 ml×2). Organic phase was dried over anhydrous $Na_2SO_4$ and concentrated under reduced pressure, yielding syrup Compound 7 (15 mg, 74.5%), substitution 85%. $^1$H NMR in $CDCl_3$, δ ppm: 8.49 (1H, s), 7.66 (2H, m), 7.12 (1H, m), 6.89 (1H, b), 3.86 (1H, t), 3.64 (12H, m), 3.59 (2H, t), 3.46 (2H, dd), 3.08 (2H, t), 2.89 (2H, t), 2.84 (3.4H, s), 2.62 (2H, t). ESI-MS: [M+H]$^+$ 560.

Conjugation of OPSS-TEG-SPA with cRGDfK

OPSS-TEG-SPA (5.6 mg, 0.010 mmol) [TEG representing a tetra(ethylene oxide)] was mixed with cRGDfK peptide (3.0 mg, 0.005 mmol) in 100 mM carbonate-bicarbonate buffer (pH 10.1). The mixture was allowed to stand for three hours at room temperature. The reaction mixture was analyzed on a Zorbax C18 (4.6×50 mm) with a gradient of 10-60% ACN in 0.1% TFA and flow rate 1.5 ml/min. RGDfK Conjugate with a M.W. 1047 was formed with a retention time of 1.99 min (40.6%, UV 254 nm), compared to 2.17 min for hydrolyzed form (20.1%, UV 254 nm), and 8.13 min for additional component (33%, UV 254 nm). The RDGfK with TEG linker and active OPSS group can be conjugated with siRNA having an active thiol functionality, such as the hexyl thiol modified siRNA described herein. By way of illustration, see Example 32.

Example 32 ssRNA-C$_6$-SS-TEG-(KfDGR-N Terminus) Conjugate ssRNA-C$_6$-SS-TEG-(KfDGR-N terminus) conjugate was produced by the reduction of 5' capped-RNA (5'-C6-S-SC6-AmCAmACmAGmACmUUmUAmAUmGUmAA-3', SEQ ID NO: 186) with Tris(2-Carboxyethyl) phosphine Hydrochloride (TCEP.HCl) followed by the coupling with OPSS-TEG-KfDGR-(N terminus).

To reduce 5'-capped-RNA, a 0.015-ML solution containing 0.003 mL 5'capped-RNA, 0.003-ML, 1 M, EPPS, pH 8.5 and 0.007-ML 64 mM TCEP.HCl was incubated at 25° C. without stirring for 60 minutes. After 60 minutes incubation, 0.015-ML reaction mixture was loaded on a desalting column (pre-equilibrated with 20 mM HEPES, 50 mM NaCl, pH 7.4) and rinsed with 0.045-ML buffer (20 mM HEPES, 50 mM NaCl, pH 7.4). A total of 0.06-ML solution containing RNA with free thiol group (5'-HSC6-AmCAmACmAGmAC-mUUmUAmAUmGUmAA-3' (SEQ ID NO: 195)) was collected.

To couple reduced RNA with OPSS-TEG-(KfDGR-N terminus), 0.005-mL of reduced oligo from the above reaction was mixed with 0.005-ML solution containing a mixture of OPSS-TEG-(KfDGR-N terminus) and OPSS-TEG-propionic acid. The reaction mixture was incubated at 25° C. without stirring for three hours. Analysis of the reaction mixture by ion-exchange HPLC revealed a new peak (RT=14.6 min, 26% UV 260 nm) supporting the expected formation of ssRNA-C$_6$-SS-TEG-(KfDGR-N terminus) conjugate. An additional peak was observed (RT=15.7 min, 45% UV 260 nm) and correlated with separately prepared impurity marker for ssRNA-C$_6$-SS-TEG-propionic acid conjugate. The ssRNA-C$_6$-SS-TEG-propionic acid conjugate was prepared as an impurity marker by coupling reduced RNA with OPSS-TEG-propionic acid.

Example 33

Additional Syntheses of siRNA, Chitosan, and PEGs Having Targeting Moieties

Targeting moieties may be attached to either the siRNA, chitosan (or other positively charged polymer described herein), or PEGs including heterobifunctional PEGs that may also be attached at the remote end to either chitosan or siRNA.

Pemetrexed Targeting Moiety Attached to PEG.

Using the following reaction scheme, a pemetrexed moiety (i.e., a moiety having pemetrexed activity) can be attached to a polymer.

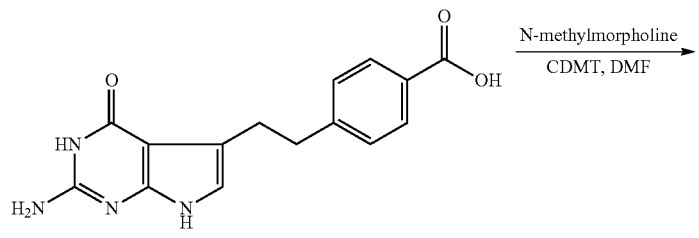

10

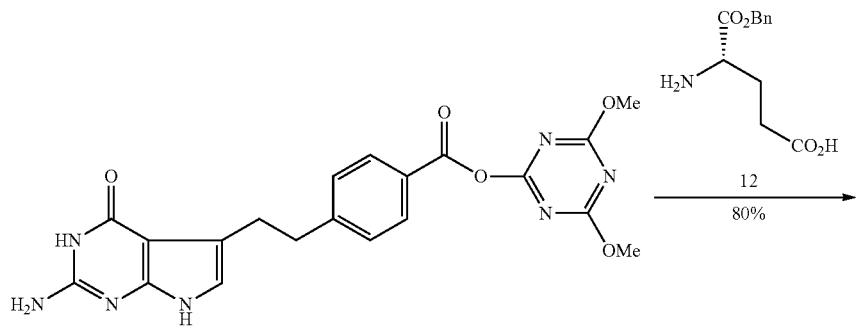

11

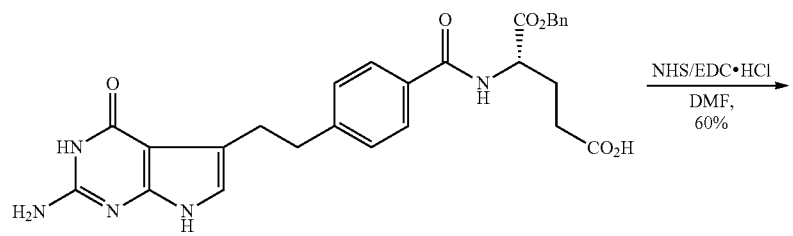

13

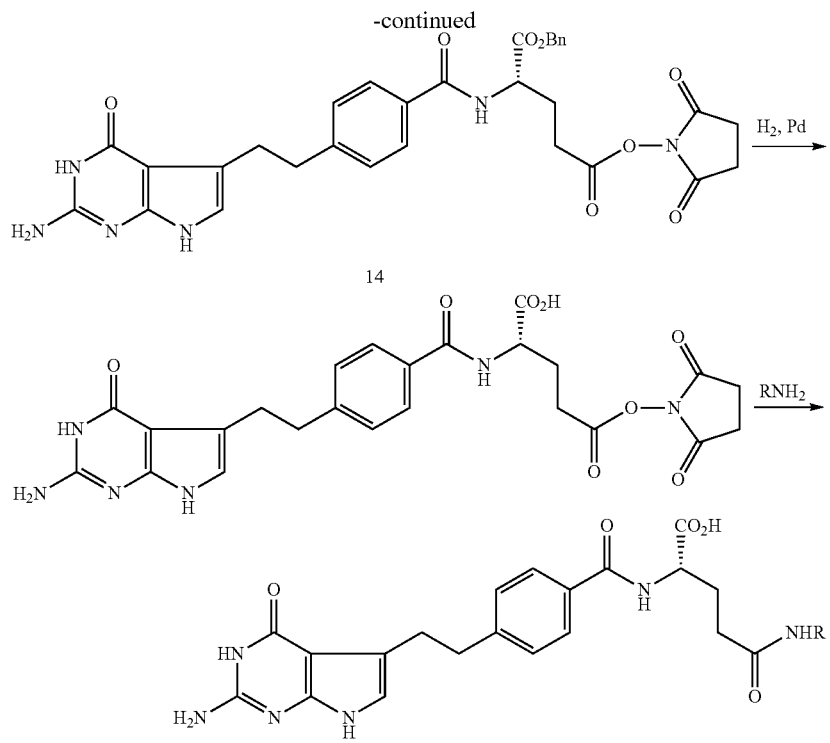

where R = chitosan, PEG, or siRNA

(S)-4-(4-(2-(2-amino-4-oxo-4,7-dihydro-3H-pyrrolo[2,3-d]pyrimidin-5-yl)ethyl)benzamido)-5-(benzyloxy)-5-oxopentanoic acid (Compound 13)

To a solution of 4-[2-(2-amino-4,7-dihydro-4-oxo-1H-pyrrolo[2,3-d]-pyrimidin-5-yl)ethyl]benzoic acid (38.4 mg, 0.129 mmol) in 5 mL of DMF was added N-methylmorpholine (40.4 mg, 0.399 mmol), followed by the addition of 2-chloro-4,6-dimethoxy-1,3,5-triazine (22.64 mg, 0.129 mmol). The resulting mixture was stirred for 1.5 hours at 25° C., at which time HPLC showed that the reaction was complete. L-glutamic acid γ-benzyl ester (30.6 mg, 0.129 mmol) was added, and stirring was continued at 25° C. until complete conversion of precursor was determined by HPLC (around two hours). To the reaction mixture was added 10 mL of methylene chloride and 10 ml of deionized water, and the mixture was stirred for 15 minutes. The layers were separated. The aqueous layer was extracted with DCM (10 ml×2). The organic phases were combined. The solution was concentrated on rotary-evaporator under reduced pressure. The resulting residue was subjected to flash chromatography on a Biotage system. Yield: 55 mg, 82%. $^1$HNMR in d$^6$-DMSO, δ ppm: 10.61 (1H, s), 10.20 (1H, s), 8.72 (1H, d, J=10 Hz), 7.78 (2H, d, J=5 Hz), 7.35 (5H, m), 7.30 (2H, m), 6.30 (1H, s), 6.07 (2H, s), 5.14 (2H, s), 3.86 (1H, m), 2.97 (2H, t), 2.84 (2H, t), 2.20 (2H, s), 2.02 (1H, m), 1.95 (1H, m). ESI-MS: 518 [M+H]$^+$.

(S)-1-benzyl 5-(2,5-dioxopyrrolidin-1-yl) 2-(4-(2-(2-amino-4-oxo-4,7-dihydro-3H-pyrrolo[2,3-d]pyrimidin-5-yl)ethyl)benzamido)pentanedioate (Compound 15)

A mixture of Compound 13 (55 mg, 0.11 mmol), NHS (15.4 mg, 0.132 mmol) and EDC hydrochloride (27 mg, 0.140 mmol) in anhydrous DMF was stirred at room temperature for two days. TLC showed the disappearance of starting material. Solvent was stripped off under reduced pressure. The resulting residue was dissolved in DCM (50 mL). The solution was washed with diluted phosphoric acid (pH 4) (50 mL×3). The organic phase was dried over anhydrous Na$_2$SO$_4$. The solvent was removed, resulting in 48 mg residue, yield 60%, substitution 80%. $^1$HNMR in d$^6$-DMSO, δ ppm: 10.65 (1H, s), 10.21 (1H, s), 8.77 (1H, d, J=10 Hz), 7.79 (2H, d, J=5 Hz), 7.34 (5H, m), 7.30 (2H, m), 6.30 (1H, s), 6.08 (2H, s), 5.16 (2H, s), 2.97 (2H, t), 2.89 (2H, t), 2.81 (3.2H, s) 2.36 (2H, m), 2.20 (2H, s). ESI-MS: 615 [M+H]$^+$.

Conjugation to chitosan amine groups, to PEG amines or to aminohexyl siRNAs is carried out in a similar manner to other reactions of amine substituted polymers described herein, e.g., see Examples 1-3. The following example demonstrates the successful attachment of the above synthesized activated targeting moiety to a heterobifunctional 20 kD Conjugation of NH$_2$-PEG-BA 20K and Pemetrexed-NHS Ester NH$_2$-PEG-butric acid 20K (0.25 g, 12.5 µmol) is added to 1 mL of 0.1M boric acid, the solution is adjusted to pH 9 using 1M NaOH. To the solution is added 0.375 mL of a 40 mg/mL pemetrexed-NHS ester (24.4 µmol) dropwise over 25 minutes while maintaining a constant pH of 9. The reaction mixture is allowed to stir at room temperature for two hours. To the solution is added 0.5 g of sodium chloride and adjusted to pH 3 using 1M HCl. The product is extracted using three aliquots of 5 mL of DCM. The collected DCM fractions are combined and the DCM is removed under vacuum. The precipitated product is analyzed by GPC Ultrahydrogel 250 column running 0.01M HEPES buffer at 0.5 mL/min at 75° C. to assess the remaining unreacted amine. A peak at 12.7 minutes corresponds to the product of pemetrexed-PEG-BA, and unreacted NH$_2$-PEG-BA has a retention time of 30.4 minutes.

There is no peak at 30.4 minutes confirming that the PEG amine had been fully substituted with the Pemetrexed moiety.

Activation of Pemetrexed-PEG-BA with NHS.

The above dried product is redissolved in 2 mL of DCM, to the solution is added 1.6 mg of NHS (N-hydroxysuccinimide, 14 μmol) and 3.3 mg of DCC (N,N'-dicyclohexylcarbodiimide, 16.2 μmol) and stirred overnight. The product is removed by precipitation through the addition of IPA (2-propanol) and collected by filtration. $^1$H-NMR (CDCl$_3$, 500 MHz): δ (ppm) 2.82 (s, 4H, CO—CH$_2$—CH$_2$—CO on NHS); 2.92 (t, CH$_2$ on β-carbon to NHS ester); 3.64 (s, PEG backbone).

Phospholipids

Following the reaction schematic below, 1,2-dipalmitoyl-glycero-3-phosphorimidazolide was prepared.

1,2-dipalmitoyl-glycero-3-phosphate monosodium salt (MW=670.87, 50 mg, 74.5 μmol) was dissolved in 5 mL chloroform, to the solution was added 76 mg imidazole (1.1 mmol), 230 mg DCC (1.1 mmol), 151 mg N-hydroxybenzotriazole (HOBt, 1.1 mmol), and 50 μL TEA. The solution was stirred at 60° C. overnight. The product was precipitated by addition of acetone and water giving a fine white precipitate. The precipitate was collected by centrifugation at 13,200 rpm for ten minutes. $^1$H-NMR (CDCl$_3$, 500 MHz): δ (ppm) 0.88 (t, 6H, —CH$_3$); 1.25 (bm, —CH$_2$—); 7.75 (d, 1H); 7.93 (d, 1H); 8.15 (d, 1H).

DSPE Targeting Moieties and Their Conjugates

Following the reaction schematic below, a DSPE targeting moiety and its conjugate can be prepared.

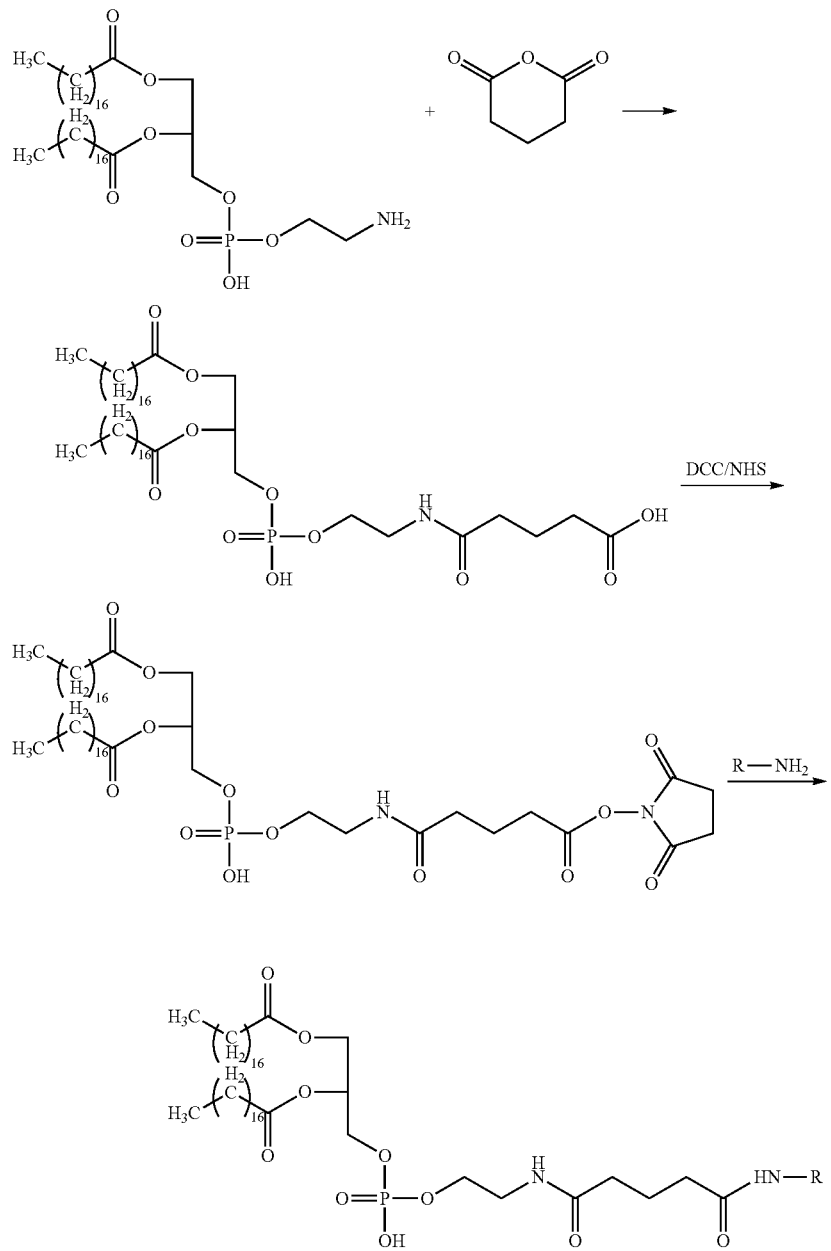

Where R-NH$_2$ is chitosan, PEG-NH$_2$ or NH$_2$-hexyl-siRNA

Preparation of 1,2-distearoyl-N-succinimidyl-glu-taryl-phosphatidylethanolamine (DSPE-NHS)

To the solution of 5 mL of chloroform was added 100 mg of 1,2-distearoyl-sn-glyvero-3-phosphoethanolamine (DSPE, 0.133 mmol), 36 mg of 4-dimethylamino pyridine (DMAP, 0.294 mmol), 17 mg of glutaric anhydride (0.147 mmol), and 28 μL of triethylamine (TEA). The reaction mixture was stirred at 60° C. for 4 hours. DSPE was precipitated by the addition of 20 mL of acetone and the product was collected by filtration.

The dried product was redissolved in 1 mL of chloroform and to the solution was added 38 mg of DCC and 18 mg of NHS. The reaction was stirred at room temperature overnight. To the solution was added 10 mL of acetone and then filtered to remove any insoluble material. The acetone/chloroform mixture was removed under vacuum. $^{1}$H-NMR (CDCl$_3$, 500 MHz): δ (ppm) 0.88 (t, 6H, —CH$_3$); 1.25 (s, —CH$_2$—); 2.07 (m, 2H, —CH$_2$— γ-carbon on glutaric anhydride); 2.82 (s, 4H, CO—CH$_2$—CH$_2$—CO on NHS); 2.92 (t, CH$_2$ on β-carbon to NHS ester).

Conjugation to chitosan amine groups, to PEG amines or to aminohexyl siRNAs is carried out in a similar manner to other reactions of amine substituted polymers described herein, e.g., see Examples 1-3.

Example 34

Biological Evaluation of Conjugates

Methods.
The siRNA sequence is directed against Sjogren syndrome antigen B (SSB) gene.

```
Sense:
                                          (SEQ ID NO: 191)
5'-AmCAmACmAGmACmUUmUAmAUmGUmAA-3'.

Antisense:
                                          (SEQ ID NO: 192)
3'-mUGmUUmGUmCUmGAmAAmUUmACmAUmU-5'.
(Lower case 'm' indicates "2'OMe" modification).
```

Figure 29:
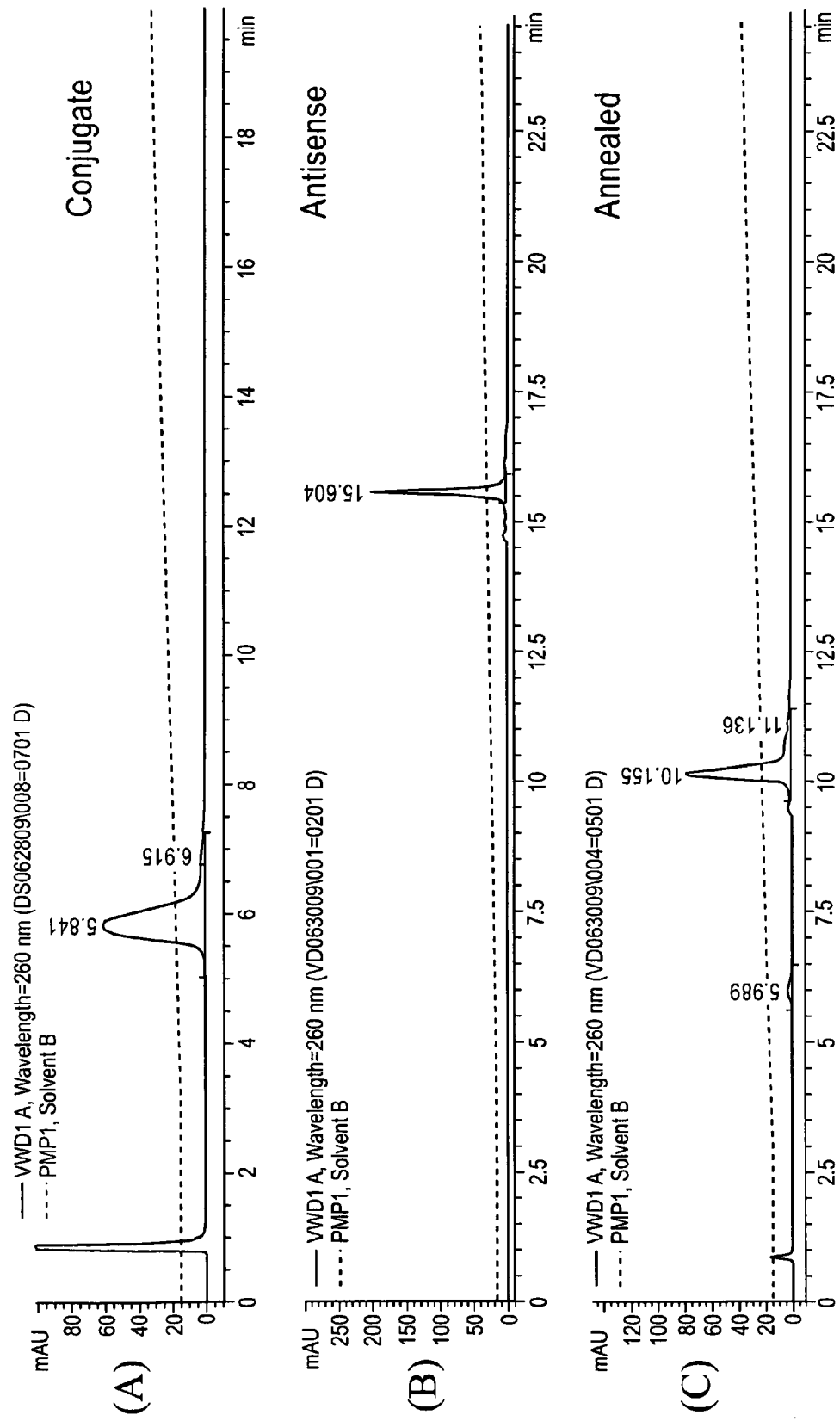
FIG. 29 shows three panels, A, B and C corresponding to conjugate, antisense and annealed, as further described in Example 34.

Annealing Conjugates.
The antisense strand was re-suspended in siRNA buffer (Thermo Scientific, USA). RNA concentration of the sense-strand-polymer conjugates was determined using RiboGreen (Invitrogen, USA) as per manufacturer's instructions. RNA sense strand-conjugates were mixed with antisense at eqimolar concentrations and heated to 50° C. for five minutes followed by gradual cooling to room temperature. Displayed in FIG. 29 are results of ion exchange chromatography of conjugate CAC-FMOC 20K; 5'NH-sense (panel A), antisense (panel B), conjugate annealed with antisense (panel C).

Cell Line and Transfection.
Human embryonic kidney 293 cells were plated on 12-well plates (1.5×10$^5$ cells per well) in MEMa supplemented with 10% FBS. The following day, medium was changed to reduced serum OPTI-MEM (Gibco, Carlsbad, Calif., USA). Cells were treated with 100 nM annealed conjugate complexed with Lipofectamine 2000 as per manufacturer's instruction. Four hours after treatment, FBS was added to each well to a final concentration of 2%. Cells were harvested 48 hours after conjugate treatment and RNA isolated using Tri-Reagent (Applied Biosystems, CA, USA) as per manufacturer's instructions.

RT-qPCR.
RNA yield was determined spectrophotometrically by measuring absorbance at 260 nm and RNA quality was assessed by agarose gel electrophoresis. Equal amounts of RNA (600 μgs) was converted to cDNA using High-Capacity cDNA Reverse transcription Kit (Applied Biosystems, USA) as per manufacturer's instructions. Levels of SSB mRNA in each sample were determined using an ABI7300 Q-PCR instrument and TaqMan assay reagents from Applied Biosystems (SSB assay cat. #4331182, Hs00427601 ml and GAPDH assay cat. #4326317E).

Figure 30:
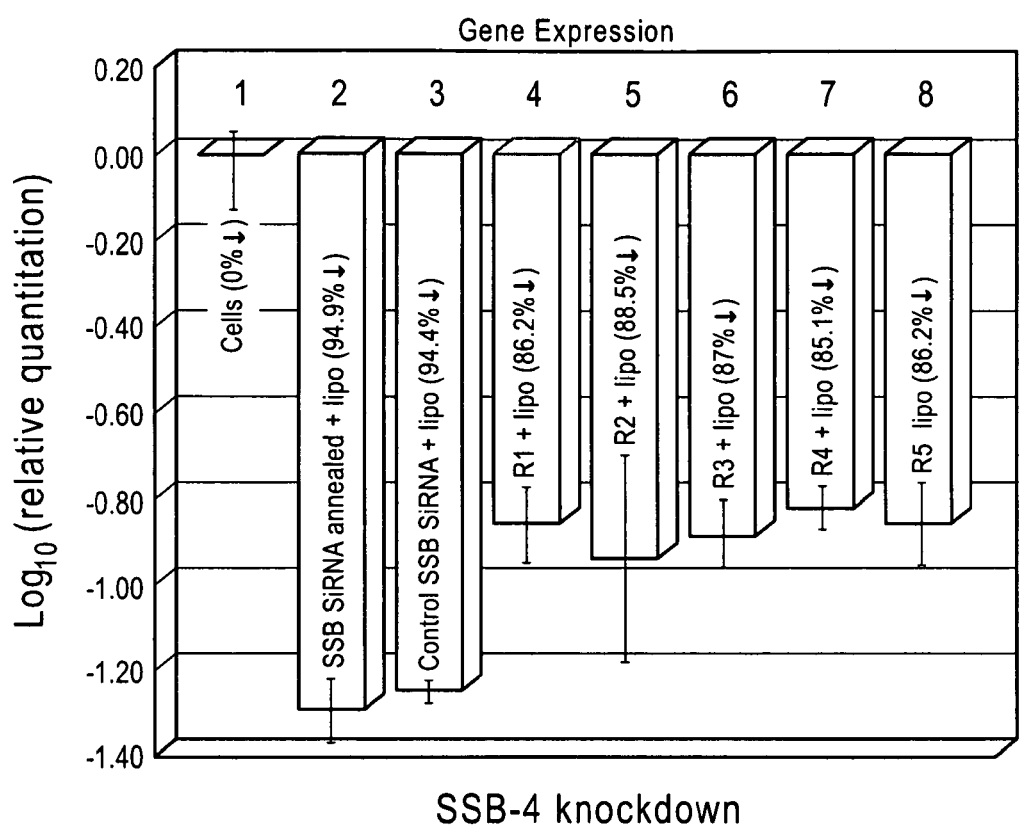
FIG. 30 is a graph as further described in Example 34 and shows the knockdown of SSB RNA expression by conjugates R1 through R5 when transfected using Lipofectamine 2000. SSB gene expression relative to untreated cells (bar1), annealed siRNA (bar2), control SSB siRNA (bar3), conjugates R1 through R5 complexed with Lipofectamine2000 (bars 4 through 8).
Figure 31:
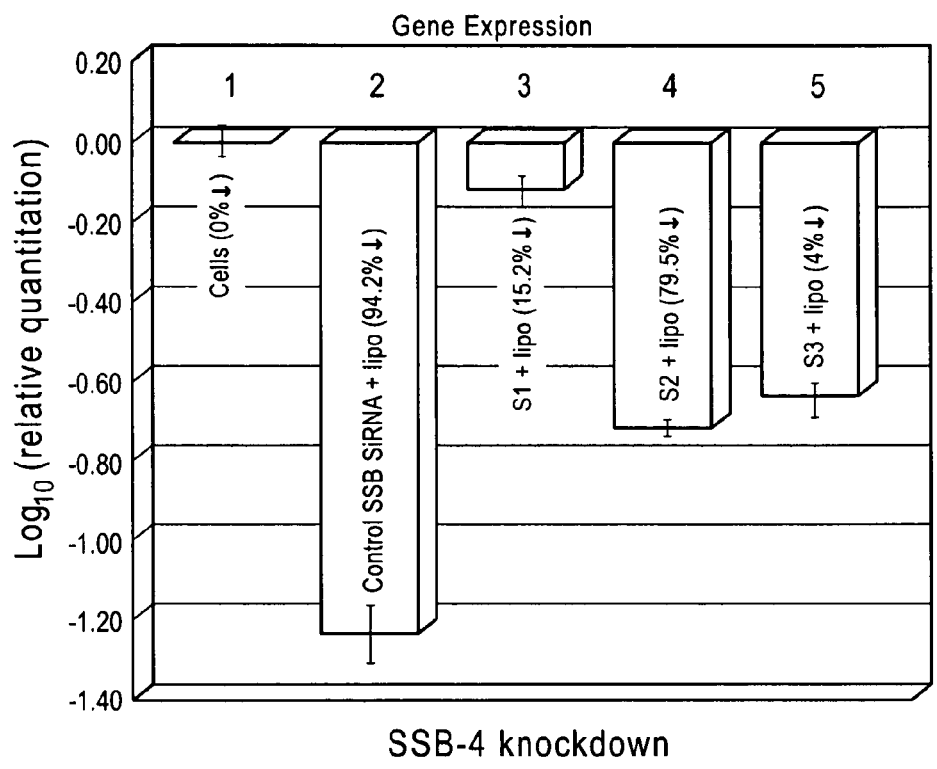
FIG. 31 is a graph as further described in Example 34 and shows the SSB gene expression relative to untreated cells (bar1), control SSB siRNA (bar2), conjugates S1 through S3 complexed with Lipofectamine2000 (bars 3 through 5).
Figure 32:
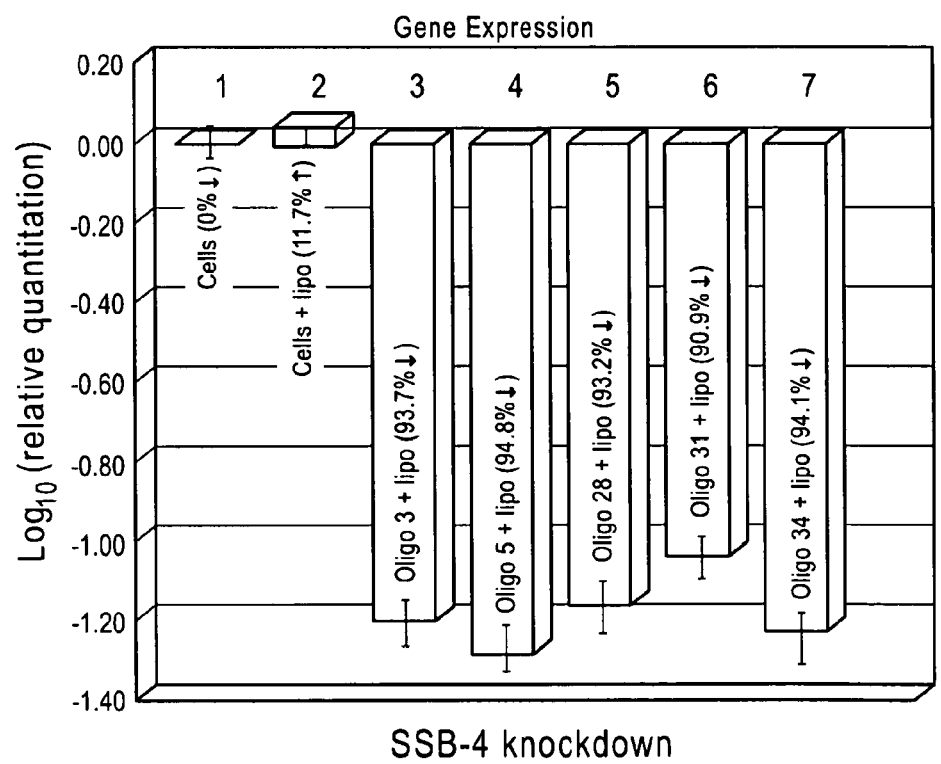
FIG. 32 is a graph as further described in Example 34 and shows the SSB gene expression relative to untreated cells (bar1), cells treated with lipofectamine2000 (bar2)

FIG. 30 shows knockdown of SSB RNA expression by conjugates R1 through R5 when transfected using Lipofectamine2000. SSB gene expression relative to untreated cells (bar1), annealed siRNA (bar2), control SSB siRNA (bar3), conjugates R1 through R5 complexed with Lipofectamine2000 (bars 4 through 8). FIG. 31 shows knockdown of SSB RNA expression in cells treated with conjugates S1 through S3 transfected using Lipofectamine2000. FIG. 32 shows SSB RNA expression knockdown by SSB siRNA with various linkers attached prior to polymer conjugation. All constructs shown were annealed prior to use with the same sense or antisense strand sequence.

Example 35

Evaluation of Chitosan-PEG Complexes with siRNAs

PAGE Gel electrophoresis of siRNA/chitosan ionic complexes. The siRNA and chitosan or chitosan/PEG conjugates are mixed together at a given ratio of N:P with a volume of 15 μL, added to this solution is 3 μL of a loading material containing 50% glycerol. Each sample (10 μL) is loaded into a 15% PAGE gel running a TAE buffer (Tris Acetate EDTA) at pH 7.3. The gel is run at 100 volts for two hours, afterwards the gel is removed from the cassette and stained for 10 minutes using 10 mg/mL ethidium bromide solution and washed for a minimum of one hour in DI water. The ethidium bromide stained gel is visualized by UV light.

Complexes of various chitosan/siRNA modifications were evaluated using analysis using PAGE gel. PAGE gel analysis was completed using a 1:1 and a 2:1 ratio (N:P) of a chitosan 3-5 kD/mPEG-butrALD 5 kD and chitosan 10 kD/mPEG-butrALD 5 kD using a running buffer of TBE (pH 8.4), TAE (pH 7.3) and TAE (pH 5.3). No neutralization of the siRNA duplex (SEQ ID NO: 183:SEQ ID NO: 192) was seen with the chitosan 3-5K and some slight tailing seen with the chitosan 10K complexes indicating some neutralization of the siRNA duplex.

The gel showing the analysis of chitosan-PEG complexes with siRNA is provided in FIG. 33, wherein lane 1 corresponds to the siRNA duplex, lane 2 corresponds to chitosan 3-5K/ALD 5K and siRNA at 1:1, lane 3 corresponds to chitosan 10K/ALD 5K and siRNA at 1:1, lane 4 corresponds to chitosan 10K/ALD 5K and siRNA at 2:1, lane 5 corresponds to IR 800CW dye labeled chitosan 10K/BTC 5K and siRNA at 1:1, lane 6 corresponds to IR 800CW dye labeled chitosan 10K/BTC 5K and siRNA at 2:1, lane 7 corresponds to siRNA duplex, lane 8 corresponds to chitosan 3-5K/ALD 5K and siRNA at 1:1, lane 9 corresponds to chitosan 10K/ALD 5K and siRNA at 1:1, and lane 10 corresponds to chitosan 10K/ALD 5K and siRNA at 2:1.

Increasing the nitrogen ratio leads to neutralization of the siRNA duplex. Analysis based on a PAGE gel using TAE buffer at pH 7.3 was performed. The chitosan 10 kD/mPEG-butrALD 5 kD neutralizes the siRNA duplex, as revealed by the PAGE gels. The gel showing the analysis of chitosan-PEG complexes with siRNA, wherein the complexes were formed with increased nitrogen ratios is provided in FIG. 34. In this gel, lane 1 corresponds to siRNA duplex, lane 2 corresponds to chitosan 3-5K/ALD 5K and siRNA at 50:1, lane 3 corresponds to chitosan 3-5K/ALD 5K and siRNA at 20:1, lane 4 corresponds to chitosan 3-5K/ALD 5K and siRNA at 10:1, lane 5 corresponds to chitosan 10K/ALD 5K and siRNA at 50:1, lane 6 corresponds to chitosan 10K/ALD 5K and siRNA at 20:1, lane 7 corresponds to chitosan 10K/ALD 5K and siRNA at 10:1, lane 8 corresponds to siRNA duplex, lane 9 corresponds to IR 800CW dye labeled chitosan 10K/BTC 5K and siRNA at 10:1, and lane 10 corresponds to siRNA duplex.

What is claimed is:

1. A complex comprising a chitosan complexed with a siNA, wherein; (i) the chitosan is attached through an amide-containing linkage to a water-soluble polymer, wherein the water-soluble polymer is a polyethylene oxide having a weight-average molecule weight in the range of from about 10,000 Daltons to about 85,000 Daltons and end-capped with a $C_{1-6}$ alkoxy group; and (ii) the chitosan has a molecular weight of between 1,000 Daltons and 2,000,000 Daltons.

2. The complex of claim 1, wherein the chitosan has a molecular weight of between 1,000 Daltons and 25,000 Daltons.

3. The complex of claim 1, wherein the chitosan has a degree of deacetylation (% DA) of 50 to 100%.

4. The complex of claim 1, wherein more than one water-soluble polymer is attached to the chitosan.

5. The complex of claim 1, wherein the siNA is selected from the group consisting of siRNA, miRNA and shRNA.

6. The complex of claim 5, wherein the siNA is a siRNA.

7. The complex of claim 1, wherein the siNA has a length of from 10 to 30 nucleotides.

8. The complex of claim 1, wherein the siNA has a length of from 15 to 25 nucleotides.

9. The complex of claim 1, wherein the siNA is a single stranded siNA.

10. The complex of claim 1, wherein the siNA is a double stranded siNA.

11. The complex of claim 10, wherein the double stranded siNA is blunt ended.

12. The complex of claim 10, wherein the double stranded siNA has a 5' overhang.

13. The complex of claim 12, wherein the 5' overhang is an overhang of a number of nucleotides selected from the group consisting of 1, 2, 3 and 4.

14. The complex of claim 10, wherein the double stranded siNA has a 3' overhang.

15. The complex of claim 14, wherein the 3' overhang is an overhang of a number of nucleotides selected from the group consisting of 1, 2, 3 and 4.

16. The complex of claim 1, wherein the siNA is a triple stranded siNA.

17. The complex of claim 1, wherein the siNA includes one or more modified nucleotides selected from the group consisting of 2' O-methyl nucleotides, 2' F nucleotides, 2'-deoxy-nucleotides, 2'-O-methoxyethyl (2'-O-MOE) nucleotides, locked nucleic acids and unlocked nucleic acids.

18. The complex of claim 1, further comprising a targeting moiety attached to one component of the complex.

19. The complex of claim 18, wherein the targeting moiety is selected from the group consisting of folate, pemetrexed, RGD peptide, and cholesterol.

20. A composition comprising the complex of claim 1.

21. The composition of claim 20, further comprising a transfection agent.

22. A method comprising subcutaneously administering to a patient the complex of claim 1.

* * * * *

SEQUENCE LISTING

```
<160> NUMBER OF SEQ ID NOS: 195

<210> SEQ ID NO 1
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 1
cuccuuuugu uucugcuaac gtt                                            23

<210> SEQ ID NO 2
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 2
cguuagcaga aacaaaagga gtt                                            23

<210> SEQ ID NO 3
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 3
cuccuuuugu uucugcuaac gtt                                            23

<210> SEQ ID NO 4
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 4
```

-continued cguuagcaga aacaaaagga gtt                                           23

<210> SEQ ID NO 5
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 5
cuccuuuugu uucugcuaac gtt                                           23

<210> SEQ ID NO 6
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 6
cguuagcaga aacaaaagga gtt                                           23

<210> SEQ ID NO 7
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 7
cucauuuucu uugugcucac gtt                                           23

<210> SEQ ID NO 8
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 8
cgugagcaca aagaaaauga gtt                                           23

<210> SEQ ID NO 9
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

```
<400> SEQUENCE: 9
cuccuuuugu uucugcuaac gtt                                              23

<210> SEQ ID NO 10
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 10
cguuagcaga aacaaaagga gtt                                              23

<210> SEQ ID NO 11
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 11
cucauuuucu uugugcucac gtt                                              23

<210> SEQ ID NO 12
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 12
cgugagcaca aagaaaauga gtt                                              23

<210> SEQ ID NO 13
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 13
cuccuuuugu uucugcuaac g                                                21

<210> SEQ ID NO 14
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 14
```
cguuagcaga aacaaaagga g                                              21

<210> SEQ ID NO 15
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 15
cucauuuucu uugugcucac g                                              21

<210> SEQ ID NO 16
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 16
cgugagcaca agaaaauga g                                               21

<210> SEQ ID NO 17
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 17
ttcuccuuuu guuucugcua acg                                            23

<210> SEQ ID NO 18
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 18
ttcguuagca gaaacaaaag gag                                            23

<210> SEQ ID NO 19
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 19
ttcucauuuu cuugugcuc acg                                             23

<210> SEQ ID NO 20
<211> LENGTH: 23

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 20
ttcgugagca caaagaaaau gag                                           23

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
ucuugaugua cuccccucgu u                                             21

<210> SEQ ID NO 22
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 22 cgagggagu acaucaagau u                                              21

<210> SEQ ID NO 23
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 23
ucuugaugua cuccccucgu u                                             21

<210> SEQ ID NO 24
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 24 cgagggagu acaucaagac c                                              21

<210> SEQ ID NO 25
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 25
cuugauguac uccccucgu                                                19
```

```
<210> SEQ ID NO 26
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 26
gaggggagua caucaagac                                                   19

<210> SEQ ID NO 27
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 27
ucuugaugua cuccccucgt t                                                21

<210> SEQ ID NO 28
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 28
cgaggggagu acaucaagac c                                                21

<210> SEQ ID NO 29
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 29
ucuugaugua cuccccucgu u                                                21

<210> SEQ ID NO 30
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 30
cgaggggagu acaucaagau u                                                21

<210> SEQ ID NO 31
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
```

```
<223> OTHER INFORMATION: Description of Artificial Sequence: Synthetic
      oligonucleotide

<400> SEQUENCE: 31
ucuugaugua cuccccucgt t                                              21

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
cgaggggagu acaucaagat t                                              21

<210> SEQ ID NO 33
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
acuugaugua cuccccucct t                                              21

<210> SEQ ID NO 34
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 34
ggaggggagu acaucaagut t                                              21

<210> SEQ ID NO 35
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 35
aguugaugua cuccccugct t                                              21

<210> SEQ ID NO 36
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 36
gcaggggagu acaucaacut t                                              21

<210> SEQ ID NO 37
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 37
ucuugaugua cuccccucgu u                                              21

<210> SEQ ID NO 38
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 38
cgaggggagu acaucaagau u                                              21

<210> SEQ ID NO 39
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 39
ucuugaugua cuccccucgu u                                              21

<210> SEQ ID NO 40
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 40
cgaggggagu acaucaagac c                                              21

<210> SEQ ID NO 41
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 41
ucuugaugua cuccccucgt t                                              21

<210> SEQ ID NO 42
<211> LENGTH: 21
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 42 cgagggagu acaucaagac c                                              21

<210> SEQ ID NO 43
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 43
ucuugaugua cuccccucgt t                                             21

<210> SEQ ID NO 44
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 44 cgagggagu acaucaagat t                                              21

<210> SEQ ID NO 45
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 45
cuugauguac uccccucgu                                                19

<210> SEQ ID NO 46
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 46
gaggggagua caucaagac                                                19

<210> SEQ ID NO 47
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
```

```
<220> FEATURE:
<223> OTHER INFORMATION: Description of Artificial Sequence: Synthetic
      oligonucleotide

<400> SEQUENCE: 47
acuugaugua cuccccucct t                                              21

<210> SEQ ID NO 48
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 48 ggagggagu acaucaagut t                                               21

<210> SEQ ID NO 49
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 49
aguugaugua cuccccugct t                                              21

<210> SEQ ID NO 50
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 50 gcagggagu acaucaacut t                                               21

<210> SEQ ID NO 51
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 51
cuccuuuugu uucugcuaac gtt                                            23

<210> SEQ ID NO 52
<211> LENGTH: 23
<212> TYPE: DNA
<213> ORGANISM: Artificial Sequence
<220> FEATURE:
<223> OTHER INFORMATION: Description of Combined DNA/RNA Molecule:
```

Synthetic oligonucleotide
<220> FEATURE:
<223> OTHER INFORMATION: Description of Artificial Sequence: Synthetic
      oligonucleotide

<400> SEQUENCE: 52
cguuagcaga aacaaaagga gtt                                              23

<210> SEQ ID NO 53
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 53
uccuuuuguu ucugcuaac                                                   19

<210> SEQ ID NO 54
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 54
guuagcagaa acaaaagga                                                   19

<210> SEQ ID NO 55
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 55
uccuuuucuu ucugcuaac                                                   19

<210> SEQ ID NO 56
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 56
guuagcagaa agaaaagga                                                   19

<210> SEQ ID NO 57
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 57
uccuuuucuu ugugcuaac                                                   19

<210> SEQ ID NO 58
<211> LENGTH: 19
<212> TYPE: RNA
<213> ORGANISM: Artificial Sequence

```
<220> FEATURE:
<223> OTHER INFORMATION: Description of Artificial Sequence: Synthetic
      oligonucleotide

<400> SEQUENCE: 58
guuagcacaa agaaaagga                                                      19

<210> SEQ ID NO 59
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 59
uccuuuucuu ugugguaac                                                      19

<210> SEQ ID NO 60
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 60
guuaccacaa agaaaagga                                                      19

<210> SEQ ID NO 61
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 61
uccuauucuu ugugguaac                                                      19

<210> SEQ ID NO 62
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 62
guuaccacaa agaauagga                                                      19

<210> SEQ ID NO 63
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 63
cuccuuuugu uucugcuaac gtt                                                 23

<210> SEQ ID NO 64
<211> LENGTH: 23
```

```
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 64
cguuagcaga aacaaaagga gtt                                              23

<210> SEQ ID NO 65
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 65
cuccuuuugu uucugcuaac gtt                                              23

<210> SEQ ID NO 66
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 66
cguuagcaga aacaaaagga gtt                                              23

<210> SEQ ID NO 67
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 67
```

-continued cuccuuuugu uucugcuaac gtt          23

<210> SEQ ID NO 68
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 68
cguuagcaga aacaaaagga gtt          23

<210> SEQ ID NO 69
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 69
ttcguuagca gaaacaaaag gag          23

<210> SEQ ID NO 70
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 70
cuccuuuugu uucugcuaac gtt          23

<210> SEQ ID NO 71
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 71
cguuagcaga aacaaaagga gtt          23

```
<210> SEQ ID NO 72
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 72
cuccuuuugu uucugcuaac gtt                                              23

<210> SEQ ID NO 73
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 73
cuccuuuugu uucugcuaac gtt                                              23

<210> SEQ ID NO 74
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 74
cuccuuuugu uucugcuaac gtt                                              23

<210> SEQ ID NO 75
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (23)..(23)
<223> OTHER INFORMATION: NH2-modified

<400> SEQUENCE: 75
cuccuuuugu uucugcuaac gtt                                              23

<210> SEQ ID NO 76
<211> LENGTH: 23
<212> TYPE: DNA
```

```
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 76
ttcuccuuuu guuucugcua acg                                            23

<210> SEQ ID NO 77
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: NH2-modified
<220> FEATURE:
<221> NAME/KEY: misc_feature
<222> LOCATION: (23)..(23)
<223> OTHER INFORMATION: NH2-modified

<400> SEQUENCE: 77
cguuagcaga aacaaaagga gtt                                            23

<210> SEQ ID NO 78
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 78
cuccuuuugu uucugcuaac gtt                                            23

<210> SEQ ID NO 79
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 79
cguuagcaga aacaaaagga gtt                                            23

<210> SEQ ID NO 80
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 80
```
cuccuuuugu uucugcuaac g    21

<210> SEQ ID NO 81
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 81
cuccuuuucu uugugcuaac g    21

<210> SEQ ID NO 82
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 82
cguuagcaca aacaaaagga g    21

<210> SEQ ID NO 83
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 83
cuccuuuugu uucugcuaac g    21

<210> SEQ ID NO 84
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 84
cguuagcaga aacaaaagga g    21

<210> SEQ ID NO 85
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 85
cuccuuuugu uucugcuaac g    21

```
<210> SEQ ID NO 86
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 86
cguuagcaga aacaaaagga g                                              21

<210> SEQ ID NO 87
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 87
cuccuuuugu uucugcuaac g                                              21

<210> SEQ ID NO 88
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 88
cguuagcaga aacaaaagga g                                              21

<210> SEQ ID NO 89
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 89
cuccuuuugu uucugcuaac g                                              21

<210> SEQ ID NO 90
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
```

<223> OTHER INFORMATION: 2'-O-methyl modified

<400> SEQUENCE: 90
cguuagcaga aacaaaagga g                                              21

<210> SEQ ID NO 91
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 91
cuccuuuugu uucugcuaac g                                              21

<210> SEQ ID NO 92
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 92
cguuagcaga aacaaaagga g                                              21

<210> SEQ ID NO 93
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 93
cuccuuuugu uucugcuaac g                                              21

<210> SEQ ID NO 94
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 94
cguuagcaga aacaaaagga g                                              21

<210> SEQ ID NO 95
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

```
<400> SEQUENCE: 95
cuccuuuugu uucugcuaac g                                              21

<210> SEQ ID NO 96
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 96
cguuagcaga aacaaaagga g                                              21

<210> SEQ ID NO 97
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(13)
<223> OTHER INFORMATION: 2'-O-methyl modified

<400> SEQUENCE: 97
cuccuuuugu uucugcuaac g                                              21

<210> SEQ ID NO 98
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: 2'-O-methyl modified
<220> FEATURE:
<221> NAME/KEY: modified_base
<222> LOCATION: (16)..(21)
<223> OTHER INFORMATION: 2'-O-methyl modified

<400> SEQUENCE: 98
cuccuuuugu uucugcuaac g                                              21

<210> SEQ ID NO 99
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: 2'-O-methyl modified
<220> FEATURE:
<221> NAME/KEY: modified_base
<222> LOCATION: (17)..(21)
<223> OTHER INFORMATION: 2'-O-methyl modified

<400> SEQUENCE: 99
cguuagcaga aacaaaagga g                                              21
```

<210> SEQ ID NO 100
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 100
cuccuuuugu uucugcuaac g                                              21

<210> SEQ ID NO 101
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 101
cuccuuuugu uucugcuaac g                                              21

<210> SEQ ID NO 102
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 102
cguuagcaga aacaaaagga g                                              21

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 103
cuccuuuugu uucugcuaac g                                              21

<210> SEQ ID NO 104
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 104
cguuagcaga aacaaaagga g                                              21

```
<210> SEQ ID NO 105
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 105
cuccuuuugu uucugcuaac g                                              21

<210> SEQ ID NO 106
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 106
cguuagcaga aacaaaagga g                                              21

<210> SEQ ID NO 107
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 107
cuccuuuugu uucugcuaac g                                              21

<210> SEQ ID NO 108
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 108
cguuagcaga aacaaaagga g                                              21

<210> SEQ ID NO 109
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(10)
<223> OTHER INFORMATION: 2'-O-methyl modified
```

```
<220> FEATURE:
<221> NAME/KEY: modified_base
<222> LOCATION: (16)..(21)
<223> OTHER INFORMATION: 2'-O-methyl modified

<400> SEQUENCE: 109
cuccuuuugu uucugcuaac g                                              21

<210> SEQ ID NO 110
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(11)
<223> OTHER INFORMATION: 2'-O-methyl modified
<220> FEATURE:
<221> NAME/KEY: modified_base
<222> LOCATION: (18)..(21)
<223> OTHER INFORMATION: 2'-O-methyl modified

<400> SEQUENCE: 110
cguuagcaga aacaaaagga g                                              21

<210> SEQ ID NO 111
<211> LENGTH: 21
<212> TYPE: RNA
<213> ORGANISM: Artificial Sequence
<220> FEATURE:
<221> NAME/KEY: source
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified
```

-continued

```
<400> SEQUENCE: 111
cuccuuuugu uucugcuaac g                                          21

<210> SEQ ID NO 112
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 112
cguuagcaga aacaaaagga g                                          21

<210> SEQ ID NO 113
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
```

```
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 113
cuccuuuugu uucugcuaac g                                          21

<210> SEQ ID NO 114
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
```

```
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 114
cguuagcaga aacaaaagga g                                              21

<210> SEQ ID NO 115
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 115
cuccuuuugu uucugcuaac g                                              21

<210> SEQ ID NO 116
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
```

```
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 116
cguuagcaga aacaaaagga g                                              21

<210> SEQ ID NO 117
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
```

```
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 117
cuccuuuugu uucugcuaac g                                            21

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 118
cguuagcaga aacaaaagga g                                            21

<210> SEQ ID NO 119
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
cuccuuuugu uucugcuaac g                                             21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
cguuagcaga aacaaaagga g                                             21

<210> SEQ ID NO 121
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 121
cucauuuucu uugugcucac g                                             21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
cgugagcaca aagaaaauga g                                             21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 123
cuccuuuugu uucugcuaac g                                             21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified
```

-continued

```
<400> SEQUENCE: 124
cguuagcaga aacaaaagga g                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 125
cuccuuuugu uucugcuaac g                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (3)..(19)
<223> OTHER INFORMATION: 2'-O-methyl modified

<400> SEQUENCE: 126
cguuagcaga aacaaaagga g                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 127
cuccuuuugu uucugcuaac g                                              21

<210> SEQ ID NO 128
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (5)..(17)
<223> OTHER INFORMATION: 2'-O-methyl modified

<400> SEQUENCE: 128
cguuagcaga aacaaaagga g                                              21

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
```

```
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 129
cuccuuuugu uucugcuaac g                                              21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 130
cguuagcaga aacaaaagga g                                              21

<210> SEQ ID NO 131
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 131
cuccuuuugu uucugcuaac g                                              21

<210> SEQ ID NO 132
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 132
cguuagcaga aacaaaagga g                                              21

<210> SEQ ID NO 133
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 133
cuccuuuugu uucugcuaac g                                              21

<210> SEQ ID NO 134
<211> LENGTH: 21
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 134
cguuagcaga aacaaaagga g                                              21

<210> SEQ ID NO 135
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 135
cuccuuuugu uucugcuaac g                                              21

<210> SEQ ID NO 136
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(11)
<223> OTHER INFORMATION: 2'-O-methyl modified

<400> SEQUENCE: 136
cguuagcaga aacaaaagga g                                              21

<210> SEQ ID NO 137
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 137
cuccuuuugu uucugcuaac g                                              21

<210> SEQ ID NO 138
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (11)..(21)
<223> OTHER INFORMATION: 2'-O-methyl modified

<400> SEQUENCE: 138
cguuagcaga aacaaaagga g                                              21

<210> SEQ ID NO 139
<211> LENGTH: 21
```

```
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (8)..(13)
<223> OTHER INFORMATION: 2'-O-methyl modified

<400> SEQUENCE: 139
cuccuuuugu uucugcuaac g                                              21

<210> SEQ ID NO 140
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 140
cguuagcaga aacaaaagga g                                              21

<210> SEQ ID NO 141
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (6)..(10)
<223> OTHER INFORMATION: 2'-O-methyl modified
<220> FEATURE:
<221> NAME/KEY: modified_base
<222> LOCATION: (16)..(21)
<223> OTHER INFORMATION: 2'-O-methyl modified

<400> SEQUENCE: 141
cuccuuuugu uucugcuaac g                                              21

<210> SEQ ID NO 142
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (7)..(12)
<223> OTHER INFORMATION: 2'-O-methyl modified
<220> FEATURE:
<221> NAME/KEY: modified_base
<222> LOCATION: (17)..(21)
<223> OTHER INFORMATION: 2'-O-methyl modified

<400> SEQUENCE: 142
cguuagcaga aacaaaagga g                                              21

<210> SEQ ID NO 143
<211> LENGTH: 21
<212> TYPE: RNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (7)..(15)
<223> OTHER INFORMATION: 2'-O-methyl modified

<400> SEQUENCE: 143
cuccuuuugu uucugcuaac g                                           21

<210> SEQ ID NO 144
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(21)
<223> OTHER INFORMATION: 2'-O-methyl modified

<400> SEQUENCE: 144
cguuagcaga aacaaaagga g                                           21

<210> SEQ ID NO 145
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
```

<223> OTHER INFORMATION: 2'-O-methyl modified

<400> SEQUENCE: 145
cuccuuuugu uucugcuaac g                                                    21

<210> SEQ ID NO 146
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 146
cguuagcaga aacaaaagga g                                                    21

<210> SEQ ID NO 147
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified

```
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 147
cuccuuuugu uucugcuaac g                                              21

<210> SEQ ID NO 148
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
```

<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 148
cguuagcaga aacaaaagga g        21

<210> SEQ ID NO 149
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 149
cuccuuuugu uucugcuaac g        21

<210> SEQ ID NO 150
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)

```
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 150
cguuagcaga aacaaaagga g                                          21

<210> SEQ ID NO 151
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
```

```
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 151
cuccuuuugu uucugcuaac g                                              21

<210> SEQ ID NO 152
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 152
cguuagcaga aacaaaagga g                                              21

<210> SEQ ID NO 153
<211> LENGTH: 21
<212> TYPE: DNA
<213> ORGANISM: Artificial Sequence
<220> FEATURE:
```

```
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 153
ucuugaugua cuccccucgt t                                                     21

<210> SEQ ID NO 154
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 154
cgaggggagu acaucaagat t                                                     21

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ucuugaugua cuccccucg                                                        19

<210> SEQ ID NO 156
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 156
cgaggggagu acaucaaga                                                        19

<210> SEQ ID NO 157
<211> LENGTH: 19
<212> TYPE: RNA
<213> ORGANISM: Artificial Sequence
<220> FEATURE:
<221> NAME/KEY: source
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
```

```
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 157
ucuugaugua cuccccucg                                              19

<210> SEQ ID NO 158
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 158
cgaggggagu acaucaaga                                              19
```

```
<210> SEQ ID NO 159
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 159
ucuugaugua cuccccucg                                                   19

<210> SEQ ID NO 160
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
```

```
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 160 cgagggagu acaucaaga                                                   19

<210> SEQ ID NO 161
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
```

<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 161
ucuugaugua cuccccucg                                                                19

<210> SEQ ID NO 162
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 162
cgaggggagu acaucaaga                                                                19

<210> SEQ ID NO 163
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified

```
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 163
ucuugaugua cuccccucg                                              19

<210> SEQ ID NO 164
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
```

```
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 164 cgagggagu acaucaaga                                                19

<210> SEQ ID NO 165
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 165
aauuccagug guucauucc                                               19

<210> SEQ ID NO 166
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 166
ggaaugaacc acuggaauu                                               19

<210> SEQ ID NO 167
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
```

```
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 167
aauuccagug guucauucc                                                   19

<210> SEQ ID NO 168
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 168
ggaaugaacc acuggaauu                                                   19

<210> SEQ ID NO 169
<211> LENGTH: 19
<212> TYPE: RNA
<213> ORGANISM: Artificial Sequence
<220> FEATURE:
<223> OTHER INFORMATION: Description of Artificial Sequence: Synthetic
```

```
            oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 169
aauuccagug guucauucc                                                    19

<210> SEQ ID NO 170
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
```

```
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 170
ggaaugaacc acuggaauu                                                19

<210> SEQ ID NO 171
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 171
```
aauuccagug guucauucc                                                    19

<210> SEQ ID NO 172
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: modified_base
<222> LOCATION: (20)..(20)
<223> OTHER INFORMATION: 2'-O-methyl modified

<400> SEQUENCE: 172
ggaaugaacc acuggaauu                                                    19

<210> SEQ ID NO 173
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified

```
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 173
aauuccagug guucauucc                                                19

<210> SEQ ID NO 174
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
```

-continued

```
<222> LOCATION: (19)..(19)
<223> OTHER INFORMATION: 2'-O-methyl modified
<220> FEATURE:
<221> NAME/KEY: modified_base
<222> LOCATION: (21)..(21)
<223> OTHER INFORMATION: 2'-O-methyl modified

<400> SEQUENCE: 174
ggaaugaacc acuggaauu                                                19

<210> SEQ ID NO 175
<211> LENGTH: 12
<212> TYPE: DNA
<213> ORGANISM: Artificial Sequence
<220> FEATURE:
<223> OTHER INFORMATION: Description of Artificial Sequence: Synthetic
      pA-loop

<400> SEQUENCE: 175
aaaaaaaaaa aa                                                       12

<210> SEQ ID NO 176
<211> LENGTH: 22
<212> TYPE: DNA
<213> ORGANISM: Artificial Sequence
<220> FEATURE:
<223> OTHER INFORMATION: Description of Artificial Sequence:  Synthetic
      primer

<400> SEQUENCE: 176
caccgccaaa tttaactgca ga                                            22

<210> SEQ ID NO 177
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 177
aagggtttga taagttctag ctgt                                          24

<210> SEQ ID NO 178
<211> LENGTH: 31
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 178
tgcacagtat cctttgaag accataaccc a                                   31

<210> SEQ ID NO 179
<211> LENGTH: 22
<212> TYPE: DNA
<213> ORGANISM: Artificial Sequence
<220> FEATURE:
<222> LOCATION:
<223> OTHER INFORMATION: Description of Artificial Sequence: Synthetic
      primer

<400> SEQUENCE: 179
gtttgagacc ttcaacaccc ca                                            22

<210> SEQ ID NO 180
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 180
gaccagaggc atacagggac a                                                   21

<210> SEQ ID NO 181
<211> LENGTH: 26
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 181
ccatgtacgt agccatccag gctgtg                                              26

<210> SEQ ID NO 182
<211> LENGTH: 23
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 182
ucuccuuttg tttctgcuaa cga                                                 23

<210> SEQ ID NO 183
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
```

```
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 183
acaacagacu uuaauguaa                                                     19

<210> SEQ ID NO 184
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-SH)(Cy5.5) modified

<400> SEQUENCE: 184
acaacagacu uuaauguaa                                                     19

<210> SEQ ID NO 185
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
```

```
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: misc_feature
<222> LOCATION: (19)..(19)
<223> OTHER INFORMATION: (cholesteryl-TEG) modified

<400> SEQUENCE: 185
acaacagacu uuaauguaa                                               19

<210> SEQ ID NO 186
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-S-SC6) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
```

```
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 186
acaacagacu uuaauguaa                                                19

<210> SEQ ID NO 187
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (C6-NH2) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-NH) modified

<400> SEQUENCE: 187
acaacagacu uuaauguaa                                                19
```

<210> SEQ ID NO 188
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-NH) (Cy5.5) modified

<400> SEQUENCE: 188
uuacauuaaa gucuguugu                                                19

<210> SEQ ID NO 189
<211> LENGTH: 19
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:

```
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: misc_feature
<222> LOCATION: (19)..(19)
<223> OTHER INFORMATION: (C6-NH2) modified

<400> SEQUENCE: 189
uuacauuaaa gucuguugu                                              19

<210> SEQ ID NO 190
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
```

-continued

```
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified
<220> FEATURE:
<221> NAME/KEY: misc_feature
<222> LOCATION: (19)..(19)
<223> OTHER INFORMATION: (C3-S-S-C3) modified

<400> SEQUENCE: 190
uuacauuaaa gucuguugu                                                    19

<210> SEQ ID NO 191
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 191
acaacagacu uuaauguaa                                                    19

<210> SEQ ID NO 192
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: 2'-O-methyl modified
<220> FEATURE:
<221> NAME/KEY: modified_base
<222> LOCATION: (3)..(3)
<223> OTHER INFORMATION: 2'-O-methyl modified
```

```
<220> FEATURE:
<221> NAME/KEY: modified_base
<222> LOCATION: (5)..(5)
<223> OTHER INFORMATION: 2'-O-methyl modified
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(11)
<223> OTHER INFORMATION: 2'-O-methyl modified
<220> FEATURE:
<221> NAME/KEY: modified_base
<222> LOCATION: (13)..(13)
<223> OTHER INFORMATION: 2'-O-methyl modified
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (17)..(17)
<223> OTHER INFORMATION: 2'-O-methyl modified
<220> FEATURE:
<221> NAME/KEY: modified_base
<222> LOCATION: (19)..(19)
<223> OTHER INFORMATION: 2'-O-methyl modified

<400> SEQUENCE: 192
uuacauuaaa gucuguugu                                             19

<210> SEQ ID NO 193
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (2)..(2)
<223> OTHER INFORMATION: 2'-fluoro-nucleotide
<220> FEATURE:
<221> NAME/KEY: modified_base
<222> LOCATION: (5)..(5)
<223> OTHER INFORMATION: 2'-fluoro-nucleotide
<220> FEATURE:
<221> NAME/KEY: modified_base
<222> LOCATION: (9)..(9)
<223> OTHER INFORMATION: 2'-fluoro-nucleotide
<220> FEATURE:
<221> NAME/KEY: modified_base
<222> LOCATION: (11)..(11)
<223> OTHER INFORMATION: 2'-fluoro-nucleotide
<220> FEATURE:
<221> NAME/KEY: modified_base
<222> LOCATION: (20)..(21)
<223> OTHER INFORMATION: 2'-O-methyl modified

<400> SEQUENCE: 193
acaacagact utaatgtaau u                                          21

<210> SEQ ID NO 194
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-fluoro-nucleotide
<220> FEATURE:
<221> NAME/KEY: modified_base
<222> LOCATION: (7)..(7)
<223> OTHER INFORMATION: 2'-O-methyl modified
<220> FEATURE:
<221> NAME/KEY: modified_base
<222> LOCATION: (9)..(9)
<223> OTHER INFORMATION: 2'-O-methyl modified
<220> FEATURE:
<221> NAME/KEY: modified_base
<222> LOCATION: (11)..(12)
<223> OTHER INFORMATION: 2'-O-methyl modified
<220> FEATURE:
<221> NAME/KEY: modified_base
<222> LOCATION: (13)..(14)
<223> OTHER INFORMATION: 2'-fluoro-nucleotide
<220> FEATURE:
<221> NAME/KEY: modified_base
<222> LOCATION: (15)..(15)
<223> OTHER INFORMATION: 2'-O-methyl modified
<220> FEATURE:
<221> NAME/KEY: modified_base
<222> LOCATION: (16)..(16)
<223> OTHER INFORMATION: 2'-fluoro-nucleotide
<220> FEATURE:
<221> NAME/KEY: modified_base
<222> LOCATION: (17)..(18)
<223> OTHER INFORMATION: 2'-O-methyl modified
<220> FEATURE:
<221> NAME/KEY: modified_base
<222> LOCATION: (19)..(19)
<223> OTHER INFORMATION: 2'-fluoro-nucleotide
<220> FEATURE:
<221> NAME/KEY: modified_base
<222> LOCATION: (20)..(21)
<223> OTHER INFORMATION: 2'-O-methyl modified

<400> SEQUENCE: 194
uuacauuaaa gucuguuguu u                                             21

<210> SEQ ID NO 195
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(1)
<223> OTHER INFORMATION: (HSC6) modified
<220> FEATURE:
<221> NAME/KEY: modified_base
<222> LOCATION: (2)..(2)
<223> OTHER INFORMATION: 2'-O-methyl modified
<220> FEATURE:
<221> NAME/KEY: modified_base
<222> LOCATION: (4)..(4)
<223> OTHER INFORMATION: 2'-O-methyl modified
<220> FEATURE:
<221> NAME/KEY: modified_base
<222> LOCATION: (6)..(6)
<223> OTHER INFORMATION: 2'-O-methyl modified

```
<220> FEATURE:
<221> NAME/KEY: modified_base
<222> LOCATION: (8)..(8)
<223> OTHER INFORMATION: 2'-O-methyl modified
<220> FEATURE:
<221> NAME/KEY: modified_base
<222> LOCATION: (10)..(10)
<223> OTHER INFORMATION: 2'-O-methyl modified
<220> FEATURE:
<221> NAME/KEY: modified_base
<222> LOCATION: (12)..(12)
<223> OTHER INFORMATION: 2'-O-methyl modified
<220> FEATURE:
<221> NAME/KEY: modified_base
<222> LOCATION: (14)..(14)
<223> OTHER INFORMATION: 2'-O-methyl modified
<220> FEATURE:
<221> NAME/KEY: modified_base
<222> LOCATION: (16)..(16)
<223> OTHER INFORMATION: 2'-O-methyl modified
<220> FEATURE:
<221> NAME/KEY: modified_base
<222> LOCATION: (18)..(18)
<223> OTHER INFORMATION: 2'-O-methyl modified

<400> SEQUENCE: 195
acaacagacu uuaauguaa                                                    19
```